(12) United States Patent
Baldwin et al.

(10) Patent No.: US 12,161,737 B2
(45) Date of Patent: *Dec. 10, 2024

(54) WHIPPED FORMULATIONS

(71) Applicant: FORMULATED SOLUTIONS, LLC, Largo, FL (US)

(72) Inventors: Stephen Baldwin, Flanders, NJ (US); Scott Carpenter, Palm Harbor, FL (US); Heidi Graham, Charlottesville, VA (US); Nanhye Kim, New Providence, NJ (US); Tom Meyer, Germantown, TN (US); David Reynolds, Ooltewah, TN (US); Jerry Vancleave, Lakeland, TN (US); Eric Dann, Safety Harbor, FL (US); Thomas Dann, Palm Harbor, FL (US); Renee Nelson, Brandon, FL (US); Brian Dann, Clearwater, FL (US)

(73) Assignee: FORMULATED SOLUTIONS, LLC, Largo, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/124,291

(22) Filed: Mar. 21, 2023

(65) Prior Publication Data

US 2023/0355485 A1    Nov. 9, 2023

Related U.S. Application Data

(63) Continuation of application No. 16/300,270, filed as application No. PCT/US2017/032292 on May 11, 2017, now Pat. No. 11,622,922.

(60) Provisional application No. 62/334,862, filed on May 11, 2016, provisional application No. 62/351,385, filed on Jun. 17, 2016, provisional application No. 62/396,424, filed on Sep. 19, 2016, provisional application No. 62/396,415, filed on Sep. 19, 2016.

(51) Int. Cl.

| | | |
|---|---|---|
| A61K 8/04 | (2006.01) |
| A23P 30/40 | (2016.01) |
| A61K 8/19 | (2006.01) |
| A61K 8/27 | (2006.01) |
| A61K 9/12 | (2006.01) |
| A61Q 5/06 | (2006.01) |
| A61Q 7/00 | (2006.01) |
| A61Q 11/00 | (2006.01) |
| A61Q 17/04 | (2006.01) |
| A61Q 19/00 | (2006.01) |
| B65D 83/14 | (2006.01) |
| B65D 83/20 | (2006.01) |
| B65D 83/62 | (2006.01) |

(52) U.S. Cl.
CPC .............. *A61K 8/046* (2013.01); *A23P 30/40* (2016.08); *A61K 8/19* (2013.01); *A61K 8/27* (2013.01); *A61K 9/122* (2013.01); *A61Q 5/06* (2013.01); *A61Q 7/00* (2013.01); *A61Q 11/00* (2013.01); *A61Q 17/04* (2013.01); *A61Q 19/00* (2013.01); *A61Q 19/004* (2013.01); *B65D 83/207* (2013.01); *B65D 83/62* (2013.01); *B65D 83/752* (2013.01); *A61K 2800/22* (2013.01); *A61K 2800/87* (2013.01)

(58) Field of Classification Search
CPC .......... A61K 8/046; A61K 9/122; A61K 8/27; A61K 8/19; A61K 2800/22; A61K 2800/87; B65D 83/207; B65D 83/62; B65D 83/752; A61Q 7/00; A61Q 11/00; A61Q 19/004; A61Q 5/06; A61Q 17/04; A61Q 19/00; A23P 30/40; A61P 17/02
See application file for complete search history.

(56) References Cited

U.S. PATENT DOCUMENTS

| | | |
|---|---|---|
| 3,395,215 A | 7/1968 | Schubert et al. |
| 3,710,538 A | 1/1973 | Lowy |
| 3,970,584 A | 7/1976 | Hart et al. |
| 4,670,272 A | 6/1987 | Chen et al. |
| 5,104,987 A | 4/1992 | King |
| 5,214,925 A | 6/1993 | Hoy et al. |
| 5,560,859 A | 10/1996 | Hartmann et al. |
| 5,858,343 A | 1/1999 | Szymczak |
| 6,322,776 B1 | 11/2001 | Ortega, II |
| 7,070,722 B1 | 7/2006 | Gilchrist et al. |

(Continued)

FOREIGN PATENT DOCUMENTS

| | | |
|---|---|---|
| AU | 2017263531 A1 | 10/2018 |
| AU | 2017263533 A1 | 10/2018 |

(Continued)

OTHER PUBLICATIONS

Office Action received in U.S. Appl. No. 16/300,323, filed Jun. 12, 2020, 17 pages.

(Continued)

*Primary Examiner* — Robert A Wax
*Assistant Examiner* — Quanglong N Truong
(74) *Attorney, Agent, or Firm* — Liang & Hennessey LLP; Stanley D. Liang

(57) ABSTRACT

The present disclosure relates to, inter alia, a formulation in a package. The formulation comprises one or more active agents and is co-mingled with a whipping agent prior to being filled under pressure into the package. The whipping agent is added in sufficient amounts to be dispersed in the formulation. The pressurized package is under sufficient pressure suitable to maintain the whipping agent dispersed in the formulation; and the pressurized package is under sufficient pressure to expel the formulation as a whipped formulation upon application of external force on the formulation in the package.

17 Claims, 69 Drawing Sheets

(56) References Cited

U.S. PATENT DOCUMENTS

| | | | |
|---|---|---|---|
| 2004/0052826 | A1 | 3/2004 | Fernandez-Kleinlein et al. |
| 2004/0197270 | A1 | 10/2004 | Mundschenk |
| 2004/0241099 | A1 | 12/2004 | Popp et al. |
| 2004/0247534 | A1 | 12/2004 | Stoltz |
| 2004/0258627 | A1 | 12/2004 | Riedel et al. |
| 2004/0258628 | A1 | 12/2004 | Riedel et al. |
| 2005/0079142 | A1 | 4/2005 | Brunckhorst et al. |
| 2008/0017671 | A1 | 1/2008 | Shieh et al. |
| 2008/0138296 | A1 | 6/2008 | Tamarkin et al. |
| 2008/0253973 | A1 | 10/2008 | Tamarkin et al. |
| 2008/0260655 | A1 | 10/2008 | Tamarkin et al. |
| 2011/0281827 | A1 | 11/2011 | Tamarkin et al. |
| 2012/0087872 | A1 | 4/2012 | Tamarkin et al. |
| 2012/0213712 | A1 | 8/2012 | Kasai et al. |
| 2012/0288462 | A1 | 11/2012 | Lebok et al. |
| 2012/0288465 | A1 | 11/2012 | Lechel |
| 2012/0301422 | A1 | 11/2012 | Meyer |
| 2013/0011341 | A1 | 1/2013 | Nguyen et al. |
| 2013/0233310 | A1 | 9/2013 | Hilgers et al. |
| 2014/0030198 | A1 | 1/2014 | Fares et al. |
| 2014/0079648 | A1 | 3/2014 | Cohen |
| 2014/0120039 | A1 | 5/2014 | Baldwin et al. |
| 2014/0131395 | A1 | 5/2014 | Chang |
| 2016/0101051 | A1 | 4/2016 | Tamarkin et al. |
| 2016/0202051 | A1 | 7/2016 | Heist et al. |
| 2019/0142709 | A1 | 5/2019 | Baldwin et al. |
| 2019/0151207 | A1 | 5/2019 | Baldwin et al. |
| 2019/0282464 | A1 | 9/2019 | Baldwin et al. |
| 2019/0367256 | A1 | 12/2019 | Baldwin et al. |

FOREIGN PATENT DOCUMENTS

| | | | |
|---|---|---|---|
| CN | 1217650 | A | 5/1990 |
| CN | 1713891 | A | 12/2005 |
| CN | 103547247 | A | 1/2014 |
| CN | 110035737 | A | 7/2019 |
| DE | 10229812 | A1 | 1/2004 |
| DE | 10304721 | A1 | 8/2004 |
| EP | 1391192 | A1 | 2/2004 |
| EP | 1508326 | A1 | 2/2005 |
| EP | 2319586 | A1 | 5/2011 |
| EP | 2636401 | A1 | 9/2013 |
| EP | 3454662 | A1 | 3/2019 |
| EP | 3454826 | A1 | 3/2019 |
| EP | 3454946 | A1 | 3/2019 |
| ES | 2560540 | T3 | 2/2016 |
| JP | H3131680 | | 3/1991 |
| JP | H0625051 | B2 | 2/1994 |
| WO | 0103663 | A | 1/2001 |
| WO | 2004022019 | A1 | 3/2004 |
| WO | 2005007516 | A2 | 1/2005 |
| WO | 2012154918 | A2 | 11/2012 |
| WO | 2017112727 | A1 | 6/2017 |
| WO | 2017197193 | A1 | 11/2017 |
| WO | 2017197194 | A1 | 11/2017 |
| WO | 2017197195 | A1 | 11/2017 |
| WO | 2017197196 | A1 | 11/2017 |
| WO | 2017197202 | A1 | 11/2017 |

OTHER PUBLICATIONS

USPTO, Non-Final Rejection of the US Exam Report on U.S. Appl. No. 16/300,342 (Feb. 23, 2023), 15 pages.
USPTO, Non-Final Rejection of the US Exam Report on U.S. Appl. No. 16/300,323 (Feb. 8, 2023), 19 pages.
Zhang et al., "Nonionic Surfactant Application Patent Technology," China Light Industry Press, Mar. 31, 2001, pp. 1-2.
Chinese National Intellectual Property Administration, Chinese Second Office Action for App. No. 201780028415.1 (Sep. 5, 2022), pp. 1-17.
USPTO, Non-Final Rejection of the US Exam Report on U.S. Appl. No. 16/300,342 (Aug. 10, 2022).
Chinese Office Action received in 201880031248.0, dated Apr. 18, 2022, pp. 6.
Chinese Office Action received in 201780024815.1, dated Dec. 6, 2021, pp. 14.
Chinese Office Action received in 201780028486.1, dated Nov. 8, 2021, pp. 12.
Food Crumbles, The Science of Foams in Food, Apr. 5, 2020, https://foodcrumbles.com/science-of-foams-in-food (Year 2020), 14 pgs.
BPO, Brazilian Office Action received in Brazilian Application No. BR112018073118-8 mailed Nov. 8, 2021, 4 pages.
Mexican Patent Office, Mexican Official Action for Mexican App. No. MX/a/2018/013754 (Jun. 22, 2021), pp. 1-6.
USPTO, Non-Final Rejection of the US Exam Report for U.S. Appl. No. 16/300,342 (Jun. 24, 2021), pp. 1-13.
Dailymed, "Coppertone Defend and Care Oil Free Lotion SPF 30," www.dailymed.nim.nih.gov. Published online Dec. 17, 2015, pp. 1-3.
Australia IP, Examination Report No. 1 for Standard Patent Application for Australian App. No. 2017263538 (Feb. 25, 2021).
USPTO, Non-Final Rejection of the US Exam Report for U.S. Appl. No. 16/300,345 (Feb. 5, 2021).
USPTO, Non-Final Rejection of the US Exam Report for U.S. Appl. No. 16/300,323 (Jun. 12, 2020).
CIPO, Examination Report and Examination Search Report for Canadian App. No. 3,023,714 (Mar. 1, 2021).
EPO, Communication Pursuant to Article 94(3) EPC for European App. No. 17726753.1.
Australia IP, Examination Report No. 1 for Standard Patent Application for Australian App. No. 2017263531 (Feb. 25, 2021).
USPTO, Non-Final Rejection of the US Exam Report for U.S. Appl. No. 16/300,245 (Jul. 23, 2020).
USPTO, Final Rejection of the US Exam Report for U.S. Appl. No. 16/300,323 (Nov. 18, 2020).
CIPO, Examination Report and Examination Search Report for Canadian App. No. 3,023,669 (Jan. 29, 2021).
Australia IP, Examination Report No. 1 for Standard Patent Application for Australian App. No. 2017263532 (Feb. 25, 2021).
CIPO, Examination Report and Examination Search Report for Canadian App. No. 3,023,680 (Feb. 17, 2021).
EPO, Communication Pursuant to Article 94(3) EPC for European App. No. 17725450.5 (Mar. 19, 2021).
Australia IP, Examination Report No. 1 for Standard Patent Application for Australian App. No. 2017263533 (Feb. 25, 2021).
CIPO, Examination Report and Examination Search Report for Canadian App. No. 3,023,702 (Feb. 1, 2021).
EPO, Communication Pursuant to Article 94(3) EPC for European App. No. 17726754.9 (Feb. 23, 2021).
Australia IP, Examination Report No. 1 for Standard Patent Application for Australian App. No. 2017263534 (Feb. 25, 2021).
USPTO, Non-Final Rejection of the US Exam Report for U.S. Appl. No. 16/300,342 (Jul. 8, 2020).
CIPO, Examination Report and Examination Search Report for Canadian App. No. 3,023,703 (Feb. 12, 2021).
EPO, Communication Pursuant to Article 94(3) EPC for European App. No. 17726162.5 (Apr. 2, 2021).
EPO, Communication Pursuant to Article 94(3) EPC for European App. No. 17725453.9 (Mar. 19, 2021).
USPTO, Non-Final Rejection of the US Exam Report for U.S. Appl. No. 16/300,342 (Dec. 11, 2020).
USPTO, Non-Final Rejection of the US Exam Report for U.S. Appl. No. 16/300,289 (Feb. 5, 2021).
USPTO, Non-Final Rejection of the US Exam Report for U.S. Appl. No. 16/300,289 (Jul. 27, 2020).
International Search Report and Written Opinion received in PCT/US2017/032292 dated Jul. 26, 2017, pp. 10.
International Preliminary Report received in PCT/US2017/032292 dated Nov. 13, 2018, pp. 7.
Aurena Laboratories, "SunScreen Bag on Valve", Retrieved from the Internet, Nov. 19, 2014 pp. 1.
International Search Report and Written Opinion received in PCT/US2017/032277 dated Aug. 1, 2017, pp. 15.

(56) References Cited

OTHER PUBLICATIONS

International Preliminary Report received in PCT/US2017/032277 dated Nov. 13, 2018, pp. 10.
International Search Report and Written Opinion received in PCT/US2017/032278 dated Jul. 26, 2017, pp. 9.
International Preliminary Report received in PCT/US2017/032278 dated Nov. 13, 2018, pp. 6.
Mintel, "Hair Styling Foam", Oct. 2013, XP002772098, Online.
Mintel, "Pack Facial Mask", Mar. 2016, XP002772099, Online.
Mintel, "Body Whip Moisture Cream", Jul. 2008, XP002772100, Online.
Mintel, "Body Whip Cream", Jul. 2008, XP002772101, Online.
International Search Report and Written Opinion received in PCT/US2017/032279 dated Jul. 28, 2017, pp. 11.
International Preliminary Report received in PCT/US2017/032279 dated Nov. 13, 2018, pp. 8.
International Search Report and Written Opinion received in PCT/US2017/032281 dated Aug. 1, 2017, pp. 16.
International Preliminary Report received in PCT/US2017/032281 dated Nov. 13, 2018, pp. 11.

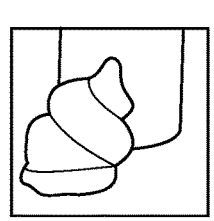
Appearance of a "Whipped-foam" delivered from a Whipped Sunscreen Lotion SPF 30

FIG. 1A

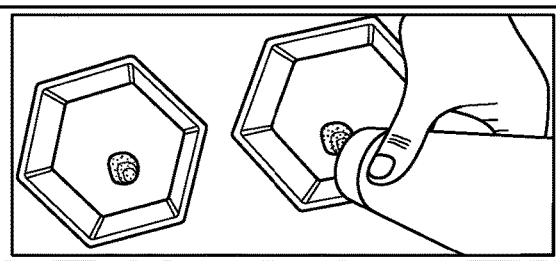
Application of Two Lotions (Left: a Whipped Sunscreen Lotion SPF 30, Right: Kiehl's Sunscreen Lotion SPF 30)

FIG. 1B

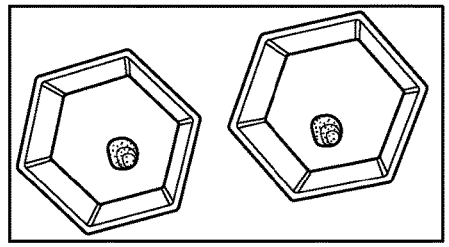
T=Initial

Applied amounts of two lotions are similar

FIG. 1C

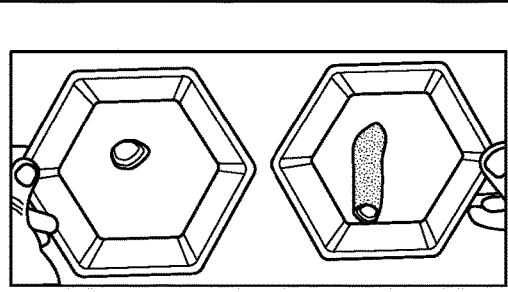
T= 10 Seconds

Left (Whipped Sunscreen SPF 30) = No change in appearance and no tendency to run
Right (Kiehl's Sunscreen SPF 30) = Become runny

FIG. 1D

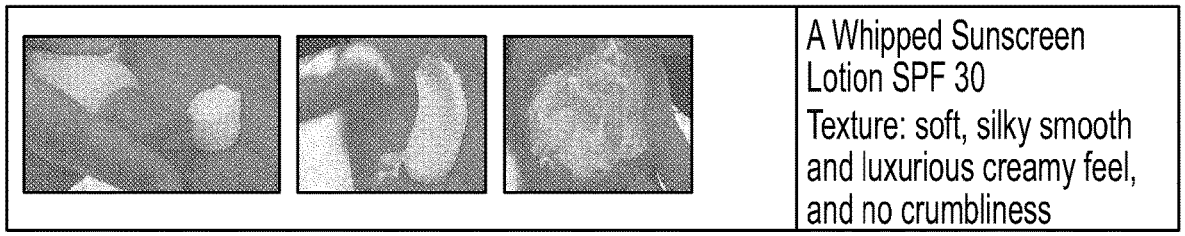

FIG. 2A — A Whipped Sunscreen Lotion SPF 30. Texture: soft, silky smooth and luxurious creamy feel, and no crumbliness

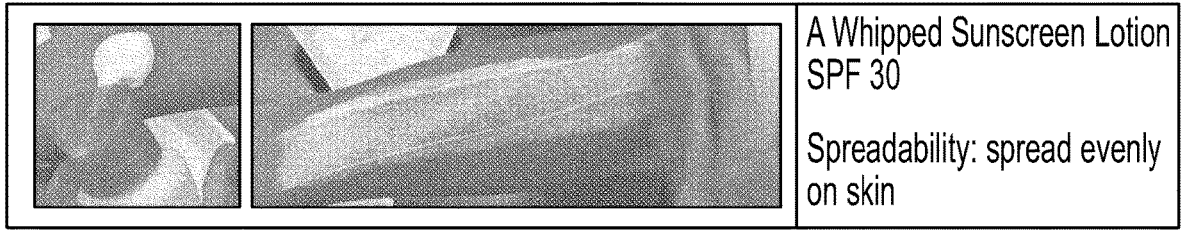

FIG. 2B — A Whipped Sunscreen Lotion SPF 30. Spreadability: spread evenly on skin

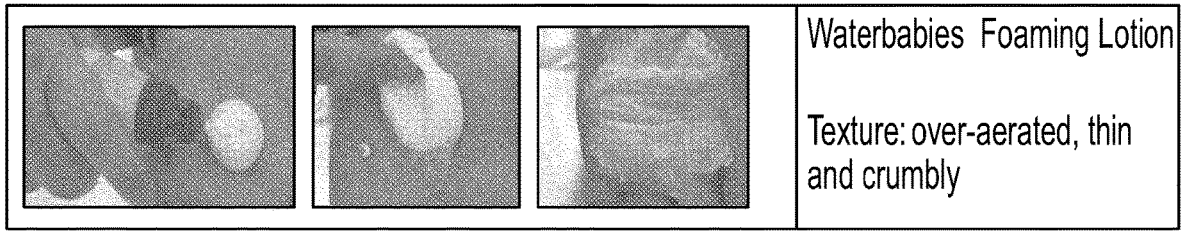

FIG. 2C — Waterbabies Foaming Lotion. Texture: over-aerated, thin and crumbly

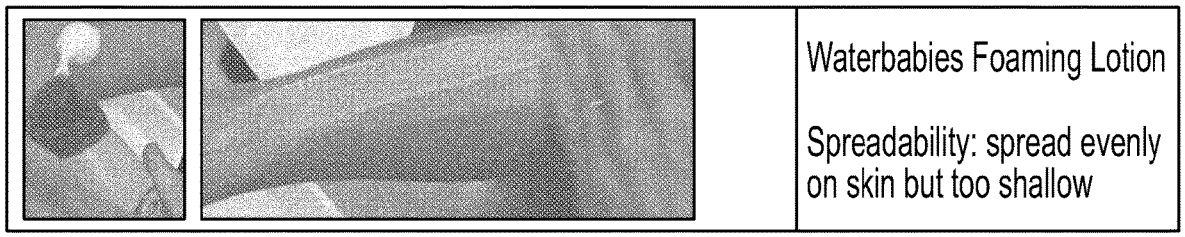

FIG. 2D — Waterbabies Foaming Lotion. Spreadability: spread evenly on skin but too shallow

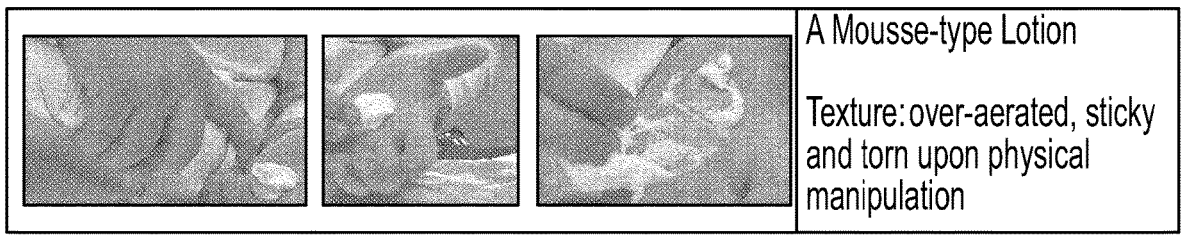

FIG. 2E — A Mousse-type Lotion. Texture: over-aerated, sticky and torn upon physical manipulation

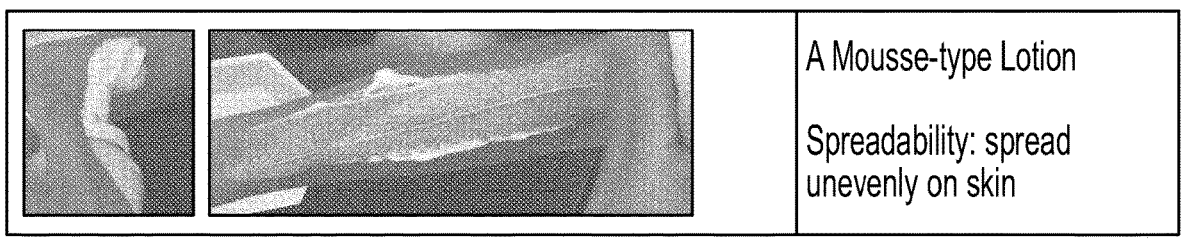

FIG. 2F — A Mousse-type Lotion. Spreadability: spread unevenly on skin

Left: Waterbabies Foaming Sunscreen Lotion

Right: Whipped Sunscreen Lotion

Left: Clearly Sheer Sunscreen Lotion

Right: Whipped Sunscreen Lotion

| "Whipped-foam" Dispensed After T=24 Hours at RT | N/A | N/A | 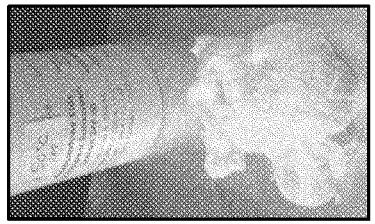 | N/A | N/A | 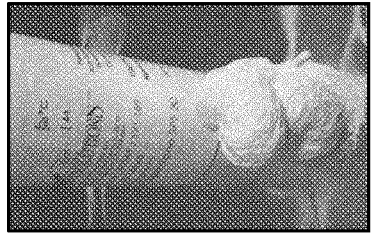 |
*T=0 pictures were taken right after pulling out the samples from 40°C/75%RH or 50°C/75%RH storage condition.
** Y71-128 (CT Whipped Cleary Sheer Lotion SPF 30) and Y71-189 (CT Whipped Ultraguard Kids Lotion SPF 30)
*** Z16-001 (CT Whipped Waterbabies Lotion SPF 50) and Y71-159 (CT Whipped Waterbabies Lotion SPF 50,
FIG. 6 (Cont.)

| | | | | |
|---|---|---|---|---|
| T=0 | <20 um | 23.2% | <20 um | 5.6% |
| | 20.0-40.0 um | 30.0% | 20.0-40.0 um | 19.2% |
| | 40.1-60.0 um | 10.8% | 40.1-60.0 um | 20.0% |
| | 60.1-100.0 um | 13.3% | 60.1-100.0 um | 27.2% |
| | 100.1-200.0 um | 20.2% | 100.1-200.0 um | 24.8% |
| | 200.1-300.0 um | 1.5% | 200.1-233 um | 3.2% |
| | 300.1-396 um | 1.0% | ≤60 um: 45 %, ≤100 um: 72 % | |
| | ≤60 um: 64 %, ≤100 um: 77 % | | | |
| After T=20 min. at RT | | | | |
| After T=20 min. at RT | | | | |
| After T=20 min. at RT | <20 um | 11.1% | <20 um | 13.1% |
| | 20.0-40.0 um | 44.4% | 20.0-40.0 um | 32.7% |
| | 40.1-60.0 um | 19.8% | 40.1-60.0 um | 14.0% |
| | 60.1-100.0 um | 18.5% | 60.1-100.0 um | 24.3% |
| | 100.1-200.0 um | 4.9% | 100.1-200.0 um | 11.2% |
| | 200.1-346 um | 1.2% | 200.1-300.0 um | 3.7% |
| | ≤60 um: 75 %, ≤100 um: 94 % | | 300.1-356 um | 0.9% |
| | | | ≤60 um: 60 %, ≤100 um: 84 % | |

FIG. 7B

| | | | | |
|---|---|---|---|---|
| T=0 | <20 um | 8.7% | <20 um: | 4.7% |
| | 20.0-40.0 um | 15.0% | 20.0-40.0 um: | 31.4% |
| | 40.1-60.0 um | 14.2% | 40.1-60.0 um: | 9.3% |
| | 60.1-100.0 um | 32.3% | 60.1-100.0 um: | 24.4% |
| | 100.1-200.0 um | 26.8% | 100.1-200.0 um: | 22.1% |
| | 200.1-240 um | 3.2% | 200.1-300.0 um: | 7.0% |
| | | | 300.1-309 um: | 1.2% |
| | ≤60 um: 38 %, ≤100 um: 70 % | | ≤60 um: 45 %, ≤100 um: 70 % | |
| After T=20 min. at RT | 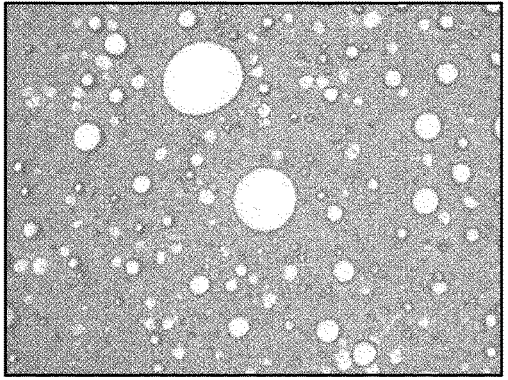 | | 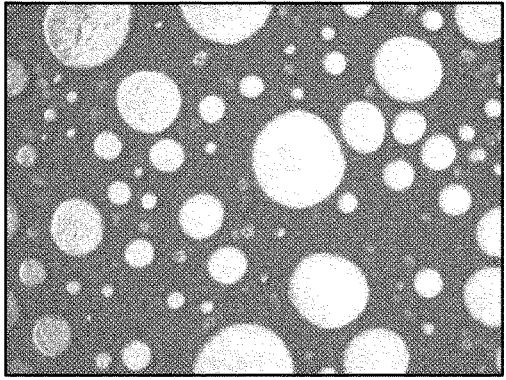 | |
| After T=20 min. at RT | 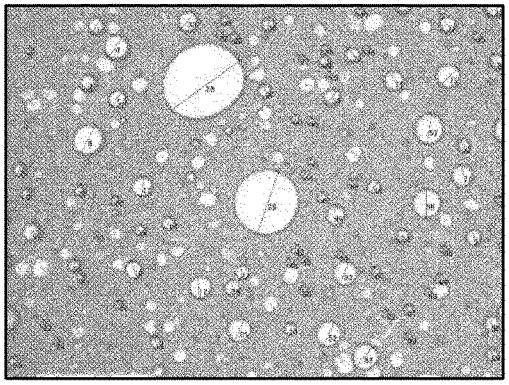 | | 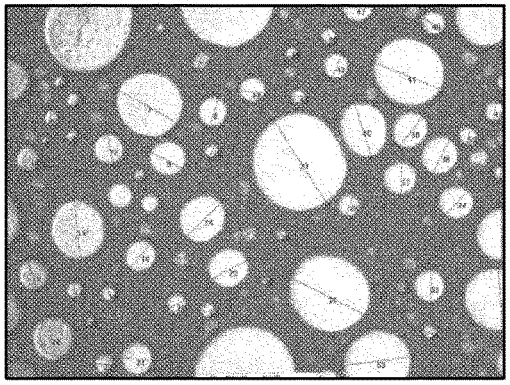 | |
| After T=20 min. at RT | <20 um | 6.1% | 20.0-40.0 um | 5.7% |
| | 20.0-40.0 um | 35.4% | 40.1-60.0 um | 32.1% |
| | 40.1-60.0 um | 36.6% | 60.1-100.0 um | 18.9% |
| | 60.1-100.0 um | 18.3% | 100.1-200.0 um | 34.0% |
| | 100.1-200.0 um | 1.2% | 200.1-300.0 um | 7.6% |
| | 200.1-254 um | 2.4% | 300.1-315 um | 1.9% |
| | ≤60 um: 78 %, ≤100 um: 96 % | | ≤60 um: 38 %, ≤100 um: 57 % | |
FIG. 8B

| | | | | |
|---|---|---|---|---|
| T=0 | <20 um | 4.2% | <20 um | 13.2% |
| | 20.0-40.0 um | 31.4% | 20.0-40.0 um | 33.6% |
| | 40.1-60.0 um | 11.0% | 40.1-60.0 um | 17.1% |
| | 60.1-100.0 um | 16.1% | 60.1-100.0 um | 18.4% |
| | 100.1-200.0 um | 33.1% | 100.1-200.0 um | 14.5% |
| | 200.1-254 um | 4.2% | 200.1-300.0 um | 2.0% |
| | | | 300.1-364 um | 1.3% |
| | ≤60 um: 47 %, ≤100 um: 63 % | | ≤60 um: 64 %, ≤100 um: 82 % | |
| After T=20 min. at RT | 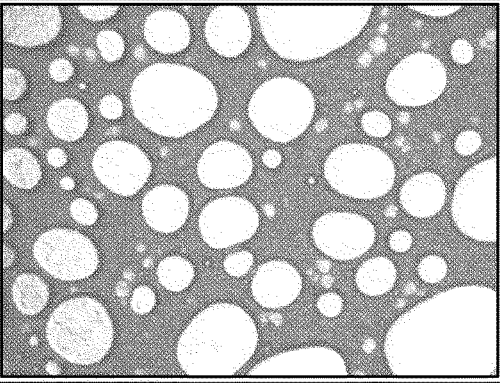 | | 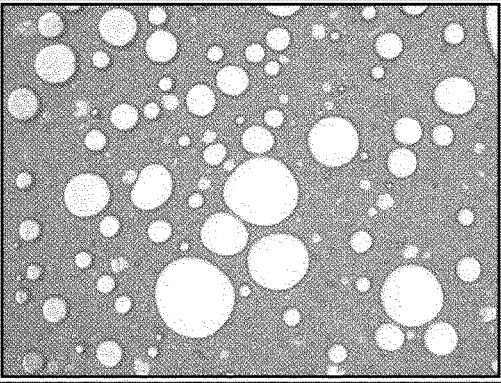 | |
| After T=20 min. at RT | 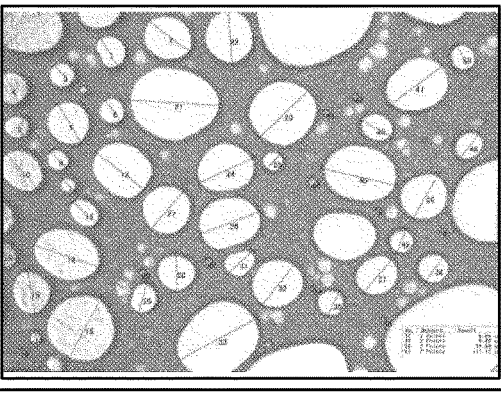 | | 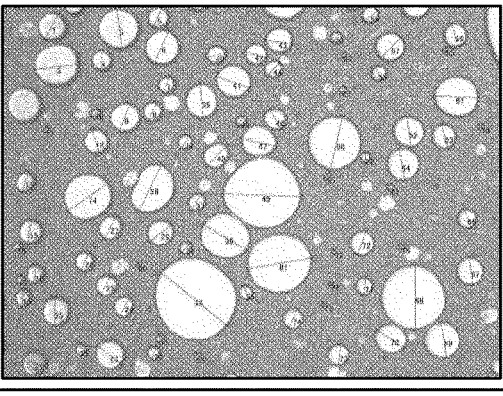 | |
| After T=20 min. at RT | <20 um | 15.7% | <20 um | 13.6% |
| | 20.0-40.0 um | 7.8% | 20.0-40.0 um | 13.6% |
| | 40.1-60.0 um | 3.9% | 40.1-60.0 um | 17.3% |
| | 60.1-100.0 um | 27.5% | 60.1-100.0 um | 35.8% |
| | 100.1-200.0 um | 35.3% | 100.1-200.0 um | 17.3% |
| | 200.1-257 um | 4.2% | 200.1-245 um | 4.2% |
| | ≤60 um: 27 %, ≤100 um: 55 % | | ≤60 um: 45 %, ≤100 um: 80 % | |
FIG. 9B

| | | | | |
|---|---|---|---|---|
| T=0 | <20 um | 31.3% | <20 um | 13.9% |
| | 20.0-40.0 um | 36.7% | 20.0-40.0 um | 21.9% |
| | 40.1-60.0 um | 21.9% | 40.1-60.0 um | 14.9% |
| | 60.1-88.1 um | 10.2% | 60.1-100.0 um | 19.8% |
| | ≤60 um: 90 %, ≤100 um: 100 % | | 100.1-200.0 um | 21.8% |
| | | | 200.1-295 um | 7.9% |
| | | | ≤60 um: 51 %, ≤100 um: 71 % | |
| After T=20 min. at RT | 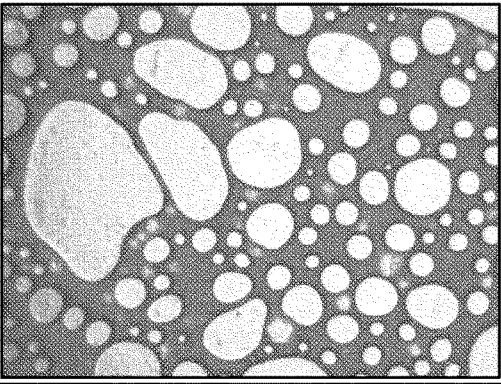 | | 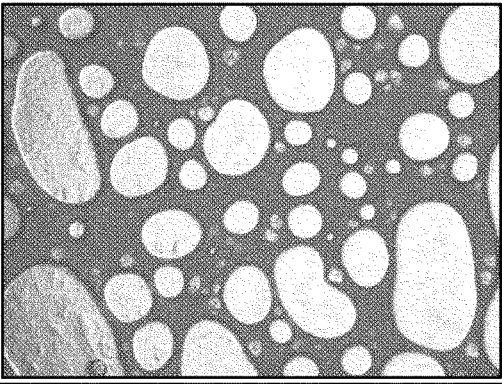 | |
| After T=20 min. at RT | 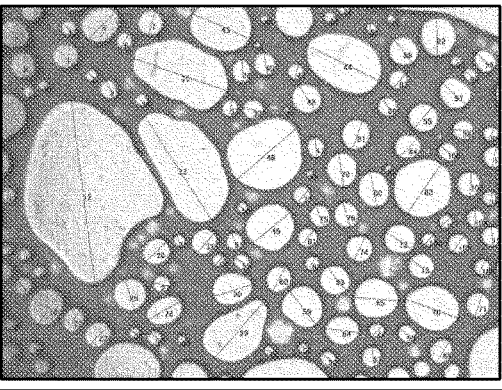 | | 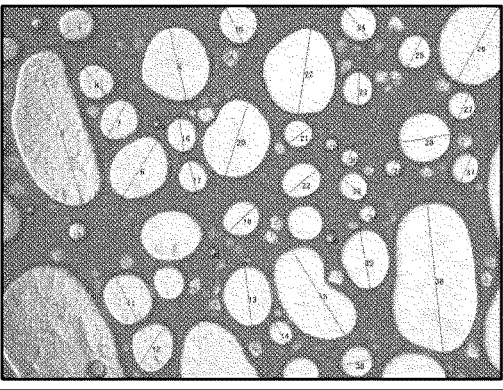 | |
| After T=20 min. at RT | <20 um | 30.3% | <20 um | 15.0% |
| | 20.0-40.0 um | 47.7% | 20.0-40.0 um | 22.5% |
| | 40.1-60.0 um | 12.8% | 40.1-60.0 um | 30.0% |
| | 60.1-100.0 um | 4.6% | 60.1-100.0 um | 17.5% |
| | 100.1-200.0 um | 3.7% | 100.1-197 um | 15.0% |
| | 200.1-229 um | 0.9% | ≤60 um: 68 %, ≤100 um: 85 % | |
| | ≤60 um: 91 %, ≤100 um: 95 % | | | |
FIG. 10B

| Coppertone WB Foaming Lotion SPF 70 | Reddi Wip Original Dairy Whipped Topping |
|---|---|
| 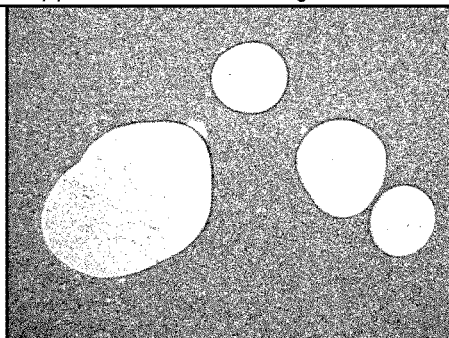 | 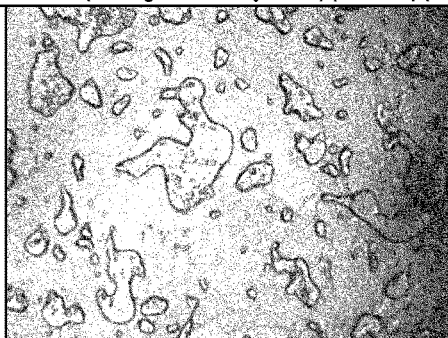 |
| 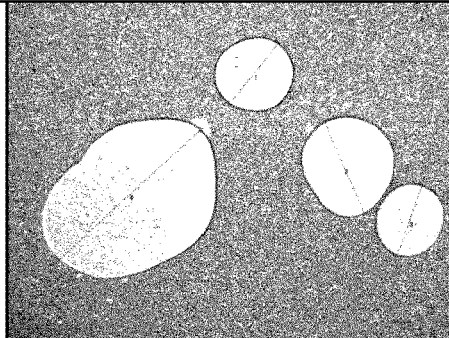 | N/A |
| N/A | N/A |
| N/A | N/A |
FIG. 11 (Cont.)

| | Stored at RT for 3 months |
|---|---|
| "Whipped-foam" Dispensed from Whipped After Sun Lotion | <br>Stable, Rich Creamy Appearance, and Fully Whipped Foam |

| Topical Products in Whipped Products | Wippability | Spreadability or Texture of Resultant Whipped-foams |
|---|---|---|
| Bepanthen® Baby Moisturizer for Extra Sensitive Skin | Yes, 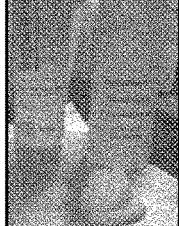 | Very Good, Spread Easily and Smooth |
| Bepanthen® Antiseptic Cream (New Formulation) | Yes,  | Poor (Sticky) |
| Bepanthol® Body Lotion | Yes,  | Very Good, Spread Easily and Smooth |
| Priorin® Shampoo for Hair Loss, Dry and Normal Hair | Yes,  | Good, Spread Easily and Watery |
| Priorin® Shampoo Revitalising Shampoo for Damaged Dry Hair with Millet | Yes,  | Good, Spread Easily and Watery |
| Priorin® Ampules (Liquid) | No,  | Not Applicable |
| Canesten® Cream Clotrimazole 1% | Yes, 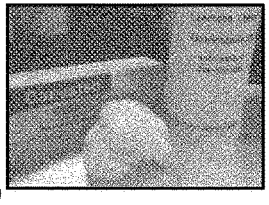 | Very Good, Spread Easily and Smooth |

FIG. 13

| Topical Products in Whipped Products | Initial (T=0) | T=10 minutes |
|---|---|---|
| Bepanthen® Baby Moisturizer for Extra Sensitive Skin |  | 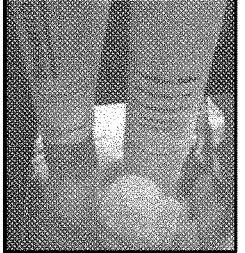 |
| Bepanthen® Antiseptic Cream (New Formulation) |  |  |
| Bepanthol® Body Lotion | 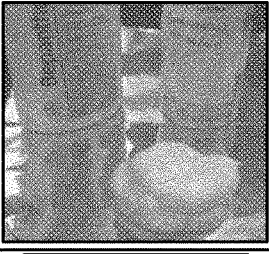 |  T=4 min. |
| Priorin® Shampoo for Hair Loss, Dry and Normal Hair |  | 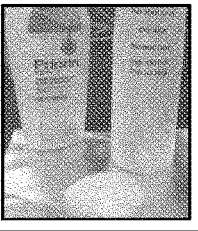 T=30 sec. |
| Priorin® Shampoo Revitalising Shampoo for Damaged Dry Hair with Millet | 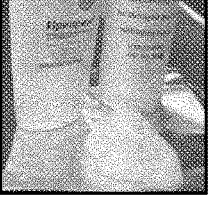 |  T=30 sec. |
| Canesten® Cream Clotrimazole 1% |  | 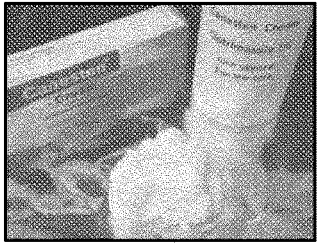 |

FIG. 14

| Run No. | Cut-bag pressure (psi) | Product density (g/L) | Initial | After 20 minutes at RT |
|---|---|---|---|---|
| 1 | 20 | 50 |  |  |
|   |    | 125 |  |  |
|   |    | 200 |  | 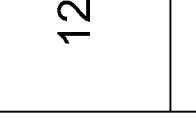 |
FIG. 21

| Run No. | Cut-bag pressure (psi) | Product density (g/L) | Initial | | | After 20 minutes at RT | | |
|---|---|---|---|---|---|---|---|---|
| 1 | 32.5 | 50 | | 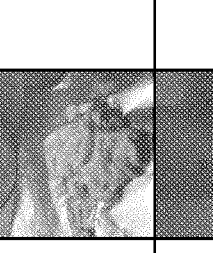 | | | 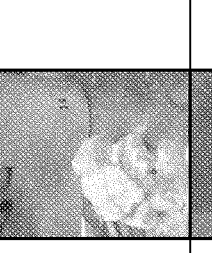 | |
| | | 125 | |  | | | | |
| | | 200 | |  | | | | |
FIG. 22

| Run No. | Cut-bag pressure (psi) | Product density (g/L) | Initial | After 20 minutes at RT |
|---|---|---|---|---|
| 1 | 45 | 50 |  | 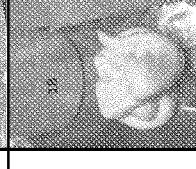 |
|   |   | 125 | 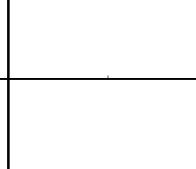 | 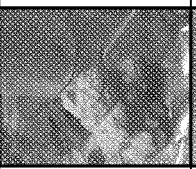 |
|   |   | 200 | 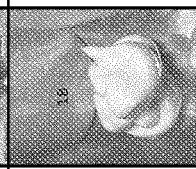 | 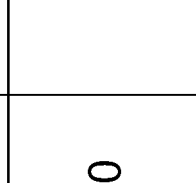 |
FIG. 23

| Run No. | Cut-bag pressure (psi) | Product density (g/L) | Initial | After 20 minutes at RT |
|---|---|---|---|---|
| 1 | 20 | 50 | | |
| | | 125 | | |
| | | 200 | | |

FIG. 24

| Run No. | Cut-bag pressure (psi) | Product density (g/L) | Initial | After 20 minutes at RT |
|---|---|---|---|---|
| 1 | 32.5 | 50 | 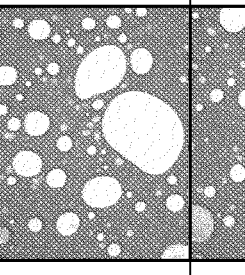 | 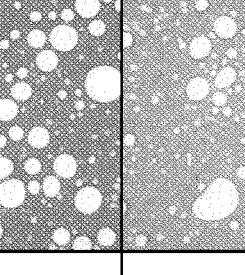 |
| | | 125 | 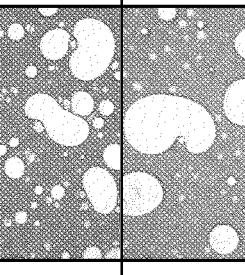 | 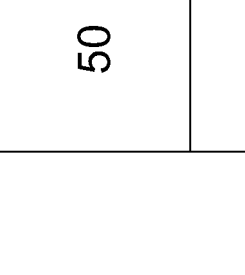 |
| | | 200 | 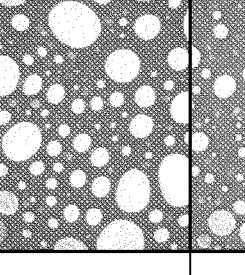 | 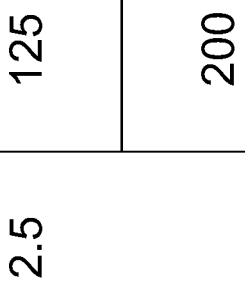 |
FIG. 25

| Run No. | Cut-bag pressure (psi) | Product density (g/L) | Initial | After 20 minutes at RT |
|---|---|---|---|---|
| 1 | 45 | 50 | 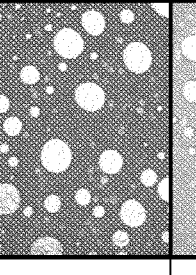 | 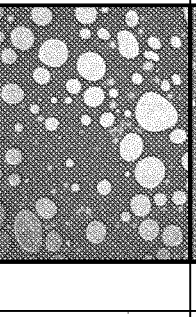 |
|  |  | 125 | 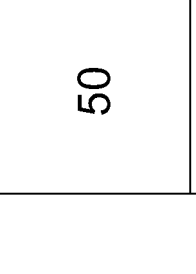 | 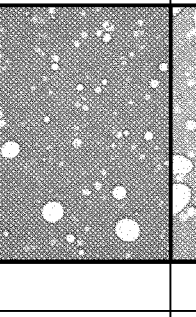 |
|  |  | 200 | 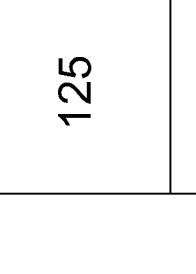 | 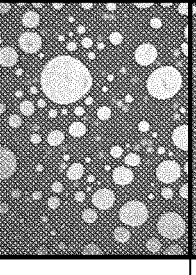 |
FIG. 26

| Run No. | Cut-bag pressure (psi) | Product density (g/L) | "Whipped-foam" dispensed at T=0* | "Whipped-foam" dispensed after T=2 min. at RT |
|---|---|---|---|---|
| 1 | 20 | 50 | 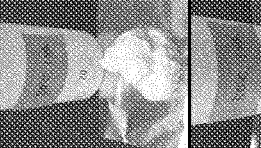 |  |
| | | 125 |  |  |
| | | 200 |  |  |
FIG. 30

| Run No. | Cut-bag pressure (psi) | Product density (g/L) | "Whipped-foam" dispensed at T=0* | "Whipped-foam" dispensed after T=2 min. at RT |
|---|---|---|---|---|
| 1 | 32.5 | 50 | | |
| | | 125 | | |
| | | 200 | | |

FIG. 31

| Run No. | Cut-bag pressure (psi) | Product density (g/L) | "Whipped-foam" dispensed at T=0* | "Whipped-foam" dispensed after T=2 min. at RT |
|---|---|---|---|---|
| 1 | 45 | 50 | 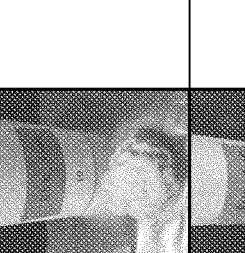 | 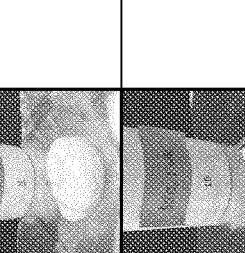 |
|  |  | 125 |  |  |
|  |  | 200 |  |  |
FIG. 32

| Run No. | Cut-bag pressure (psi) | Product density (g/L) | Initial | After 20 minutes at RT |
|---|---|---|---|---|
| 1 | 20 | 50 | 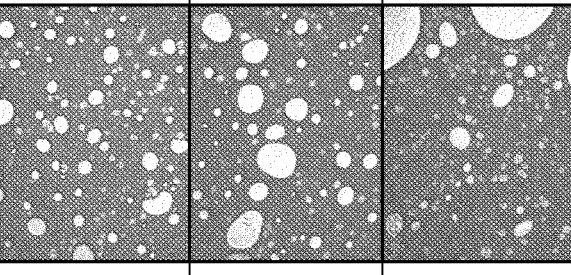 | 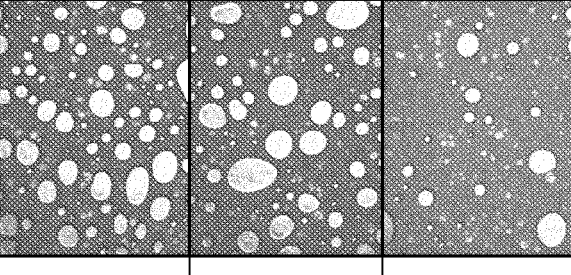 |
|   |    | 125 |   |   |
|   |    | 200 |   |   |
FIG. 33

| Run No. | Cut-bag pressure (psi) | Product density (g/L) | Initial | After 20 minutes at RT |
|---|---|---|---|---|
| 1 | 32.5 | 50 | 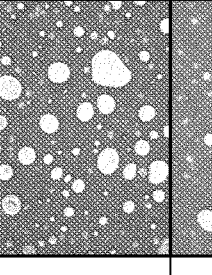 | 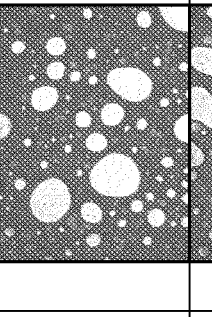 |
| | | 125 | 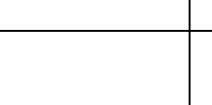 | 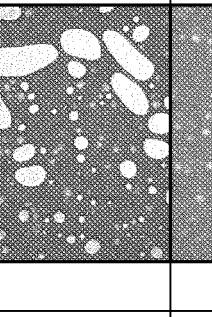 |
| | | 200 |  | 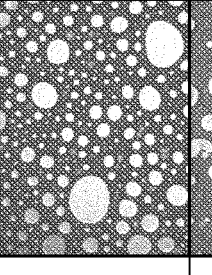 |
FIG. 34

WHIPPED FORMULATIONS

TECHNICAL FIELD

This invention relates to the field of whipped or whippable formulations. More specifically, the invention relates to whipped or whippable formulations, such as for topical application, such as, for example, sunscreen.

BACKGROUND

A key factor for ensuring the effectiveness of a formulation, such as sunscreen, skincare, vitamins for oral administration, woundcare for animals or humans, whip cream, haircare, medical hair and scalp treatments, topical analgesics, skin protection, etc. is end-user compliance and satisfaction.

For example, sunscreen labeling requirements instruct the consumer to "apply liberally", and to "reapply every 80 minutes and after swimming, sweating or toweling dry." Yet, reporting through the Academy of Dermatology website, dermatologists have noted that consumers typically do not apply enough sunscreen. This observed behavior, at least in part, may be because currently available sunscreens are sometimes perceived as heavy, sticky or greasy and can be aesthetically unpleasing during the application process. Also, current sunscreen lotion products tend to become runny or drippy after application. Spray Aerosol sunscreen applications, which atomize low viscosity sunscreen product, can be perceived as not providing even coverage, wasteful from overspray, or difficult to apply in windy situations; they can also be drying to the skin. Ideally, the sunscreen formulation should be easily applied to the skin of the user, and have a good texture and "feel" on the skin of the users.

Likewise, other products, such as for skincare, vitamins for oral administration, wound care for animals or humans, whip cream, for haircare, for medical hair and scalp treatments, for topical analgesics, for skin protection, etc. could benefit from being administered as a whipped product, without the possibility of abuse.

SUMMARY

This disclosure provides a formulation in a package, which may be pressurized. The formulation comprises one or more active agents that is co-mingled (co-processed) with a whipping agent (e.g., a gas propellant; a first gas propellant) prior to being filled under pressure into the package. The whipping agent is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the pressurized package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more gas and/or liquid propellants do not co-mingle with the formulation.

In other aspects, this disclosure provides a method of preparing a whippable formulation, comprising: Filling a formulation comprising one or more active agents co-mingled (co-processed) with a whipping agent (e.g., a gas propellant; a first gas propellant) under pressure into a package, which may be pressurized; wherein the whipping agent is added in sufficient amounts to be dispersed in the formulation. In certain embodiments, the package is under sufficient pressure suitable to maintain the whipping agent dispersed in the formulation. In certain embodiments, the package is under sufficient pressure to expel the formulation as a whipped formulation upon application of external force on the formulation in the package. In certain embodiments, the method is performed under controlled temperature. In certain embodiments, the package maintains at least a minimal amount of pressure until substantially all the formulation in the package is expelled as a whipped formulation. In certain embodiments, the package comprises a pressure generating and maintaining component. In certain embodiments, the component comprises one or more (second) gas and/or liquid propellants; the pressure generating and maintaining component is present in the package in sufficient amounts and pressure to expel the formulation as a whipped formulation upon application of external force on the formulation in the package; and wherein the one or more gas and/or liquid propellants do not co-mingle with the formulation.

In other aspects, this disclosure provides a method of using a formulation that is a whipped formulation product disclosed herein, comprising administering the formulation to a subject (user) in need thereof.

In other aspects, this disclosure provides a package comprising the formulation disclosed herein.

Numerous other aspects are provided in accordance with these and other aspects of the invention. Other features and aspects of the present invention will become more fully apparent from the following detailed description and the appended claims.

BRIEF DESCRIPTION OF THE DRAWINGS

FIG. 1 shows the results for appearance and stay-put-ness features: A whipped sunscreen lotion SPF 30 (Finished Product: Z16-006, Concentrate: Y71-189) versus Kiehl's Lotion Activated Sun Protector™ Water-Light Lotion for Face & Body, SPF 30. FIG. 1A shows appearance of a "whipped-foam" delivered from a whipped sunscreen lotion SPF 30. FIG. 1B shows application of two lotions (Left: a whipped sunscreen lotion SPF 30, Right: Kiehl's sunscreen lotion SPF 30). FIG. 1C shows T=initial; Applied amounts of two lotions are similar. FIG. 1D shows T=10 seconds; Left (a whipped sunscreen lotion SPF 30): no change in appearance and no tendency to run or drip; Right (Kiehl's sunscreen lotion SPF 30): became runny.

FIG. 2 shows results for spreadability and texture features: A whipped Sunscreen Lotion SPF 30 (Finished Product: Z16-006, Concentrate: Y71-189) versus two foaming lotions (the currently marketed Coppertone WaterBABIES® foaming lotion and a mousse-type lotion). FIG. 2A: Texture of a whipped sunscreen lotion SPF 30. FIG. 2B: Spreadability of a whipped sunscreen lotion SPF 30. FIG. 2C: Texture of WaterBABIES® foaming lotion. FIG. 2D: Spreadability of WaterBABIES® foaming lotion. FIG. 2E: Texture of a mousse-type lotion. FIG. 2F: Spreadability of a mousse-type lotion.

FIG. 10 is a photomicrograph (at 500× magnification): Gas Bubble ($N_2O$) distribution in "whipped-foam" delivered from whipped sunscreen lotion SPF 30 (Finished Product: Z16-010, Concentrate: Y71-122), which had been stored at various storage Conditions. FIG. 10A-10D: Z16-010 stored at room temperature (RT) and stored at Freeze (−10° C.)/Thaw (RT) cycles (4 cycles); and 10B: Z16-010 stored at 40° C./20% RH for 3 months and stored at 50° C./75% RH for 1 month.

FIG. 13 shows results for evaluation of whipped delivery systems containing various topical products.

FIG. 14 shows results for the stability of "whipped-foams" delivered from whipped products containing various topical products, at room temperature.

DETAILED DESCRIPTION

Figure 3:
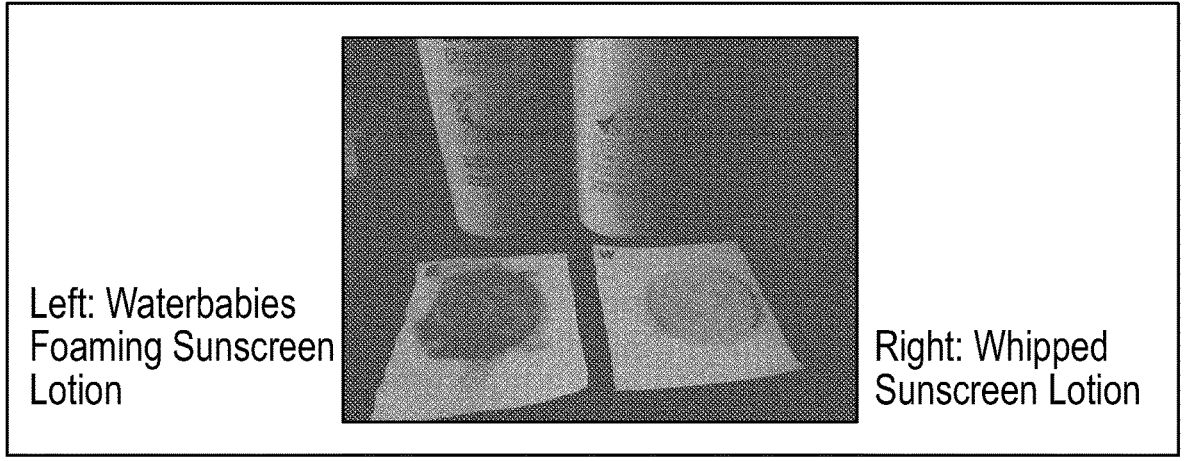
FIG. 3 shows results for the extent of product transfer after application: whipped sunscreen lotion (Finished Product: Z16-014, Concentrate: Y71-159) versus WaterBABIES® foaming sunscreen lotion.

As used herein, the word "a" or "plurality" before a noun represents one or more of the particular noun. For the terms "for example" and "such as," and grammatical equivalences thereof, the phrase "and without limitation" is understood to follow unless explicitly stated otherwise. As used herein, the term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

This disclosure provides a formulation in a package, which may be pressurized. The formulation comprises one or more active agents that is co-mingled (co-processed) with whipping agent (e.g., a gas propellant; a first gas propellant) prior to being filled under pressure (and in certain embodiments under controlled temperature) into the package. The whipping agent is added in sufficient amounts to be dispersed in the formulation. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component comprises one or more (second) gas and/or liquid propellants. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the one or more gas and/or liquid propellants do not co-mingle with the formulation.

In certain embodiments, the formulation is expelled (i.e., dispensed) from the package without shaking the package.

No UV filter substances are used for the foam-boosting of self-foaming.

The disclosed whipped formulation may be referred to herein as whipped formulation, whipped formulation product, whipped product, and the like.

The disclosed whippable formulation may be referred to herein as whippable formulation, whippable formulation product, whippable product, and the like.

A whipped formulation is at one time a whippable formulation.

The term "can" may be used to also mean "package."

A subject may be a human subject (user) or may be an animal subject (user). The terms "subject" and "user" are used interchangeably.

In other aspects, this disclosure provides a method of preparing a whippable formulation, comprising: Filling a formulation comprising one or more active agents co-mingled (co-processed) with whipping agent (e.g., a gas propellant; a first gas propellant) under pressure into a package; and the whipping agent is added in sufficient amounts to be dispersed in the formulation. In certain embodiments, the package is under sufficient pressure suitable to maintain the whipping agent dispersed in the formulation. In certain embodiments, the pressurized package is under sufficient pressure to expel the formulation as a whipped formulation upon application of external force on the formulation in the package. In certain embodiment, the co-processing step is performed under controlled temperature. In certain embodiments, the package maintains at least a minimal amount of pressure until substantially all the formulation in the package is expelled as a whipped formulation. In certain embodiments, the package comprises a pressure generating and maintaining component; in certain embodiments, the component comprises one or more (second) gas and/or liquid propellants; the pressure generating and maintaining component is present in the package in sufficient amounts and pressure to expel the formulation as a whipped formulation upon application of external force on the formulation in the package; and wherein the one or more gas and/or liquid propellant does not co-mingle with the formulation.

In other aspects, this disclosure provides a method of using a formulation that is a whipped formulation product disclosed herein, comprising administering the formulation to a subject (a user) in need thereof. The user may be a human user.

In other aspects, this disclosure provides a package comprising a whippable formulation; the package may be pressurized. The formulation comprises one or more active agents and is co-mingled (co-processed) with whipping agent (e.g., a gas propellant; a first gas propellant) prior to being filled under pressure (and in certain embodiments under controlled temperature) into the package. In certain embodiments, the package maintains at least a minimal amount of pressure until substantially all the formulation in the package is expelled as a whipped formulation. In certain embodiments, the package maintains at least a minimal amount of pressure to maintain the whipping agent dispersed in the formulation. In certain embodiments, the package comprises a pressure generating and maintaining component. In certain embodiments, the component is present in the package in sufficient amounts and pressure to expel the formulation as a whipped formulation upon application of external force on the formulation in the package. In certain embodiments, the amounts of the pressure generating and maintaining component are sufficient to expel substantially all the formulation in the package as a whipped formulation. In certain embodiments, the pressure generating and maintaining component comprises one or more (second) gas and/or liquid propellants which are not co-mingled with the formulation. In certain embodiments, the one or more gas and/or liquid propellants do not co-mingle with the formulation.

In certain embodiments, the disclosed formulations and methods allow for very high levels of inert gas dissolved into the product and effectively held under pressure in a gas-emulsion, preventing unwanted bubble agglomeration, providing for highly uniform product characteristics. The result is a rich, thick "whipped-cream-style" lotion that provides confidence of sunscreen coverage (in the case where the product is a sunscreen), while offering surprisingly fast "rub-in"; while not altering the inherent moisturization and protection properties of the otherwise thick, lipid-rich base formulation.

Whippable products include, in addition to for skincare and suncare (Sunscreen and After Sun care), for example and without limitation:

Category—Class—Whipped Benefit
  Whip Cream—Food—Anti—Abuse
  Peanut Butter—Food—Ease of Application
  Dessert Topping—Food—Ease of Application
  Topical Analgesic—OTC Drug—Improved Absorption
  Burn Cream—Medical Device Rx—Reduced Spread—ability Pain
  Medical Haircare—Hair loss—NDA—Reduced Consumer Complaints—Failure to empty
  Medical Haircare—Scalp treatment—OTC Drug—Improved Delivery/Application
  Petrolatum Gel—OTC Drug—Ease of Application
  Hair Styling Product—Cosmetic—Novel Delivery of Thicker Products
  Diaper Rash Prevention—OTC Drug—Novel Delivery of Thicker Products
  Tooth Whitener—Cosmetic—Better Coverage
  Oral Care—Toothpaste—Cosmetic—Improved Delivery
  Anti-Fungal treatment—OTC/Rx Drug—Reduced Spread-ability Pain/Improved Absorption
  Eye-lid Cleanser—Cosmetic—Novel Delivery
  Psoriasis treatment—Medical Device—Reduced Spread-ability Pain
  Colon-Rectal Treatment—Rx—Improved Drug Delivery and Absorption
  Acne treatment—OTC Drug—Novel Delivery
  Hand Sanitizer—OTC Drug—Formulation Approach
  Natural Deodorant—Cosmetic—Improved Spread-ability
  Shave Prep—Cosmetic—Novel Delivery of Thicker Products
  Wound Care—Medical Device—Novel Delivery of Thicker Products
  Self-Tanner—Cosmetic—Improved Delivery
  Body Moisturizer—Cosmetic—Novel Delivery of Thicker Products
  Lice Treatment—Medical Device/OTC—Novel Delivery of Thicker Products
  Hair Depilatory—OTC Drug—Novel Delivery of Thicker Products
  Anti-Hemorrhagic—Rx/Device—Formulation Compatibility—Non-Flammability—Surgical Application.

Thus, in certain embodiments, the formulation disclosed herein comprise one or more active agents for each of the above formulations.

In certain embodiments, the whipped formulation product is a skincare product, comprising one or more skincare active agents. In certain embodiments, the whipped formulation product is a sunscreen or an after-sun product. In certain embodiments, the whipped formulation product may be an oral dosage form, such as a whipped multi-vitamin product. In certain embodiments, the whipped formulation product may be for woundcare of animals or humans. The whipped formulation may also be, for example, whip cream, for haircare, for medical hair and scalp treatments, topical analgesics, or for skin protection.

In certain embodiments, the formulation further comprises a foaming agent. In certain embodiments, the formulation is for topical application.

In certain embodiments, the pressurized package in which pressure may be generated and/or maintained sufficient for the disclosed formulations is a Bag-on-valve, Piston Can, or Bag-in-Can. In other embodiments, the pressurized package is a mechanical pressure system, including for example, bladder system (such as Exxal Atomos System), which is a PowerContainer system with a rubber bladder around the outside providing pressure to the internal volume. In certain embodiments, springs are used to exert pressure on a bag. In certain other embodiments, hydrostatic pressure is used to exert pressure on a bag.

In certain embodiments, the package is a bag on valve (BOV) pressurized assembly, comprising a two-way fill/dispensing valve, an attached internal high barrier bag affixed to the valve, and rigid container adapted to and capable of holding positive pressure, affixed to the valve. In certain further embodiments, the container is glass, barrier resin, metal/alloy, or another material capable of holding positive pressure. In certain other further embodiments, the container is pre-pressurized with one or more gas and/or liquid propellants prior to filling. In certain further embodiments, the BOV pressurized assembly dispenses the whipped product in a metered dispensing system and not a continuously dosing system. In certain embodiments, the pressurized package can comprise a "pressure generating and maintaining component," which may be a component that generates and/or maintains pressure in the package. It may refer to a chemical component or components which generate pressure, e.g., compressed gas, while inside an enclosed package, device or container (such as a can, for example). Non-limiting examples of such pressure generating and maintaining components are compressed gases/propellants and liquid propellants such as, for example, $CO_2$, propane, butane, isobutane, dimethyl ether, nitrous oxide, nitrogen, oxygen, air, isopentane, hydrofluroolefin, and the like, and suitable blends of such propellants. When a valve is opened by applying an external force, the formulation or ingredients in the device are dispensed in a 'whipped' form or a foamy form. This chemical component or components does not co-mingle with the formulation and may not be dispended with the whipped formulation.

In certain embodiments, pre-pressurizing the package is not needed. In certain embodiments, the package is under Zero Cut Bag Pressure, where gas is present around bag but not pressurized above ambient. Filling the package at ambient pressure, the pressure inside the package would increase as the BOV expands. In certain embodiments, the package comprises an elastomeric tube/bag (akin to a tied off surgical tube). In certain further embodiments, a slight vacuum is applied. In certain embodiments, the package is pressure agnostic, in which the container cannot hold pressure around the bag. In certain embodiments, the package has Negative Cut Bag Pressure, where vacuum is present around the bag but not pressurized above ambient. Other such systems may be used, such as the Sterilflo® system (https://www.hydrasense.ca/en/why-choose-hydrasense/steriflo/).

A "skincare active agent" includes all those materials which are regarded as acceptable for use as active skin-protecting ingredients. A skincare active agent includes, for example and without limitation, skin protectant and/or anti-aging agent. Approval by a regulatory agency may sometimes be required for inclusion of active agents in formulations intended for human contact including but not limited to sunscreen active ingredients or petrolatum, white petrolatum, mineral oil, and dimethicone as skin protectants, as well as agents used as self-tanners or for diaper rash treatment and the like.

Sunscreen active agents which have been or are currently approved for sunscreen use in the United States and elsewhere include, without limitation, paraaminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, octisalate, sulisobenzone, trolamine salicylate, titanium dioxide and zinc oxide, diethanolamine methoxycinnamate, digalloyl trioleate, ethyl dihydroxypropyl PABA, glyceryl aminobenzoate, lawsone with dihydroxy acetone, red petrolatum and the like. Several other sunscreen active ingredients are accepted for use in other countries. Some non-limiting examples from outside the U.S. include Tinosorb M, Tinosorb S, Uvinul T-150, UVA sorb HEB, Uvinul A Plus, Neo Heliopan AP, Neo Heliopan MBC, and the like. It is typical to use combinations of two or more skincare active agents in a formulation. Preferably, the amount of skincare active agent or agents is present in an amount that is consistent with the FDA guidelines. In other embodiments, the amount of skincare active agent or agents is present in an amount that is consistent with other regulatory bodies. The use of a combination of active agents is especially true for sunscreen formulations to achieve higher levels of ultraviolet absorption or to provide useful absorption over a wider range of ultraviolet wavelengths than can be the case with a single active component. Preferably, the sunscreen active agent or agents is present in an amount that is consistent with the FDA sunscreen monograph for sunscreen active agent or agents that are believed to provide the requisite SPF in accordance with the FDA monograph for such sunscreens. Other skin care active agents include sunless tanning active agents, skin protectant active agent emollients, insect repelling agents, and the like. And other agents known in the art.

After Sun product is specially formulated to cool, soothe, calm, and re-hydrate (moisturize) a sunburnt or stressed skin, and to lessen the pain or itch of a sunburnt body. Currently, After Sun products are available as lotion, cream, gel, or spray. The active agents in them are known in the art and any of which is within the scope of this invention. After Sun Actives are ingredients that can provide the following (but not limited) effects on skin: cooling; soothing; calming; re-hydrating (moisturizing); or relief pain/itch associated with sunburn. As an example, and without limitation, an After Sun formulation contains glycerin, panthenol, and aloe barbadensis leaf juice to provide cool and moisturizing effects on skin. As another example, and without limitation, another After Sun formulation contains lidocaine as an active to provide sunburn pain/itch relief.

Other active agents are contemplated. These include, for example and without limitation, sunscreen active agents, After Sun active agents, vitamins, food, etc. Any active agents that can be included as a whipped formulation or a whippable formulation are within the scope of this invention.

In certain embodiments, the package does not display any bearding. Bearding is leakage forced by continued expansion of product still contained within the flow channel of the actuator.

In certain embodiments, the formulation is characterized by microdispersion. In certain embodiments, the formulation is characterized by substantially consistent microvoid after the formulation is expelled from the package. In certain embodiments, the formulation is highly emollient after the formulation is expelled from the package. In certain embodiments, the formulation is readily spreadable and spread evenly after the formulation is expelled from the package.

In certain embodiments, the whipping agent (co-mingled or co-processed with the formulation comprising one or more active agent) is nitrogen, nitrous oxide, carbon dioxide, Argon, air or oxygen. In certain embodiments, the gas propellant in the formulation is between about 0.01% w/w to about 15.00% w/w.

In certain embodiments, the formulation has one or more of characteristics such as little or no wetness after application, having a collapse time of at least 60 seconds, or structurally stable for at least 30 minutes.

In certain embodiments, the formulation is a sunscreen and the one or more active agents include one or more sunscreen active agents.

The disclosed whipped formulation product represents the careful culmination of advancements in formulation, processing, and packaging to deliver a rich, creamy, spreadable, lightweight whipped product for consumer application.

Formulation:

Non-shear thickening emulsion chemistries have been developed to allow for high levels of gas dispersion, physical stability during temperature and pressure extremes, and post-dispensing foam stability. The chemistries have also been customized to allow for the inclusion of consumer-relevant ingredients that may include, for example and without limitation, sun screens, moisturizers, emulsifying agents, film forming agents, thickening agents, skin feel aesthetic enhancers, antifungals, pH adjusters, pro vitamin additives, physical skin barriers, anti-bacterial agents, skin colorants, etc. Other ingredients are also contemplated, such as, without limitation, pain relief additives.

Processing:

In processing of some embodiments, the blended formulation is transferred into a hopper, pressurized and under a controlled temperature, rate of flow and pressure, and is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas and formulation solution, effectively "saturating" the gas into the formulation prior to injection into the package. The gas-infused formulation is then tested for density inline and controlled under pressure and finally injected under pressure into the desired package.

In certain embodiments, the whipping agent is a suitable gas. In certain embodiments, the whipping agent is co-mingled with the formulation prior to filling the formulation into the package.

In certain embodiments, the whipping agent is nitrous oxide gas. In certain embodiments, the nitrous oxide in the formulation is about 0.1% w/w to about 4.0% w/w. In certain embodiments, the nitrous oxide in the formulation is about 0.1% w/w to about 10.0% w/w. In certain embodiments, the Nitrous Oxide in the formulation is about 0.1% w/w to about 1.9% w/w. In certain embodiments, the nitrous oxide in the formulation is about 0.1%, 1.0%, 1.9%, 2.0%, 3.0%, 4.0%, 5.0% w/w to about 6%, 7%, 8%, 9%, 10 w/w. Nitrous oxide has a slight sweet odor that can contribute to fragrance benefits (dual purpose gas benefits).

In certain embodiments, certain other gases can serve as a particularly good whipping agent, as evaluated by the known or estimated Ostwald Coefficients of the blended mixture and gases. Taking into consideration the potential negative effects of co-mingling of the gases with base blended formulation, example being $CO_2$, which can react with water-containing formulas to create carbonic acid and cause shifts in product pH. Alternatively, $CO_2$ can be used as a whipping gas to deliberately modify the pH of the formulation to reach targeted pH levels. Gas propellant or combinations include, without limitation, $CO_2$, argon, isobutane, nitrogen, Argon, air, oxygen, isopentane, other suitable gases, and combination thereof.

In certain embodiments, the whipping agent in the formulation is between about 0.01% w/w to about 15.00% w/w.

In certain embodiments, the whipping agent is an aerosol propellant (including hydrocarbon propellant, compressed gas propellant, soluble gas propellant, and liquefied gas propellant) or a liquid propellant.

In certain embodiments, the whipping agent is a gas propellant. The gas propellant is, for example and without limitation, nitrogen, nitrous oxide, carbon dioxide, Argon, air or oxygen. In certain embodiments, the gas propellant in the formulation is between about 0.01% w/w to about 15.00% w/w.

In certain embodiments, the whipping agent is a liquefied gas propellant, which includes, for example and without limitation, propane, isobutene, N-butane, Dymel 152a, 134a, hydrocarbons, DME (dimethyl ether), 1,3,3, 3-tetrafluoro-propene, and HFCs (1,1,1, 2-tetrafluoroethane).

In certain embodiments, the whipping agent is a hydrocarbon propellant, which includes, for example and without limitation, methane, ethane, propane, butanes, and pentanes.

Unless otherwise noted or otherwise clear in context to a person of ordinary skill in the art, all % herein are weight to weight (w/w).

Packaging:

In certain embodiments, the pressure in the pressurized package is initially between about 15 psig to about 60 psig. In certain embodiments, the final pressure in the pressurized package is between about 80 psig to about 160 psig. In certain embodiments, the pressure initially is about 40 psig to 45 psig. In certain embodiments, the final pressure is about 110 psig to 120 psig.

In certain embodiments, the package is a Bag on Valve (BOV) pressurized assembly, comprising a two way fill/dispensing valve, an attached internal high barrier bag (affixed to valve), and rigid container capable of holding positive pressure (affixed to the valve). The container may be glass, barrier resin, metal/alloy, or another material capable of holding positive pressure. The container may be "pre-pressurized" with a combination of gaseous and/or liquid propellants prior to filling, with internal pressure expected to build as the internal volume is displaced during pressurized BOV filling.

The Bag on Valve assembly and accompanying "air gap" created between bag and the pressurized rigid container help to create an insulated barrier between the formulation and the user environment. This isolative barrier is helpful to moderate the temperature swings that might be experienced when taking this product from an ambient (indoor) location to a cooler or warmer environment, such as into the sun or into vehicles located in low/high temperature environments. This barrier helps to buffer formulation temperature change and help the formulation deliver a more consistent product experience (lower temperatures can form more rigid foam structures and high temperatures can cause weaker foam structures). This feature can be particularly useful for products formulated with lower melt point foam-formers, intended for use in elevated temperature environments.

Bag on Valve delivery systems differ from traditional aerosol delivery systems in at least the following ways: Aerosols require propellant gases to be co-joined or co-mingled into the base formulation, as would be the case in single or multiphase system. These systems use the propellant gas to both expel the product and as a foaming and/or particle breakup agent. By contrast, a Bag on Valve system includes the use of a bag within a metal can. The bag is in direct contact with the single-phase formulation and is expelled by application of pressure to the outside of the bag. As such, the propellant gas inside the package never comes in contact with the product. Particle breakup or foaming can be accomplished through the dispensing actuator design and/or through the inclusion of a secondary gas within the formulation.

This BOV design has a several distinct benefits over traditional aerosol systems including without limitation:
  Very high levels of product evacuation (>99% or even greater than 99.5%)
  The ability to dispense formulas without the need to comingle with the propellant gas ("pure" formulation concentrate)
  The ability to include gases within the formation as a foaming or particle breakup mechanism that might not serve as a sufficient propellant system
  The ability to use two different gases within the system, one optimized as a propellant and one optimized as a foaming, forming (i.e., dispensing the formulation on a user's hand in a specific, desired form) or particle breakup additive.

For example, in certain embodiments, nitrous oxide is used as a whipping agent without allowing "free gas" to be expelled and potentially abused. By contrast, whipped cream packaging which is sold in a traditional aerosol permits the user the ability to release and potentially abuse the gas propellant/whipping agent.

The pressure generating and maintaining component may be a gas, such as gaseous propellant, a liquid, such as a liquid propellant or a blend of gas and liquid. As used herein, a gaseous propellant may also be a compressed gas, such as $CO_2$, nitrous oxide and the like. As used herein, a liquid propellant may also be a liquefied gas, such as isobutane and the like.

The pressure generating and maintaining component can be formulated inside the device in a variety of ways, depending upon the nature of the component or components that form the pressure generating and maintaining component. The vehicle, while acting as pressure-generator, may be a gas, even though it may have been packaged as, for example, a gas, a liquid or a solid. Non-limiting examples of the gas are carbon dioxide ($CO_2$), nitrous oxide ($N_2O$) and the like. Thus, for example, if the vehicle is carbon dioxide, the carbon dioxide can be 'derived' inside the sealed pressurized container in several ways. For example, the gas could be pumped into the container, or it could be added into the ingredients as "dry ice", or it could be derived or generated in situ via the chemical reaction of a suitable base with a suitable acid. In the case of "pumped in" or "dry ice", the gas is already present as $CO_2$. In the case of generation in situ via the chemical reaction of a base with an acid, the gas is generated when the acid and the base mix.

If generating the gas by chemical reaction between a base and an acid, non-limiting examples of suitable bases include sodium bicarbonate, sodium carbonate, potassium bicarbonate, potassium carbonate and the like. Non-limiting examples of suitable acids include acetic acid, citric acid and the like. Sodium bicarbonate with citric acid is a suitable combination. Because the components are being combined inside of the sealed container (device), the gas produced during the reaction is trapped which pressurizes the container.

One advantage of the inventive system is that the gas introduced or produced may be non-flammable.

In certain embodiments, the whipped formulation product is characterized by microdispersion. In certain embodiments, the whipped formulation product is characterized by substantially consistent microvoid.

In certain embodiments, the whipped formulation product comprises at least one recognized skincare active agent.

In certain embodiments, the whipped formulation is a sunscreen formulation comprising at least one sunscreen active agent.

In certain embodiments, the whipped formulation product further comprises other ingredients, such as, for example and without limitation, one or more fatty alcohols-selected from, for example and without limitation, cetyl alcohol, stearyl alcohol, myristyl alcohol, hydroxystearyl alcohol, oleyl alcohol, isostearyl alcohol, lauryl alcohol, hexadecyl alcohol, ricinoleyl alcohol, behenyl alcohol (lanette 22), erucyl alcohol and 2-octyl-dodecanol. In certain embodiments, the whipped formulation is an after-sun lotion (contains Cetyl alcohol) but optionally without any added behenyl alcohol.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In one embodiment, the disclosed whipped product formulation dispenses in a continuous stream when an external pressure is applied to the device, such as by depressing the valve/actuator, thereby eliminating the need to squeeze and shake the formulation out of a bottle or tube.

In another embodiment, the disclosed whipped product in its device (package) operates as a "one-touch" delivery system; in such system, the user will hold down the actuator until the desired amount of formulation is dispensed.

In another embodiment, the disclosed whipped product in its package offers a continuous delivery system for an application, such as, for example and without limitation, skincare applications and suncare applications. Traditionally, "continuous delivery" is typically offered as a spray product and has been very successful due to the ease and speed that it provides for sunscreen application. Many consumers, however, prefer lotions/gels over sprays and would benefit from a continuous delivery mechanism. The present invention offers such an advantage.

The disclosed whipped formulation product can be used for any application that would benefit from such product, including, for example and without limitation, skincare, sunscreen, After Sun care, vitamins, woundcare, etc. For each application, the formulation needs to comprise the corresponding active agent(s) and may further comprise other appropriate ingredients.

The disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sun-screen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

The term "emulsion" identifies oil-in-water (o/w) or water-in-oil (w/o) type dispersion formulations intended for application to the skin, and air emulsion. Such dispersion formulations include, for example and without limitation, lotions and creams providing cosmetic or therapeutic benefits.

The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, food, vitamins, etc., depending on the intended uses for the formulations.

In certain embodiments, the whipped formulation product comprises one or more of a thickening agent and/or an emulsifying agent.

Suitable emulsifiers are those known in the art for producing oil-in-water type emulsions. An aqueous external phase is preferred by many people for skin contact, since it is not as likely to produce an oily or greasy sensation when it is being applied, as is an emulsion having an oil external phase. The typical oil-in-water emulsifier has a hydrophilic-lipophilic balance (frequently abbreviated as "HLB") value greater than about 9, as is well known in the art; however, this "rule" is known to have numerous exceptions. The chosen emulsifier, depending upon its chemical nature, will be a component of either the oil or aqueous phase or both, and assists with both the formation and the maintenance, or stability, of the emulsion.

Non-limiting examples of suitable emulsifiers or surfactants include pharmaceutically acceptable, non-toxic, non-ionic, anionic and/or cationic surfactants. Examples of suitable non-ionic surfactants include, for example and without limitation, glycerol fatty acid esters such as glycerol monostearate, glycol fatty acid esters such as propylene glycol monostearate, polyhydric alcohol fatty acid esters such as polyethylene glycol (400) monooleate, polyoxyethylene fatty acid esters such as polyoxyethylene (40) stearate, polyoxyethylene fatty alcohol ethers such as polyoxyethylene (20) stearyl ether, polyoxyethylene sorbitan fatty acid esters such as polyoxyethylene sorbitan monostearate, sorbitan esters such as sorbitan monostearate, alkyl glycosides such as cetearyl glucoside, fatty acid ethanolamides and their derivatives such as the diethanolamide of stearic acid, Prolipid and the like. An example of a suitable Prolipid is Prolipid 141 which lists behenyl alcohol, glyceryl stearate, palmitic acid, stearic acid, myristyl alcohol, lauryl alcohol, cetyl alcohol and lecithin as its ingredients in its Formula Data Sheet. Examples of suitable anionic surfactants are soaps including, for example and without limitation, alkali soaps, such as sodium, potassium and ammonium salts of aliphatic carboxylic acids, usually fatty acids, such as sodium stearate. Organic amine soaps include, for example and without limitation, organic amine salts of aliphatic carboxylic acids, usually fatty acids, such as triethanolamine stearate. Metallic soaps include salts of polyvalent metals and aliphatic carboxylic acids, usually fatty acids, such as aluminum stearate. Other classes of suitable anionic surfactants include, for example and without limitation, sulfated fatty acid alcohols such as sodium lauryl sulfate, sulfated oils such as the sulfuric ester of ricinoleic acid disodium salt, and sulfonated compounds such as alkyl sultanates including sodium cetane sulfonate, amide sulfonates such as sodium N-methyl-N-oleyl laurate, sulfonated dibasic acid esters such as sodium dioctyl sulfosuccinate, alkyl aryl sulfonates such as sodium dodecylbenzene sulfonate, alkyl naphthalene sulfonates such a sodium isopropyl naphthalene sulfonate, petroleum sultanate such as aryl naphthalene with alkyl substitutes. Examples of suitable cationic surfactants include, for example and without limitation, amine salts such as octadecyl ammonium chloride, quaternary ammonium compounds such as benzalkonium chloride. Non-limiting examples of emulsifiers include a mixture of cetearyl glucoside and cetearyl alcohol, available under the trade name Emulgade PL68/50 from Henkel KGaA, and PEG 30 dipolyhydroxy stearate, available under the trade name Arlacel 135 from ICI. Also preferred are various $C_{12-15}$, $C_{12-16}$ and $C_{14-15}$ alcohols available from various manufacturers, and Ceteareth 2, 10, 18, 22, Ceteth-1 and 20, cetyl dimethicone copolyol, and cetyl phosphate, glyceryl stearate, Oleth 3 and 10, polyglyceryl 3 methylglucose dis-tearate sorbitan isostearate, steareth 2, 10, and/or 20.

Other suitable emulsifiers are those known in the art for producing water-in-oil type emulsions. Non-limiting examples of some suitable water-in-oil emulsions include, for example and without limitation, SIMALINE WO (PEG-30 Dipolyhydroxystearate; available from Seppic), FLUIDANOV 20× (Octyldodecanol & Octyldodecyl Xyloside; available from Seppic), ES-5300 (Lauryl PEG-10 Tris(trimethylsiloxy) silylethyl Dimethicone; available from Dow Corning), Abil EM90 (Cetyl PEG/PPG-10/1 Dimethicone; available from Evonik) and Abil WE09 (Polyglyceryl-4 Isostearate and Cetyl PEG/PPG-10/1 Dimethicone and Hexyl Laurate; available from Evonik). The typical water-in-oil emulsifier has a HLB value of about 4 to about 6, however, this "rule" is also known to have numerous exceptions.

It may be advantageous to incorporate thickening agents, such as, for instance, Avicel RC-591, Carbopol Ultrez, Carbopol ETD 2001, available from the B. F. Goodrich Co, Abil Wax 9801, a surfactant available from Evonik, Alginic Acid, available from Kelco, cellulose gum, available from TIC Gums, ammonium acrylates copolymer, ammonium polyacryloyl dimethyl taurate, bentonite available from Southern Clay, guar hydroxpropyltrimonium chloride available from Henkel, hydroxy propylprocellulose available from Aqualon, magnesium aluminum silicate, available from Salomon, potassium alginate available from Kelco, beeswax available from Strah & Pitsch, and behenyl alcohol available from Nikko.

Insect repelling components are also a desirable ingredient in certain skincare and sunscreen formulations, if the formulations are to be used by persons engaged in outdoor activities. The most widely used insect repelling agent for personal care products is N, N-Diethyl-m-toluamide, frequently called "DEET" and available in the form of a concentrate containing at least about 95 percent DEET. Other synthetic chemical repellents include, for example and without limitation, dimethyl phthalate, ethyl hexanediol, indalone, di-n-propylisocinchoronate, bicycloheptene, dicarboximide, IR3535 (3-[N-Butyl-N-acetyl]-aminopropionic acid, ethyl ester; available from Merck KGaA)) and tetrahydrofuraldehyde. Certain plant-derived materials also have insect repellent activity, including citronella oil and other sources of citronella (including lemon grass oil), limonene, rosemary oil and *eucalyptus* oil. Choice of an insect repellent for incorporation into the skincare or sunscreen emulsion will frequently be influenced by the odor of the repellent. The amount of repellent agent used will depend upon the choice of agent; DEET is useful at high concentrations, such as up to about 15 percent or more, while some of the plant-derived substances are typically used in much lower amounts, such as 0.1 percent or less.

The disclosed formulation/formulations may contain a wide range of additional, optional components. The CTFA Cosmetic Ingredient Handbook, Seventh Edition, 1997, the Eighth Edition, 2000, and the Personal Care Council website (http://www.personalcarecouncil.org/), describe a wide variety of cosmetic and pharmaceutical ingredients commonly used in skin care formulations, which are suitable for use in the formulations of the present invention. Examples of these functional classes disclosed in these references include, for example and without limitation: absorbents, abrasives, anti-caking agents, anti-foaming agents, antioxidants, binders, biological additives, buffering agents, bulking agents, chelating agents, chemical additives, colorants, cosmetic astringents, cosmetic biocides, cryoprotectants, film stabilizers, denaturants, drug astringents, external analgesics, film formers, fragrance components, humectants, pacifying agents, pH adjusters, plasticizers, preservatives, propellants, reducing agents, skin bleaching agents, skin-conditioning agents (emollients, humectants, miscellaneous, and occlusive), skin protectants, solvents, SPF enhancers/boosters, foam boosters, hydrotropes, solubilizing agents, suspending agents (nonsurfactant), sunscreen agents, ultraviolet light absorbers, water-proofing agents, and viscosity increasing agents (aqueous and nonaqueous).

An emollient is a substance which helps to smooth and soften the skin, and may also reduce its roughness, cracking or irritation. Non-limiting examples of suitable emollients include, for example and without limitation, mineral oil having a viscosity in the range of 50 to 500 centipoise (cps), lanolin oil, coconut oil, cocoa butter, olive oil, almond oil, macadamia nut oil, aloe extracts such as aloe vera lipoquinone, synthetic jojoba oils, natural Sonora jojoba oils, safflower oil, corn oil, liquid lanolin, cottonseed oil and peanut oil. Preferably, the emollient is a cocoglyceride, which is a mixture of mono, di and triglycerides of cocoa oil, sold under the trade name of Myritol 331 from Henkel KGaA, or Dicaprylyl Ether available under the trade name Cetiol OE from Henkel KGaA or a $C_{12}$-$C_{15}$ Alkyl Benzoate sold under the trade name Finsolv IN from Finetex. Another suitable emollient is DC 200 Fluid 350, a silicone fluid, available from Dow Corning Corp. One or more emollients may be present ranging in amounts from about 1 percent to about 10 percent by weight, preferably about 5 percent by weight.

Other suitable emollients include, for example and without limitation, squalane, castor oil, polybutene, sweet almond oil, avocado oil, calophyllum oil, ricin oil, vitamin E acetate, olive oil, silicone oils such as dimethylopolysiloxane and cyclomethicone, linotenic alcohol, oleyl alcohol, the oil of cereal germs such as the oil of wheat germ, isopropyl palmitate, octyl palmitate, isopropyl myristate, hexadecyl stearate, butyl stearate, decyl oleate, acetyl glycerides, the octanoates and benzoates of ($C_{12}$-$C_{15}$) alcohols, the octanoates and decanoates of alcohols and poly-alcohols such as those of glycol and glyceryl, ricinoleates esters such as isopropyl adipate, hexyl laurate and octyl dodecanoate, dicaprylyl maleate, hydrogenated vegetable oil, phenyltrimethicone, jojoba oil and aloe vera extract.

Other suitable emollients which are solids or semi-solids at ambient temperatures may be used. Such solid or semi-solid cosmetic emollients include, for example and without limitation, glyceryl dilaurate, hydrogenated lanolin, hydroxylated lanolin, acetylated lanolin, petrolatum, isopropyl lanolate, butyl myristate, cetyl myristate, myristyl myristate, myristyl lactate, cetyl alcohol, isostearyl alcohol and isocetyl lanolate. One or more of these emollients can be optionally included in the formulation.

The whipped formulations can further comprise skin protectant active agents. Suitable examples include, for example and without limitation, (with preferred weight percent ranges), Allantoin (0.5 to 2 percent); Aluminum hydroxide gel (0.15 to 5 percent), Calamine (1 to 25 percent); Cocoa butter (greater than 50 percent); Cod liver oil (5 to 14 percent); Dimethicone (1 to 30 percent); Glycerin (20 to 45 percent); Hard fat (greater than 50 percent); Kaolin (4 to 20 percent); Lanolin (12.5 to 50 percent); Mineral oil (greater than 50 percent); Petrolatum (greater than 30 percent); Topical starch (10 to 98 percent); White petrolatum (greater than 30 percent); Zinc acetate (0.1 to 2 percent); Zinc carbonate (0.2 to 2 percent); and Zinc oxide (1 to 25 percent). Additional skin protectant active agents may include Colloidal oatmeal or Sodium bicarbonate.

Water is employed in amounts effective to form the emulsion. It is generally preferred to use water which has been purified by processes such as deionization or reverse osmosis, to improve the batch-to-batch formulation inconsistencies which can be caused by dissolved solids in the water supply. The amount of water in the emulsion or formulation can range from about 15 percent to 95 weight percent.

A humectant is a moistening agent that promotes retention of water due to its hygroscopic properties. Suitable humectants include, for example and without limitation, glycerin, polymeric glycols such as poly-ethylene glycol and polypropylene glycol, mannitol and sorbitol. Preferably, the humectant is glycerin, Sorbitol 70% USP or polyethylene glycol 400, NF. More preferably, the humectant is glycerin. One or more humectants can optionally be included in the formulation in amounts from about 1 percent to about 10 percent by weight, preferably about 5 percent by weight. Other suitable humectants include, inter alia, fructose, glucose, lactic acid, PCA, potassium lactate and PCA, propylene glycol, sodium lactate, PCA, and etc.

A dry-feel modifier is an agent which when added to an emulsion, imparts a "dry feel" to the skin when the emulsion dries. Dry feel modifiers can include, for example and without limitation, talc, kaolin, chalk, starches, zinc oxide, silicone fluids, inorganic salts such as barium sulfate, surface treated silica, precipitated silica, fumed silica such as an Aerosil (silica) available from Evonik Industries, DryFlo starch (aluminum starch octenylsucinate available from Akzo Nobel), and/or an epichlorohydrin cross-linked glyceryl starch, available from Ingredion, Inc. Bridgewater, NJ, under the current tradename of Vulca 90 starch.

The disclosed formulation may additionally contain waterproofing agents. A waterproofing or water resistance agent is a hydrophobic material that imparts film forming and waterproofing characteristics to an emulsion. A waterproofing agent that can be used, for example and without limitation, is a copolymer of vinyl pyrollidone and eicosene and dodecane monomers such as the Ganex V 220, Ganex P-904 LC, and Ganex V 216 Polymers, respectively, available from Ashland Inc. Still other suitable waterproofing agents include poly alfa olefin polymers, such as Performa V 825 available from New Phase Technologies and polyanhydride resin No. 18 available under the trade name PA-18 from Chevron. Additional examples of waterproofing agents are polyurethane polymers. Some such polymers are described, for example, in U.S. Pat. No. 7,097,828.

An antimicrobial preservative may be part of the disclosed formulation. An antimicrobial preservative is a substance or preparation which destroys, prevents or inhibits the proliferation of, microorganisms in the skincare formulation, and which may also offer protection from oxidation. Preservatives are frequently used to make self-sterilizing, aqueous based products such as emulsions. This is done to prevent the development of microorganisms that may grow in the product during the manufacture and distribution of the product and/or during use by consumers, who may further inadvertently contaminate the products during normal use. Typical preservatives include, for example and without limitation, the lower alkyl esters of para-hydroxybenzoates (parabens), especially methylparaben, propylparaben, isobutylparaben and mixtures thereof, benzyl alcohol, phenyl ethyl alcohol and benzoic acid. The preferred preservative is available under the trade name of Germaben II from Sutton or a combination of chlorphenesin and benzyl alcohol. One or more antimicrobial preservatives can optionally be included in an amount ranging from about 0.001 to about 10 weight percent, preferably about 0.05 to about 1 percent.

An antioxidant may be part of the disclosed formulation. An antioxidant is a natural or synthetic substance added to the sunscreen to protect from or delay its deterioration due to the action of oxygen in the air (oxidation) and to protect the skin from sun damage. Antioxidants prevent oxidative deterioration which may lead to the generation of rancidity and nonenzymatic browning reaction products. Typical suitable antioxidants include, for example and without limitation, propyl, octyl and dodecyl esters of gallic acid, butylated hydroxyanisole (BHA, usually purchased as a mixture of ortho and meta isomers), butylated hydroxytoluene (BHT), nordihydroguaiaretic acid, Oxynex (Oxynex ST liquid is a mixture of diethylhexyl syringyliden-emalonate and caprylic/capric triglyceride), Vitamin A, Vitamin E and Vitamin C. One or more antioxidants can optionally be included in the formulation in an amount ranging from about 0.001 to about 5 weight percent, preferably about 0.01 to about 0.5 percent.

Chelating agents may be part of the disclosed formulation. Chelating agents are substances used to chelate or bind metallic ions, such as with a heterocyclic ring structure so that the ion is held by chemical bonds from each of the participating rings. Suitable chelating agents include, for example and without limitation, ethylene diaminetetraacetic acid (EDTA), EDTA disodium, calcium disodium edetate, EDTA trisodium, citric acid, EDTA tetrasodium and EDTA dipotassium. One or more chelating agents can optionally be included in the formulation in amounts ranging from about 0.001 to about 0.2 weight, percent preferably about 0.01% weight percent.

The disclosed formulation may include foam stabilizers or foam stabilizing agents. There are many examples of such agents and means to achieve foam stability. Non-limiting examples of suitable foam stabilizers include, for example and without limitation, the Avicels, Capmul S12L, Capmul S18L, Amilite GCK-12, Amadol CMA-2, Ampholak 7 CX-C, Ampholak X C0-30, Polyox WSR N-10, Amaranth S, Foam-Coll 5, Blanose 12M31XP, Genu carrageenan, Avanel S150CG and others. Avicel is an example that can be used in the formulation. For example, Avicel RC-591 is a mixture of cellulose gum and microcrystalline cellulose. Some foam stabilizers also help improve long term high temperature stability.

Fragrances are aromatic substances which can impart an aesthetically pleasing aroma to the skincare or sunscreen formulation and may be part of the disclosed formulation. Typical fragrances include, for example and without limitation, aromatic materials extracted from botanical sources (i.e., rose petals, gardenia blossoms, jasmine flowers, etc.) which can be used alone or in any combination to create essential oils. Alternatively, alcoholic extracts may be prepared for compounding fragrances. However, due to the relatively high costs of obtaining fragrances from natural substances, the modern trend is to use synthetically prepared fragrances, particularly in high-volume products. Both types are considered to be within the scope of the present invention.

A pH modifier may be part of the disclosed formulation. A pH modifier is a compound that will adjust the pH of a formulation to a lower, e.g., more acidic pH value, or to a higher, e.g., more basic pH value. The disclosed formulations may contain such pH modifiers as is necessary.

In some embodiments, an SPF enhancer or booster, including styrene/acrylates copolymer (such as Sunspheres PGL, commercially available from Dow Chemical), and/or skin active agents, and/or anti-oxidants, may be optionally added to the formulation.

The disclosed formulation may be used as an After Sun formulation. As used herein, an After Sun emulsion formulation is defined as a formulation that can be administered after a user has been in the sun for any amount of time and is a formulation that provides a soothing or healing effect that is pleasant to the user. Such a formulation can contain, for instance, aloe vera, vitamins A and E, cooling agents, moisturizers, redness-reducing agents and the like.

The present formulation may be used as self-tanning formulation or for sunless tanning. As used herein, the term "sunless-tanning" or "self-tanning formulations" refer to formulations which, when applied to human skin, impart thereto an appearance similar to that achieved by exposing the skin to natural or artificial sunlight. Examples of sunless tanning active agents are described in U.S. Pat. Nos. 6,482, 397, 6,261,541, and 6,231, 837. Such sunless tanning compositions typically comprise, in addition to an artificial tanning effective amount of a self-tanning agent, effective amounts of a formulation coloring agent and a cosmetically acceptable carrier adapted for topical application to human skin. The self-tanning agents can also include those formulations generally accepted in the art for application to human skin, and which, when so applied, react therein with amino acids so as to form pigmented products. Such reactions give the skin a brown appearance, similar to the color obtained upon exposing it to sunlight for periods of time sufficient to tan the skin. Suitable self-tanning agents include, without limitation, alpha-hydroxy aldehydes and ketones, glyceraldehyde and related alcohol aldehydes, various indoles, imidazoles and derivatives thereof, and various approved pigmentation agents. Presently preferred herein as self-tanning agents are the alpha-hydroxy aldehydes and ketones. Most preferably, the self-tanning agent is dihydroxyacetone ("DHA"). Other suitable self-tanning agents include, without limitation, methyl glyoxal, glycerol aldehyde, erythrulose, alloxan, 2,3-dihydrox-ysuccindialdehyde, 2, 3-dimethoxysuccindialdehyde, 2-amino-3-hydroxy-succindialdehyde and 2-benzylamino-3-hydroxysuccindialdehyde.

The disclosed whipped formulation product has been developed, in part, to offer consumers a unique and better way to apply topical products such as sunscreen and skin creams to themselves and others.

One advantage of the disclosed whipped formulation product is during dispensing the density of the formulation contained within the package drops measurably, in one example dropping from a density roughly equal to 1.0 g/ml to 0.15-0.18 g/ml post evacuation. The resulting dispensed product represents a whipped product (a foam) of substantial rigidity and body, slow to collapse under ambient and elevated temperature conditions but easy to "break" upon physical manipulation, as for example during rubbing. This allows for a more "controlled" and even dispersal/spreading/distribution of product as compared to the initial "unwhipped" presentation of the formulation.

Another advantage of the disclosed whipped product arises from the ability to contain such a large "dispensed volume" in such a condensed package format. The volume comparison between "straight" (un-whipped) and "whipped" formulation is represented in roughly a 1:5 to 1:6 ratio, allowing for a far more consumer friendly and portable package size/format for such a large volume of dispensed product.

In certain embodiments, the disclosed whipped formulation product can allow for more control of spread over body. In certain embodiments, the disclosed whipped formulation product provides a more rigid "push" providing enhanced tactile response. In certain embodiments, the disclosed whipped formulation product is described as "thicker, creamier, and more volume," "lighter during application." In certain embodiments, the disclosed whipped formulation product allows for more control as to "heaviness" of application. In certain embodiments, the disclosed whipped formulation product provides for faster application due to perceived fast absorption.

In certain embodiments, the disclosed whipped formulation product allows for high levels of product evacuation, particularly for viscous products as compared to traditional non-pressurized emulsion packaging. In certain embodiments, the disclosed whipped formulation product with its pressured system allows for elevated levels of gas to be saturated into formulation, beyond what ambient would normally allow, which can increase whipping potential (lower resulting dispensed densities) and reduce sputtering that can be caused by saturating high levels of gas into formulation but failing to provide adequate pressure to contain the saturated gas. In certain embodiments, the disclosed whipped formulation product results in reduced corrosion potential by separating the formulation from the rigid, pressurized container (if metal) by containing the formulation in the internal bag. In certain embodiments, the disclosed whipped formulation product can have its gas propellant, pressure, and gas dispersion customized for each formulation. Whereas oil and water emulsions are particularly well suited for specific gases, liquid propellants can provide much larger bubble structures. BOV dispensing mechanism allows for co-blending of the various types of liquid and gas-phase propellant allowing to dispense whipped products without substantially altering temperature or potentially induce a cooling effect due to phase change energy absorption.

The disclosed whipped product is a light and spreadable formulation and thus may be particularly well suited for sensitive or compromised skin applications, such as applying a whipped sunscreen product or a whipped after sun product.

The disclosed whipped product form is designed to dispense, for example and without limitation, lotion/cream/ointment/oral dosage form/whipped cream in a controlled manner by delivering a pressurized, foaming formulation via a dispensing orifice at the touch of a button. The product is dispensed via an actuator that depresses a valve stem into a female aerosol valve. Upon activation, the gas-saturated formulation experiences a drop in pressure as it moves from a pressurized containment system to ambient conditions. This change in pressure allows the saturated gas to rapidly expand, creating bubbles within the formulation, leading to a formulation of reduced density. Formulation customizations allow these bubbles to remain stable for 10 seconds or longer, permitting the user to spread the resulting product onto a surface with enhanced coverage benefits.

Although specific suppliers of commercially avail-able ingredients may be listed herein, it is understood that these products may be available from additional suppliers and that the instant invention is not limited to only that ingredient from the specifically cited supplier. Rather the supplier is being provided as an example of what is commercially available.

Description of Certain Embodiments of the Whipped Product

Luxurious whipped product, whipped, spongy, soft, pillowy.
No shake whipping.
Not runny; stays where you put it
Easy to apply and handle, faster, easier application.
More controllable, no drip allows precise placement, convenience of C-Spray but no wet-look. Applying easily to back, not chasing a liquid product, no smear mess but pull product to control application. Can apply multiple dollops to body at one time. Thus can put package down and not have to touch again while rubbing in multiple dollops
Quick rub-out time
Different sensory (drag of product), smoothness
Connect emotionally with application experience
Perception-whipped dries more quickly.
After feel-no wetness/drag/tackiness
Coping mechanism: previous product dispenser has loud sound and needs shake before coming out, whipped made convenient/quiet/easy dispose
Characterization of the product-brightness, density, bubble size, bubble distribution, surface tension, pH, stability, sheer, dose, sound, drag (skin feel)-low drag, sheen, full bodied, insulation, contact temperature, wetness, slip, sound cue
Change in physical properties only, maintains formulation properties with enhanced application benefits, "transforms application but not properties"
May have 5×-10× expansion in density and/or volume
Micro-voids, micro-bubbles, infused, air emulsion, trap gas in structure
Consistent whipped product over life of product-beginning to end.
Reduce in dead inventory.
Stable, supersaturated nitrous oxide loading, helps to create microbubbles and thus unique structure
Can create variable drag experience based on processing reduced drag application, increased/better/easier application
low sheer application for sensitive/damaged skin
Create and maintain higher solubility product through containment under elevated pressure (allows constant pressure overtime).
Size of nozzle (sheer rate impact)→sound profile Sensory Impact The disclosed whipped formulation product represents the careful culmination of advancements in formulation, processing, and packaging to deliver a rich, creamy, spreadable, lightweight whipped product for consumer application. The disclosed formulation also delivers desired sensory impact to a user.

Sensory impact (such as appearance of the whipped product, sound upon dispensing the product from the can, and impact on the skin of the whipped formulation, etc.) to the user may be evaluated by, for example, trained personnel to determine how product variants are perceived differently by the user, with statistical confidence. Those formulations determined to have desired sensory impact are thus selected. In certain embodiments, the user's senses are highly satisfied by the disclosed formulation after its application on the user.

Two intertwined process variables may contribute to controlling the consumer experience associated with a base formula; gas loading (e.g., nitrous oxide) into the formulation with the active ingredient, which impacts density, spreadability, sound, and physical appearance of product; and pre-gas can pressure, which influences stability of gas emulsion, sound, speed of dispense, sputtering, and "quality" characteristics. Multiple product variants, combining these two process variables, are run and are being physically evaluated. Physical measurements may be made, including CT scans to yield "in can" product profile characterization details; dispensing observations (such as appearance of the whipped product, sound upon dispensing the product from the can, and impact on the skin of the whipped formulation, etc.), and high temperature foam stability; and post-dispensing physical measurements including density, bubble size, and bubble size distribution. Sensory impact (such as appearance, sound, and skin impact) to the user of these multiple product variants may be evaluated by, for example, trained personnel to determine how product variants are perceived differently by the user, with statistical confidence. Some of these tested whipped formulations would have desired sensory impact to the user. For any given product, the following parameters, as well as any other parameters that impact a user's sense(s), may be evaluated.

Appearance: visual compactness, integrity of shape, gloss, hue, intensity, brightness, opacity, whitening, etc.

Sound impact upon dispensing from the can: volume, tone, crackling/popping, sputtering, etc.

Skin Feel: firmness, stickiness, cohesiveness, peaking, wetness, spreadability, coolness, thickness, slipperiness, oiliness, waxiness, greasiness, rubs to absorbency, tautness, roughness, thickness of residue, grittiness, graininess, chalkiness, peeling/flaking, pilling, powdery-ness, plastic/coated, etc.

In certain embodiments, the whipped formulations have desired sensory impact to a user, who may be a human user. In certain embodiments, the formulations have high sensory impact to the user; in certain embodiments, the high sensory impact is characterized by one or more of the following: positive appearance, low sound impact, high integrity of shape, visual compactness, high spreadability, positive skin feel, afterfeel (immediately after application or after a few minutes after application, such as about 10 minutes after) as well as other sensory input perceivable by a user.

The disclosed method allows for tweaking the consumer experience attributes of a whipped formulation in multiple directions, allowing is to deliver "soft and gentle" or "aggressive and greasy," etc., depending on consumer preference. Some of the attributes are: appearance, sound impact, integrity of shape, spreadability, and skin feel. All these, as well as other parameters, may be chosen such that the whipped formulation has the desired attributes.

For appearance, in certain embodiments, the appearance is a well-formed dollop; in other embodiments, such as for Kid's Messy-Loud sunscreen, the product upon dispensing sputters.

For sound impact, in certain embodiments, such as Kid's Messy-Loud sunscreen, the sound impact upon dispensing is obnoxiously loud and disruptive; in other embodiments, the sound impact is as low as possible.

For skin feel, in certain embodiments, such as Baby and Clearly Sheer, the skin feel provided by the formulation is a soft, none greasy-feel experience; in other embodiments, such as sunscreen for sport users who want to feel their sunscreen is working hard and staying with them as they move, the skin feel provided is one or more of greasiness, heaviness, and glossy.

In certain embodiments, the disclosed whipped product dispenses in a light whipped form, infused with tiny bubbles that make the texture of the formulation lighter, smoother and easier to spread across the skin. This texture also makes the formulation feel less greasy and more aesthetically pleasing on hands and skin, leaving a 'sumptuous' feel with a sunscreen during application. This formulation spreads quickly and disappears rapidly as the user rubs the formulation into the skin. Such a formulation may even prevent excess application of the agent and may offer ecological advantages.

In another embodiment, the disclosed whipped product offers an easier, faster, smoother, and less greasy skincare formulation than a traditional formulation.

In certain embodiments, the physical stability of the whipped products obtained may also be characterized by means of these tests: determination of the organoleptic characteristics (e.g., aspect, color, odor), characterization of the texture (e.g., thick, fluid, greasy, non-greasy), and characterization of the spreadability.

In certain embodiments, the disclosed formulation has one or more of the following physical characteristics: a majority of bubbles being of a bubble size of less than 20 μm, high number of bubbles, high bubble density, and high foam stability. In certain embodiments, the disclosed formulations have high foam stability at high temperatures, such as at 25° C. to 37° C., or 37° C. to 50° C.

In certain embodiments, the color of the whipped formulation post-dispensing is white. The whiteness of the whipped lotion may be used as a visual queue for application on skin.

In certain embodiments, the formulation has at least about 60% of the gas bubbles at ≤100 μm, after the formulation is expelled from the package. In certain embodiments, the formulation has at least about 40% of the gas bubbles at ≤60 μm, after the formulation is expelled from the package.

In certain embodiments, the whipped formulation product is characterized by microdispersion. In certain embodiments, the whipped formulation product is characterized by substantially consistent microvoid.

In certain embodiments, the whipped formulation product is highly emollient. In certain embodiments, the whipped formulation product has about 60% or more of the gas bubbles at ≤100 μm. In certain other embodiments, the whipped formulation product has about 40% or more of the gas bubbles at ≤60 μm. The gas bubbles are formed from the gas propellant co-mingled with the formulation prior to filling the formulation into the package.

In certain embodiments, the formulation has one or more of characteristics such as little or no wetness after application, having a collapse time of at least 60 seconds, or structurally stable for at least 30 minutes.

EXAMPLES

For this invention to be better understood, the following examples are set forth. These examples are for purposes of illustration only and are not be construed as limiting the scope of the invention in any manner.

Example 1. Laboratory Manufacturing Process for Whipped Sunscreen Lotion SPF 50

TABLE 1

Concentrate (Base Formulation): Whipped Sunscreen Lotion Concentrate, Batch Size: 1000 g.

| | Concentration (% w/w) | Manufacturing Directions |
|---|---|---|
| Part A Ingredients | | |
| Purified water, USP | 43.77 | Step 1: In a container large enough to hold the entire batch, add the Water of Part A, with rapid mixing, add the Avicel RC-591 of Part A and mix until free from lumps. |
| Avicel RC-591 | 2.00 | |

TABLE 1-continued

Concentrate (Base Formulation): Whipped Sunscreen Lotion Concentrate, Batch Size: 1000 g.

| | Concentration (% w/w) | Manufacturing Directions |
|---|---|---|
| Part B Ingredients | | |
| Disodium EDTA | 0.10 | Step 2: Add the ingredients of Part B to |
| Ganex P-904 LC | 0.80 | the batch of Step 1 and mix until |
| Glycerin, USP | 2.50 | dispersed. Begin heating the aqueous |
| Sunspheres PGL | 8.00 | phase to 158-167° F. (70-75° C.) with mixing. |
| Part C Ingredients | | |
| Octocrylene, USP | 8.00 | Step 3: In a separate container, add the |
| Octisalate, USP | 4.50 | ingredients of Part C and heat to 158- |
| Homosalate, USP | 10.00 | 167° F. (70-75° C.) with mixing until |
| Dicaprylyl Ether | 2.00 | dissolved. |
| Vitamine E, USP | 0.25 | |
| Avobenzone, USP | 3.00 | Step 4: Add the oil phase of Step 3 to the |
| Oxybenzone, USP | 6.00 | batch of Step 2 and mix until homogenous. |
| Prolipid 141 | 4.50 | Turn off heat and cool to at least 113° F. |
| Lanette 22 (CM) | 2.00 | (45° C.). |
| Cetyl Alcohol, NF | 1.00 | |
| Chlorphenesin | 0.27 | |
| Part D Ingredients | | |
| Sodium Ascorbyl Phosphate | 0.01 | Step 5: Add Part D ingredients to the batch then slowly added the Dry-Flo to the |
| Benzyl Alcohol, NF | 0.90 | batch and mix well. |
| Fragrance | 0.40 | |
| Dry-Flo Pure | 4.00 | |
| Part E Ingredients | | |
| Purified water, USP | Q.S. | Step 6: Q.S. the batch with water of Part E and mix well. Package accordingly. |

TABLE 2

Finished Product (Concentrate + Gas): Whipped Sunscreen Lotion SPF 50 (BOV) (Z16-014), Batch Size: 5 oz. Bag on Valve (BOV) Can

| Ingredients | Concentration (% w/w) |
|---|---|
| Whipped Sunscreen Lotion Concentrate | 98.10 |
| Nitrous Oxide (1st Gas) | 1.90 |

The following three major steps are involved in manufacturing a whipped product (Finished Product).
1) Pre-mixing step: Co-process of a base formulation (Concentrate) and a 1st Gas.
2) Pre-pressurizing step: Pressurizing of a 2nd gas between a bag and the inside wall of the product package.
3) Packaging step: Packaging the pre-mixed formulation (concentrate+the 1st gas) into the pre-pressurized Bag on Valve (BOV) package.

In other embodiments, the following steps are involved in manufacturing a whipped product.
1. Concentrate Production Step: The base sunscreen emulsion was processed in accordance with the manufacturing process according to Table 1, and held for the Gas Co-Processing step.
2. Gas Co-Processing Step: The base sunscreen formulation was added to the mixing chamber and a 1st Gas was vigorously co-mingled or dispersed with a high pressure mixing head into the base formulation at 150 psig, and held at pressure until Packaging Step.
3. Pre-pressurizing step: Pressurizing of a 2nd gas between a bag and the inside wall of the Bag on Valve product package to no less than 40 psig.
4. Packaging step: Packaging the pre-mixed formulation (concentrate+the 1st gas) into the pre-pressurized Bag on Valve (BOV) package by injection into the two way valve opening at a pressure of at least 400 psig.

Generally, a blended base formulation (e.g., Y71-159) is transferred into a hopper, pressurized and under a controlled temperature, rate of flow and pressure is transferred into a high shear, continuous-flow, high-pressure "whipping" head, which rapidly mixes the base formulation with a series of infusion gas injector ports which controls the gas pressure and rates of flow with a selection of gases (or gas) to rapidly co-mingle the gas (1st gas) and the base formulation, effectively "dispersing" the gas into the formulation prior to injection into the pre-pressurized Bag on Valve (BOV) package. In addition, the gas-infused formulation is tested for density inline and controlled under pressure and finally injected under pressure into the desired package.

TABLE 3

| Ingredient | Concentration (% w/w) | | | |
|---|---|---|---|---|
| | Whipped Sunscreen Lotion Concentrates Y71-128 (SPF 30) | Whipped Sunscreen Lotion Concentrates Y71-189 (SPF 30) | Whipped Sunscreen Lotion Concentrates Y71-122 (SPF 50) | Whipped Sunscreen Lotion Concentrates Y71-159 (SPF 50) |
| Avicel RC-591 | 2.00 | 2.00 | 2.00 | 2.00 |
| Disodium EDTA | 0.10 | 0.10 | 0.10 | 0.10 |
| Ganex P-904 LC | 0.80 | 0.80 | 0.80 | 0.80 |
| Glycerin | 2.50 | 2.50 | 2.50 | 2.50 |
| Sunspheres PGL | 8.00 | 8.00 | 8.00 | 8.00 |
| Octocrylene | 8.00 | 8.00 | 4.00 | 8.00 |
| Octisalate, USP | 4.50 | 4.50 | 4.50 | 4.50 |
| Homosalate | 10.00 | 10.00 | 10.00 | 10.00 |
| Dicaprylyl Ether | 2.00 | 2.00 | 2.00 | 2.00 |
| Tocopherol | 0.25 | 0.25 | 0.25 | 0.25 |
| Avobenzone | 3.00 | 3.00 | 3.00 | 3.00 |
| Oxybenzone | — | — | 6.00 | 6.00 |
| Prolipid 141 | 4.50 | 4.50 | 4.50 | 4.50 |
| Lanette 22 (CM) | 2.00 | 2.00 | 2.00 | 2.00 |
| Cetyl Alcohol | 1.00 | 1.00 | 1.00 | 1.00 |
| Chlorphenesin | 0.27 | 0.27 | 0.27 | 0.27 |
| Sodium Ascorbyl Phosphate | 0.01 | 0.01 | 0.01 | 0.01 |
| Benzyl Alcohol | 0.90 | 0.90 | 0.90 | 0.90 |
| Fragrance SZ-1405 MOD 2010 | — | 0.40 | — | 0.40 |
| Citrus Waters SZ28506 | 0.15 | — | 0.15 | — |
| Dry-Flo Pure | 4.00 | 4.00 | 4.00 | 4.00 |
| Water | Q.S. | Q.S. | Q.S. | Q.S. |

Example 3. Characteristics of Whipped Sunscreen Products

1. BACKGROUND

Whipped sunscreen products have been developed. The whipped sunscreen product (Finished Product) consists of a base emulsion formulation (Concentrate) and a propellant (Gas), which is then packaged into a pre-pressurized Bag on Valve (BOV) package. Exemplary manufacturing process steps for whipped sunscreen products at pilot scale are provided in Examples 1 and 2.

2. OBJECTIVES

The objective of this study is to evaluate the characteristics of these whipped sunscreen products stored at various storage conditions.

3. EVALUATION STUDIES

Formulation details for whipped sunscreen products used in the following evaluation studies are summarized in Table 3. All whipped sunscreen products (SPFs 30 and 50) that are tested in the evaluation studies are manufactured and packaged at the intended manufacturing site 3.1. Evaluation Study I: Features of "Whipped-Foam" Delivered from Whipped Sunscreen Products The following features are assessed for whipped sunscreen products:

Appearance and Stay-put-ness;
Spreadability and Texture; and
Extent of product transfer after application.

One drawback of standard lotion products is their tendency to become runny or drippy after application. As shown in FIG. 1A-FIG. 1D, Kiehl's sunscreen lotion, a typical sunscreen lotion product, become runny right after application. On the contrary, a whipped sunscreen lotion delivers a voluminous and creamy "whipped-foam" that does not deflate soon after dispensing, and stays firmly on the application site and then resists to run. This stay-put-ness attribute of whipped sunscreen products is advantageous as they do not need to be spread immediately after application.

FIG. 2A-FIG. 2F compare the spreaderability and texture attributes of a whipped sunscreen lotion to those of two foaming products, the currently marketed Waterbabies foaming sunscreen lotion and a mousse-type lotion. Even though the dispensed "whipped-foam" displays substantial firmness and body, it breaks down easily and spread evenly on skin as compared to the foams that are delivered from the two other foaming products. The texture of the "whipped-foam" is soft, silky smooth and luxurious creamy feel, and no crumbliness is observed during physical maneuvering. On the other hand, the textures of Waterbabies foaming lotion and mousse-type lotion are "over-aerated, thin and crumbly" and "over-aerated, sticky, with torn edges upon physical manipulation," respectively.

Whipped sunscreen products have been described as "huggable" as users feel there is very little oiliness/tack after application. A preliminary "product transfer" study is conducted using a whipped sunscreen lotion and Waterbabies foaming lotion. In this study, the sunscreen application thickness is 2.5 mg/cm$^2$, which is greater than the recommended thickness, 2 mg/cm$^2$. Briefly, about 0.5 g of each sunscreen product is applied on each arm (application area: 200 cm$^2$) and rubbed by hand. After 1 minute drying time, a piece of cotton is placed on each arm and pressed by 1 Kg Calibration Weight for 30 seconds. The transferred sunscreen on each cotton piece is then exposed to UV light to show the difference in transferred sunscreen amount between the whipped and the foaming sunscreen lotion products. As presented in FIG. 3, the whipped lotion shows significantly lower level of product transfer relative to the foaming lotion, supporting the aforementioned users' satisfying experience with whipped sunscreen products.

Figure 4:
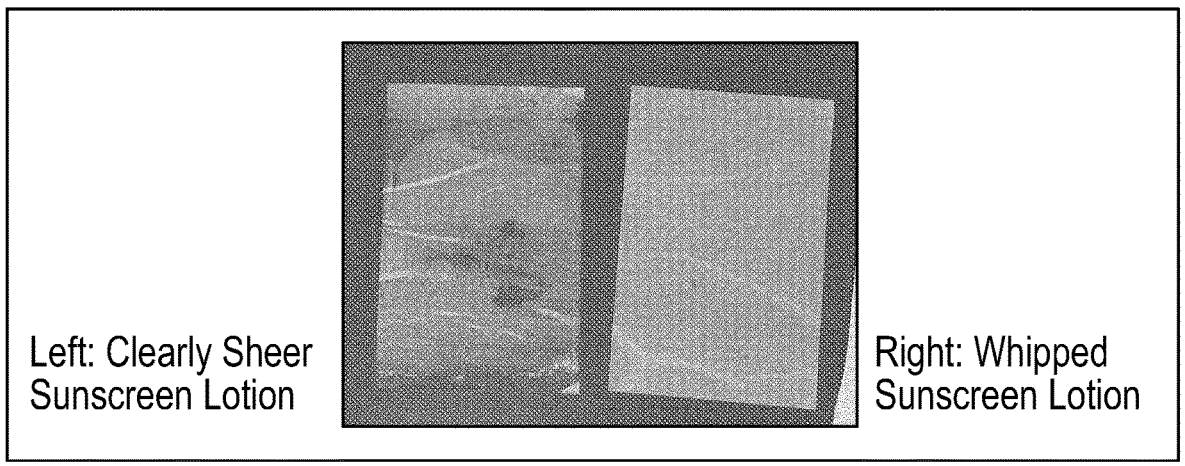
FIG. 4 shows results for the extent of product transfer after application: whipped sunscreen lotion (Finished Product: Z16-014, Concentrate: Y71-159) versus clearly sheer sunscreen lotion.

Subsequently, an in-use "product transfer" study is performed to further mimic consumer behavior. For this study, approximately the same amount of each sunscreen product is applied on each arm and then a piece of blotting paper is placed on each arm right after rub out. The blotting papers are pressed firmly by hands with appropriate pressure for 10 seconds. The transparency on the papers indicates the transfer of sunscreen products. The results (FIG. 4) show that the level of product transfer from the currently marketed Clearly Sheer sunscreen lotion SPF 50 is substantially higher than that from a whipped sunscreen lotion SPF 50. In fact, there is very little to no product transfer present in the paper for the whipped sunscreen lotion SPF 50. This study results also confirm the previous preliminary study results and suggest that consumers would feel comfortable wearing clothes over the whipped sunscreen products.

Figure 5:
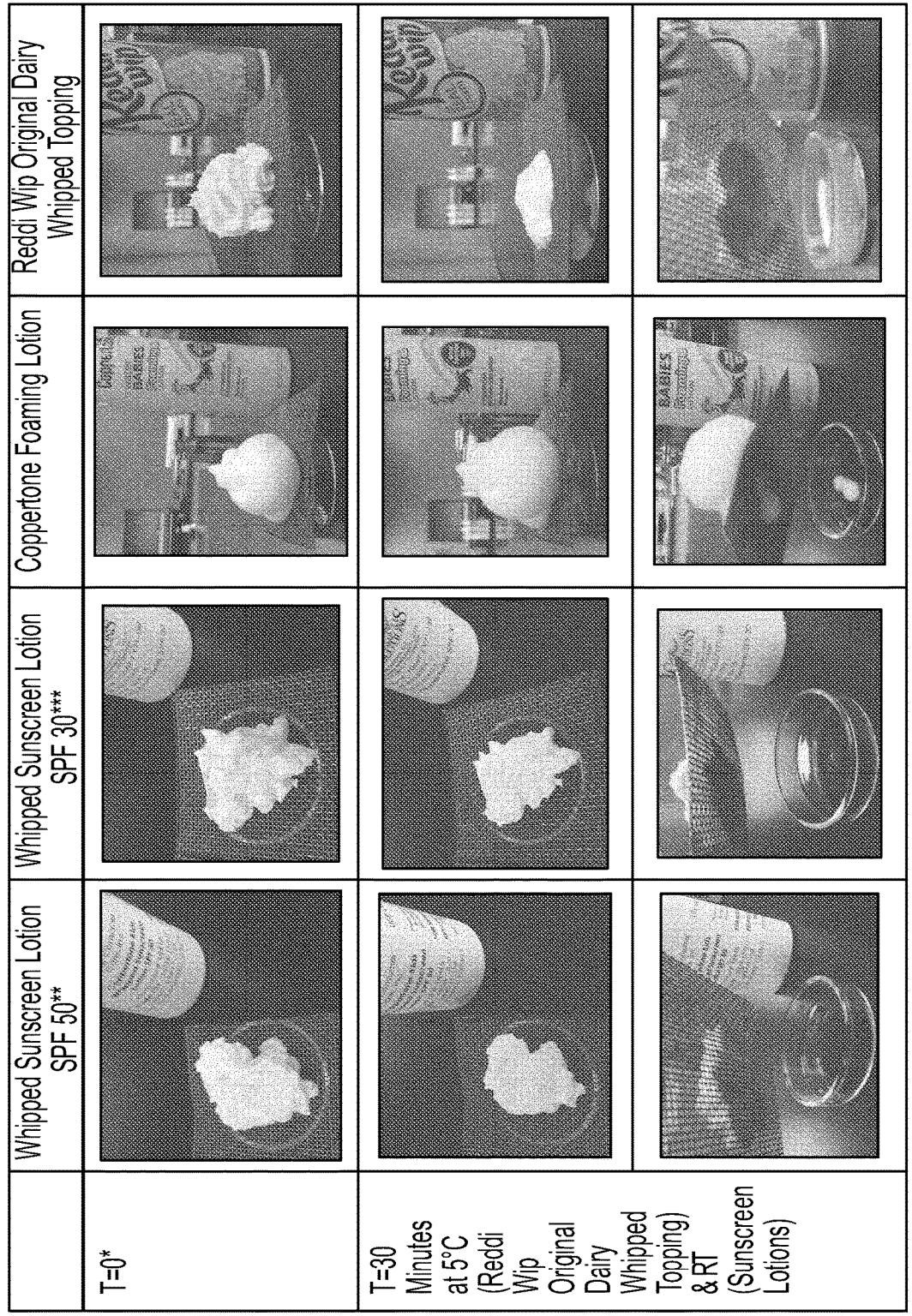
FIG. 5 shows results of appearance and drain/Collapsing times of "whipped-foam" delivered from whipped sunscreen lotions versus other foaming products.

3.2. Evaluation Study II: The Drain and/or Collapsing Times of "Whipped-Foam" Delivered from Whipped Sunscreen Lotion Products One important quality of the whipped formulations is their ability to resist collapsing that would cause liquid drainage from the foam. By monitoring the drain or collapsing times of foams, the relative stability of various foams can be compared. FIG. 5 shows the drain or collapsing time results of four foams that are delivered from four different products, two whipped sunscreen lotion products (SPFs 30 and 50), Coppertone Waterbabies foaming lotion, and Reddi Wip Original Dairy Whipped Topping. Initially, the dispensed "whipped-foams" from two whipped lotions products have similar appearance compared to those from the Waterbabies foaming lotion and Reddi Wip Whipped Topping (has been stored at 5° C.). However, after 30 minutes, the "whipped-foams" still largely maintain their foam structure, while the Waterbabies foaming lotion and Reddi Wip Whipped Topping have partially liquidized and lost some of their foam structures. The two whipped sunscreen products are more stable: they provide the longest drain or collapsing time. This longer drain or collapsing time can be beneficial as customers can control the speed of distributing the whipped lotion products to themselves and others (particularly kids).

3.3. Evaluation Study III: Physical Stability of "Whipped-Foam" Delivered from Whipped Sunscreen Products Developmental stability studies are conducted on two whipped sunscreen lotion products (SPFs 30 and 50). For these studies, packaged samples are placed on developmental stability at three different storage conditions (room temperature, 1 day at 40° C./20% RH, and 1 month at 50° C.). The stability results presented in FIG. 6 demonstrate that both whipped lotion products are able to produce "whipped-foam" with acceptable structure even right after storage at 50° C./75% RH (relative humidity) for 1 month (note that the temperature of the each sample is close to 50° C. when the 'whipped-foam" was dispensed). There is no significant change in appearance of "whipped-foam" for the samples stored at 40° C./20% RH for 1 day and the samples stored for 1 month at 50° C. and then allowed to cool to RT. It appears that thermal stress does not have a significant impact on the performance of whipped sunscreen products. This characteristic can be particularly useful for sunscreen products, which are intended for use in elevated temperature environments.

3.4. Evaluation Study IV: The Size and Distribution of Gas Bubbles in "Whipped-Foam" Delivered from Whipped Sunscreen Products To gain better assessment of thermal stress and temperature cycling effects on whipped sunscreen lotion products, microscopic observation is performed on the samples stored for 1 or 3 months at four different storage conditions (RT, Freeze (−10° C.)/Thaw (RT) Cycles (4 cycles), 40° C./20% RH, and 50° C.). Photomicrographs were taken utilizing KEYENCE digital microscope VHX-600.

Figure 11:
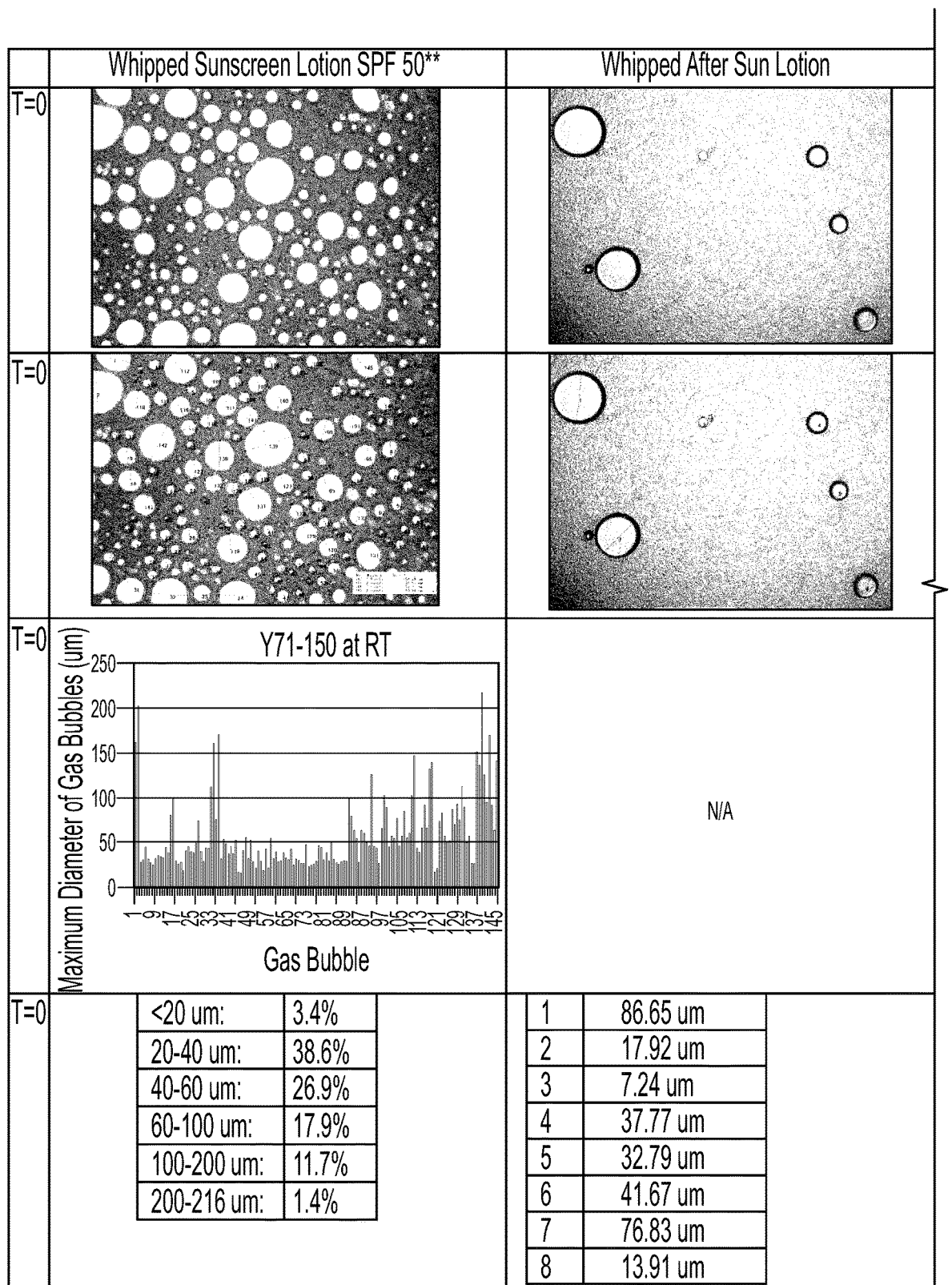
FIG. 11 is a photomicrograph (at 500× magnification): gas bubble ($N_2O$) distribution in "whipped-foam" delivered from whipped sunscreen lotions vs other foaming products.

The photomicrographic method of measuring gas bubble size is selected since the drainage rate of "whipped-foam" was very low as demonstrated in Evaluation study II (FIG. 5). This method is not applicable to conventional foam that drains faster, because the sample would drain appreciably during the time of the experiment (e.g., photomicrograph of Reddi Wip Original Dairy Whipped Topping shown in FIG. 11).

Photomicrographs in FIG. 7A-FIG. 7C, FIG. 8A-FIG. 8D, FIG. 9A-FIG. 9D and FIG. 10A-FIG. 10D show characteristic microscopic images of "whipped-foam" taken at two different times (T-initial and T=20 minutes (the resultant "whipped-foam" had been kept at room temperature (RT) for 20 minutes after dispensing)). Initially, the gas bubbles are spherical, separated by liquid films. Subsequent shots (T=20 minutes) show that shapes of some bubbles are more like polyhedral rather than spheres. In addition, the number of the bubbles observed is decreased slightly as compared to the initial level.

As presented in FIG. 7A-FIG. 7C, FIG. 8A-FIG. 8D, FIG. 9A-FIG. 9D and FIG. 10A-FIG. 10D, no significant change in distribution of gas bubble sizes in the resultant "whipped-foam" is observed for all of the samples. The measured diameters for at least about 60% of gas bubbles are ≤100 μm (the diameters for at least about 40% of gas bubbles are ≤60 μm). Subsequent measurement (T=20 minutes) of gas bubbles show that the diameters for at least about 40% of gas bubbles are ≤100 μm.

Figure 6:
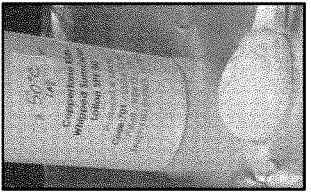
FIG. 6 shows appearance and stability of "whipped-foam" delivered from whipped sunscreen lotions, which had been stored at various storage conditions.
Figure 7A:
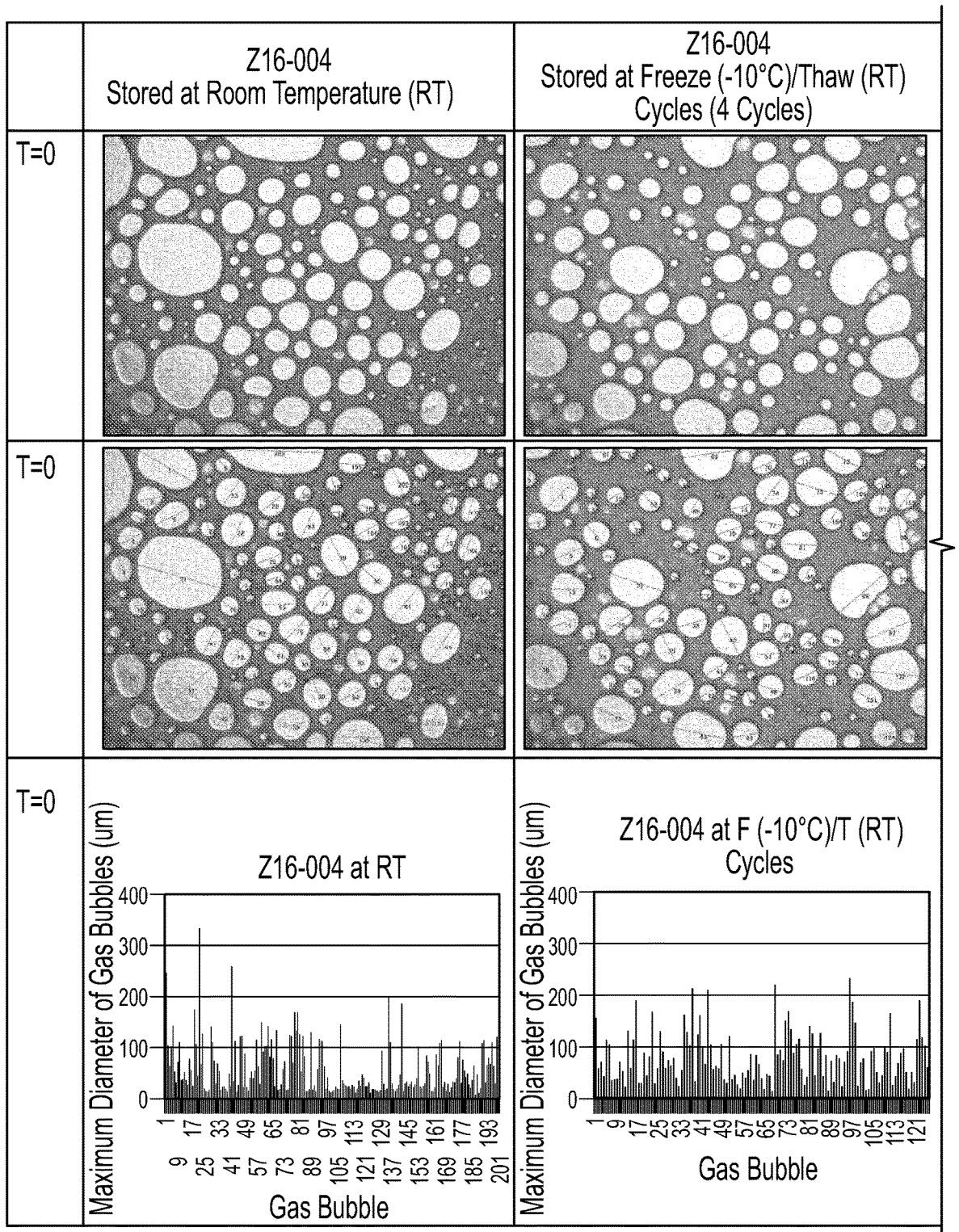
FIG. 7A: Z16-004 stored at room temperature (RT) and stored at Freeze (−10° C.)/Thaw (RT) Cycles (4 cycles); and 7B-7D: Z16-004 stored at 40° C./20% RH for 3 Months and stored at 50° C./75% RH for 1 month.
Figure 7C:
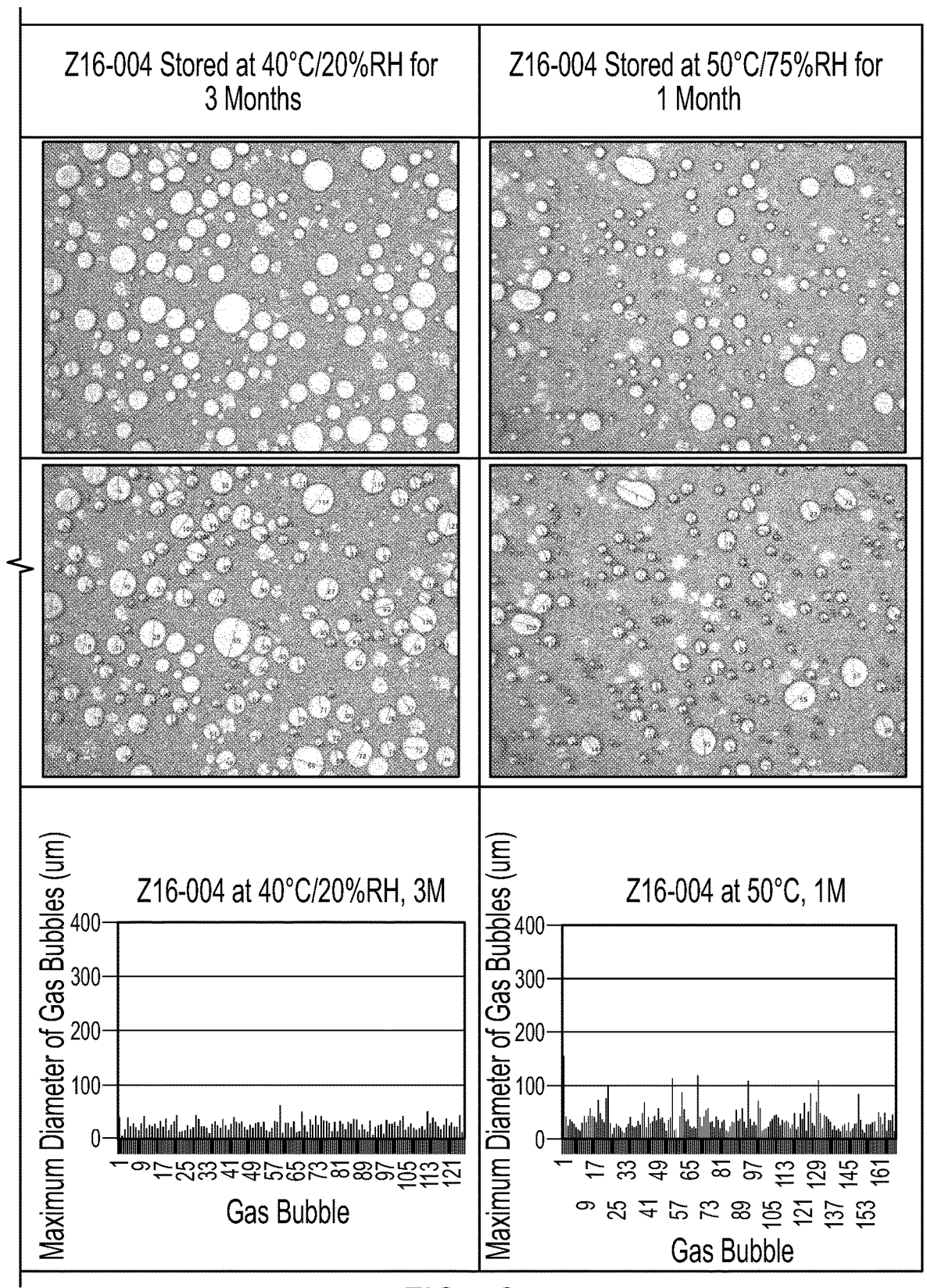
FIG. 7 is a photomicrograph (at 500× magnification): gas Bubble ($N_2O$) distribution in "whipped-foam" delivered from whipped sunscreen lotion SPF 30 (Finished Product: 216-004, Concentrate: Y71-128), which had been stored at various storage Conditions.
Figure 7D:
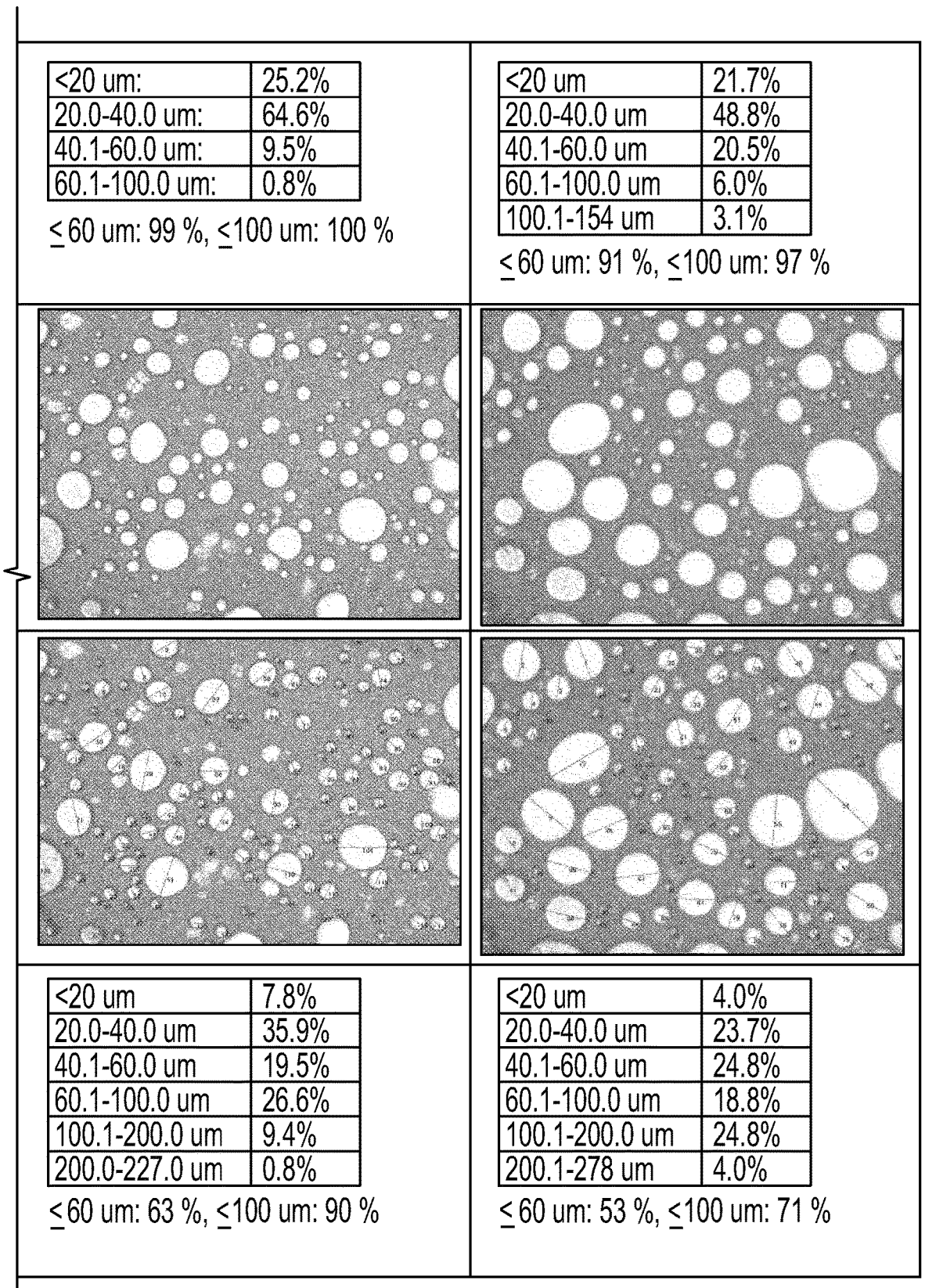
Figure 8A:
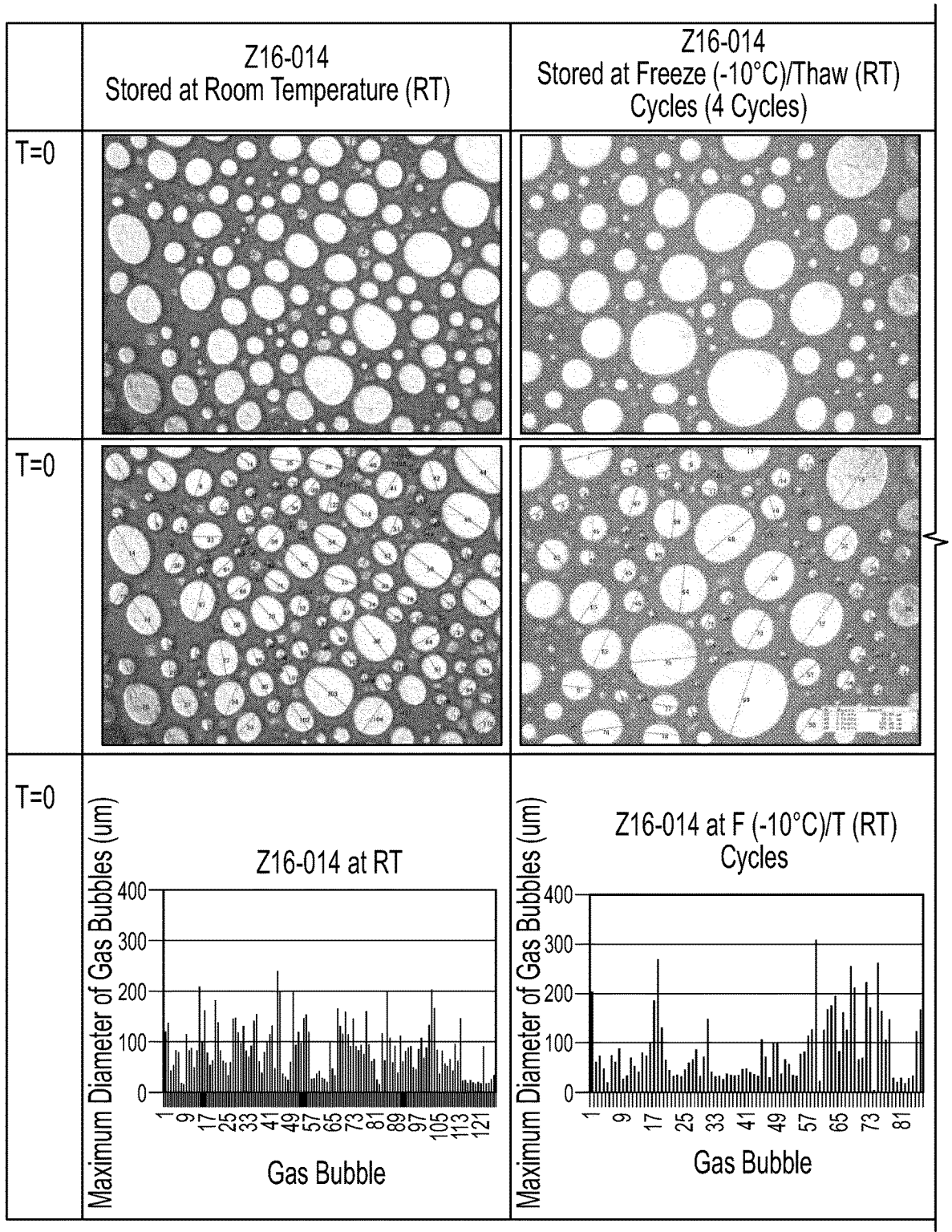
FIG. 8A: Z16-014 stored at room temperature (RT) and stored at freeze (−10° C.)/thaw (RT) cycles (4 cycles); and 8B-8D: Z16-014 stored at 40° C./20% RH for 3 months and stored at 50° C./75% RH for 1 month.
Figure 8C:
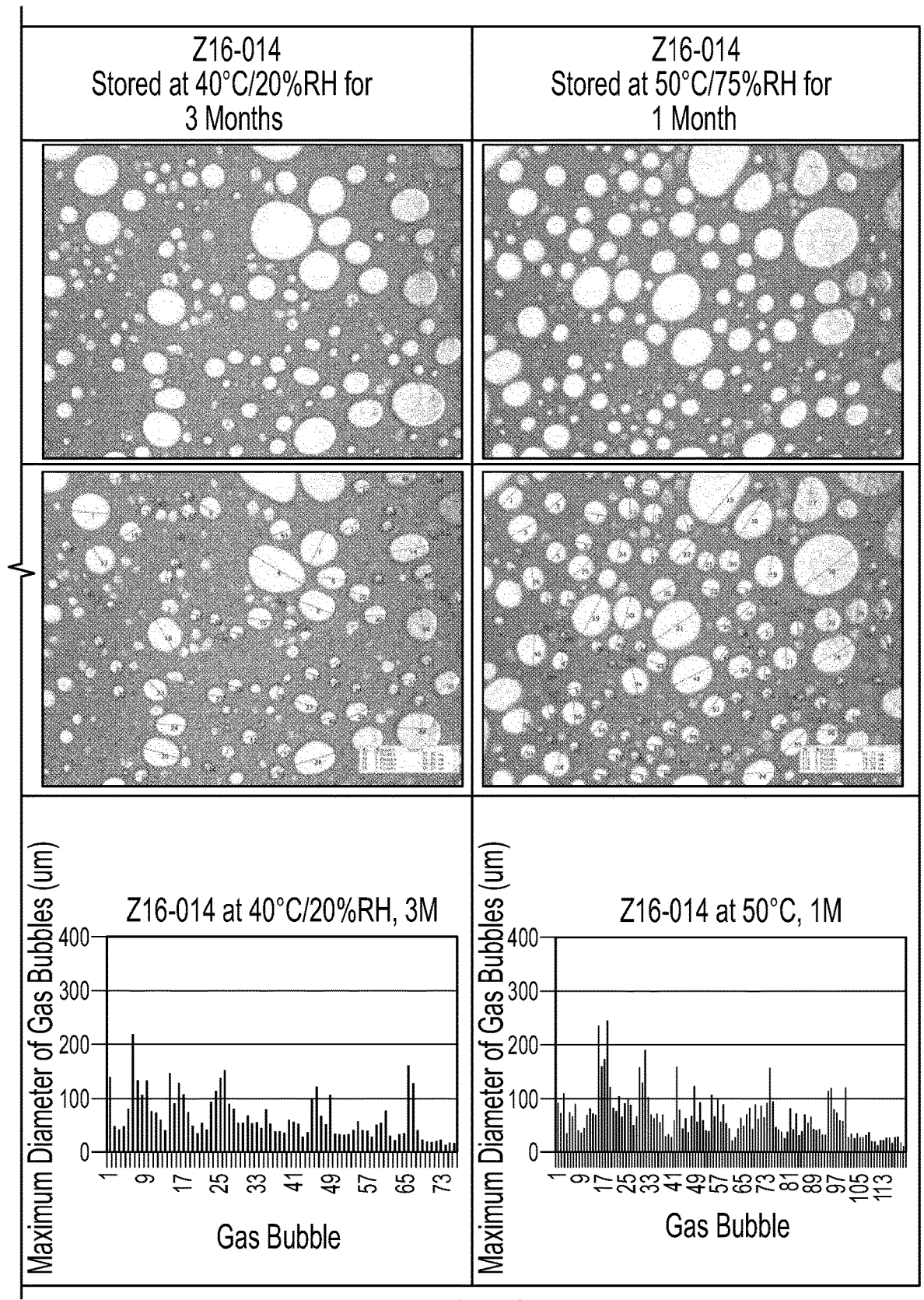
FIG. 8 is a photomicrograph (at 500× magnification): Gas Bubble ($N_2O$) Distribution in "whipped-foam" delivered from whipped sunscreen lotion SPF 50 (Finished Product: Z16-014, Concentrate: Y71-159), which had been stored at various storage Conditions.
Figure 8D:
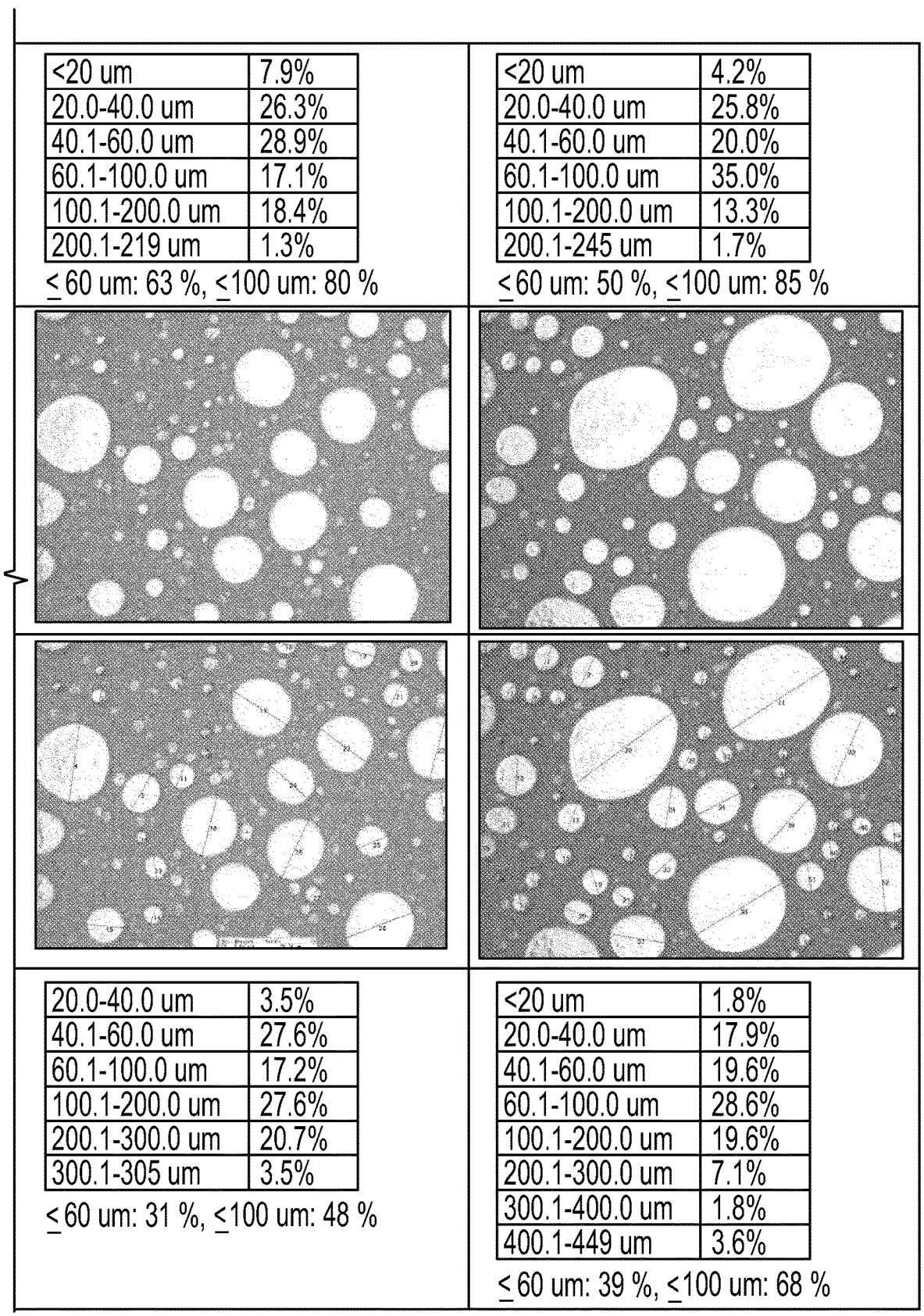
Figure 9A:
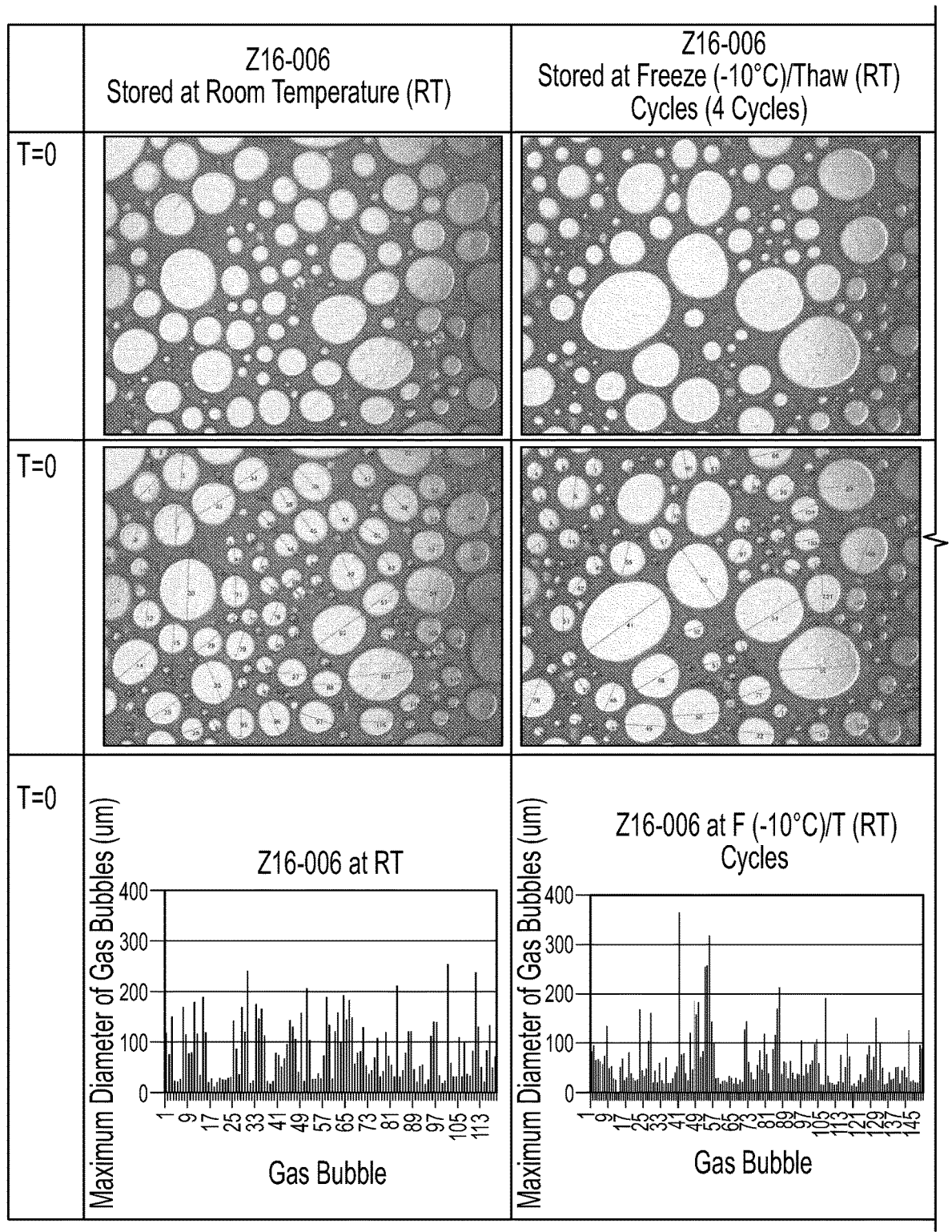
FIG. 9A: Z16-006 stored at room temperature (RT) and stored at Freeze (−10° C.)/Thaw (RT) cycles (4 cycles); and 9B-9D: Z16-006 stored at 40° C./20% RH for 3 months and stored at 50° C./75% RH for 1 month.
Figure 9C:
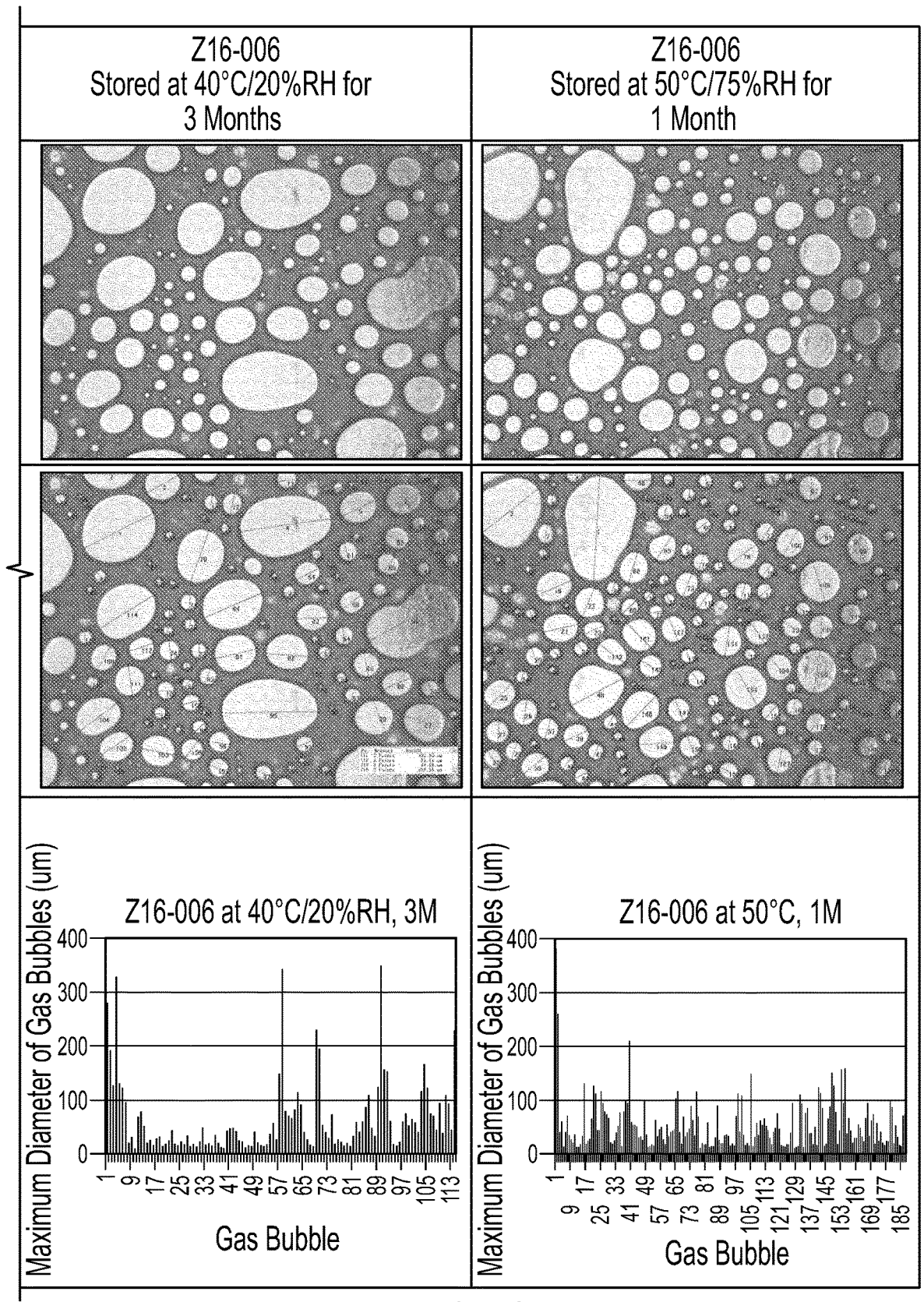
FIG. 9 is a photomicrograph (at 500× magnification): Gas Bubble ($N_2O$) distribution in "whipped-foam" delivered from whipped sunscreen lotion SPF 30 (Finished Product: Z16-006, Concentrate: Y71-189), which had been stored at various storage Conditions.
Figure 9D:
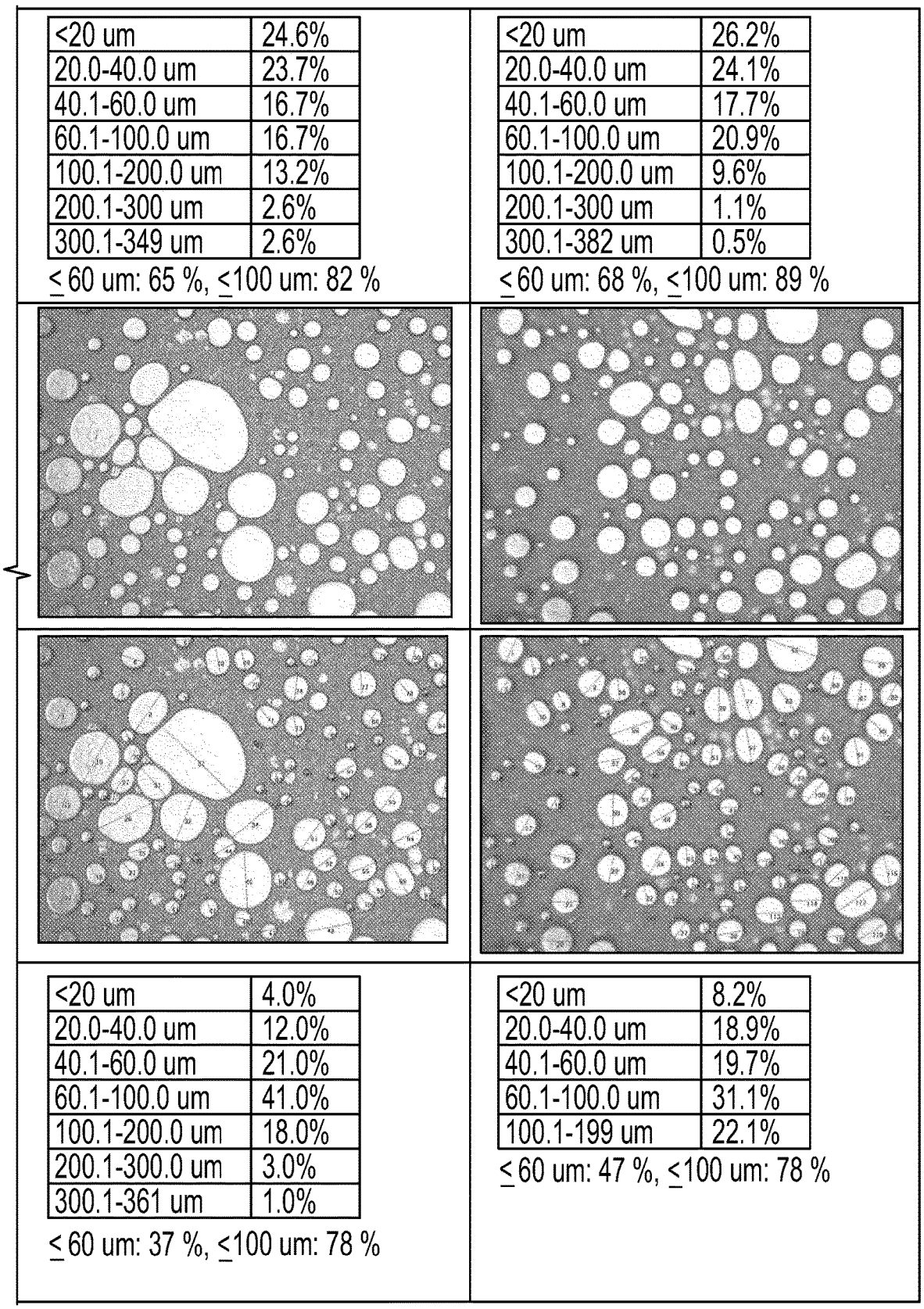
Figure 10A:
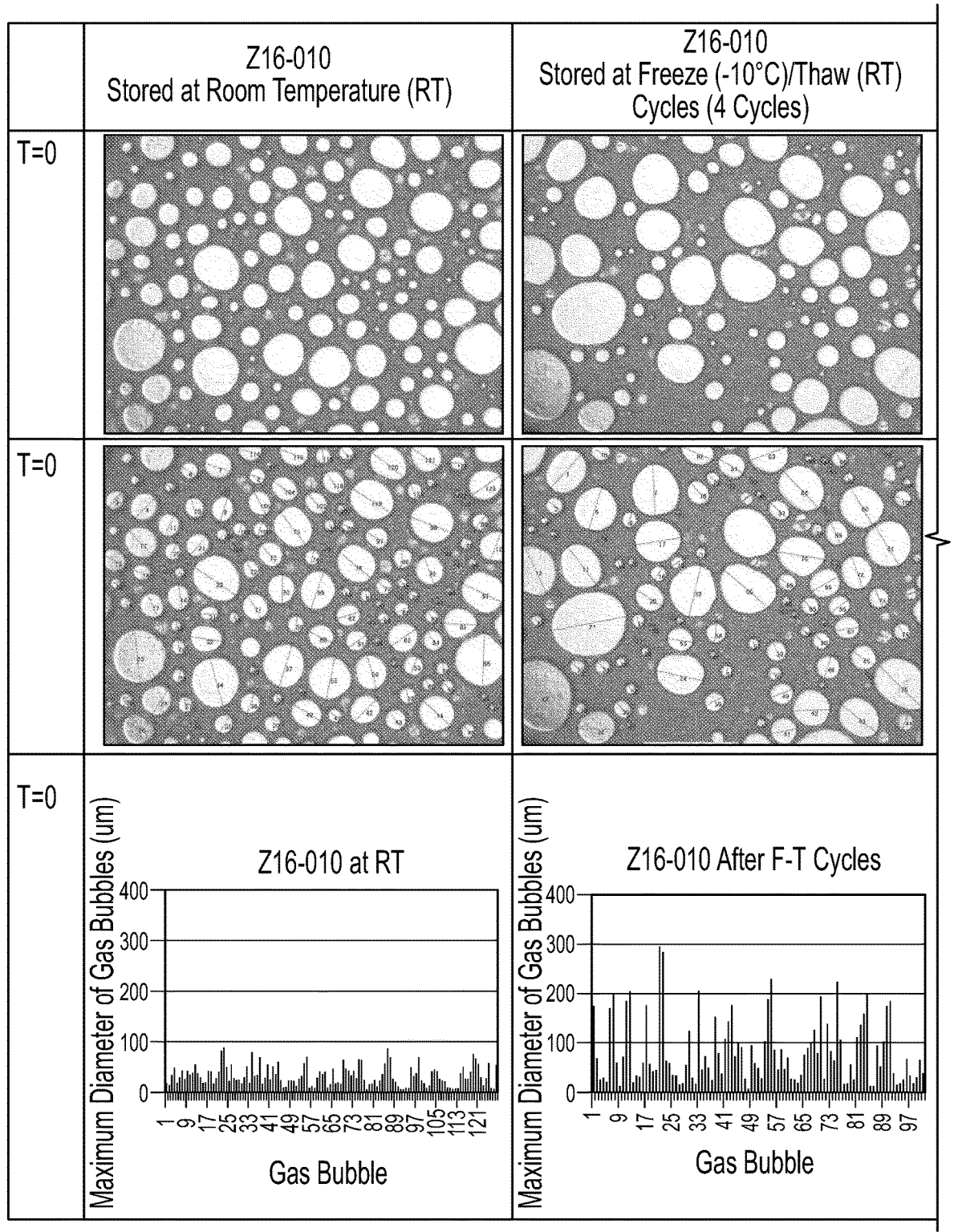
Figure 10C:
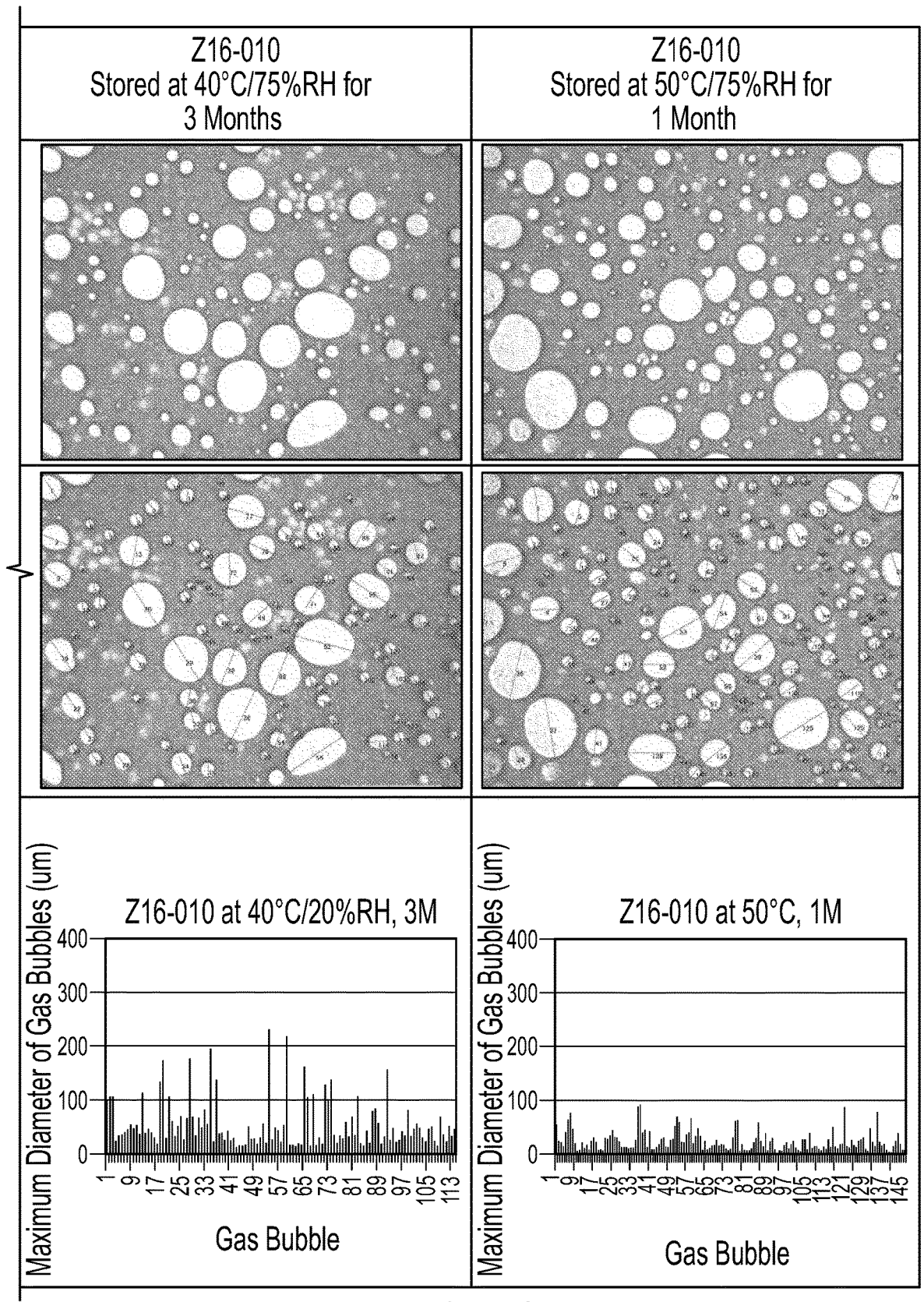
Figure 10D:
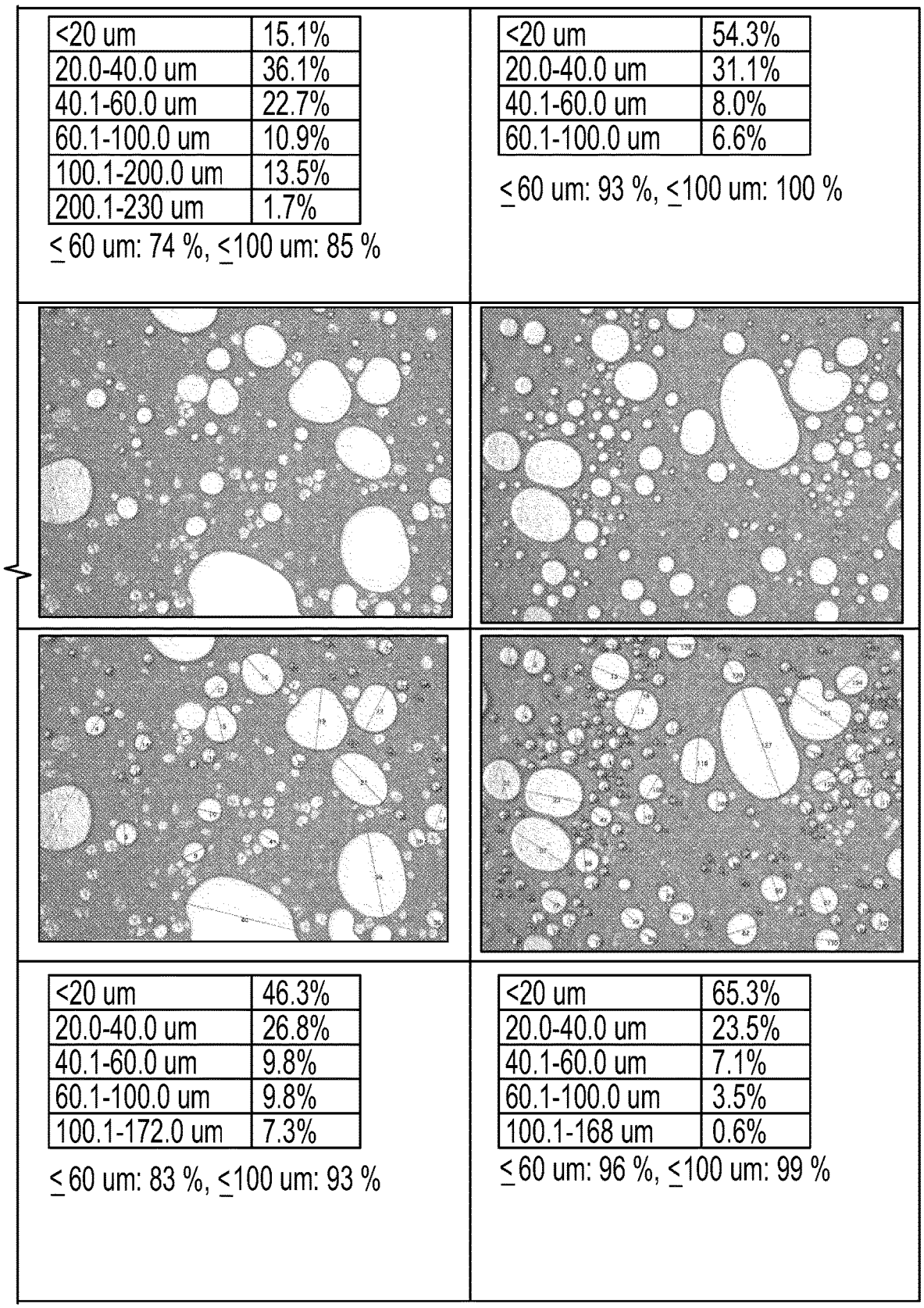

Although "whipped-foam" exposed at RT for 20 minutes results in slight decrease in the number of bubbles and slight increase in bubble size, it still maintains its foam structure as seen in evaluation study III (FIG. 6). In addition, there are no significant differences in the bubbles size and bubble distribution for the samples stored at different storage conditions, indicating that whipped products still maintain the desired "whipped-foam" appearance and characteristics as seen in evaluation studies II and III. Therefore, the results from this study clearly demonstrate that the temperature cycling as well as high temperature exposure have little or no impact on the performance of the whipped products.

3.5. Evaluation Study V: The Size and Distribution of Gas Bubbles in "Whipped-Foam" Delivered from Whipped Sunscreen Products Vs Other Foaming Products In addition to the whipped sunscreen product of this invention, three foaming products are examined microscopically for the size and distribution of gas bubbles, and the obtained results are summarized in FIG. 11.

Figure 12:
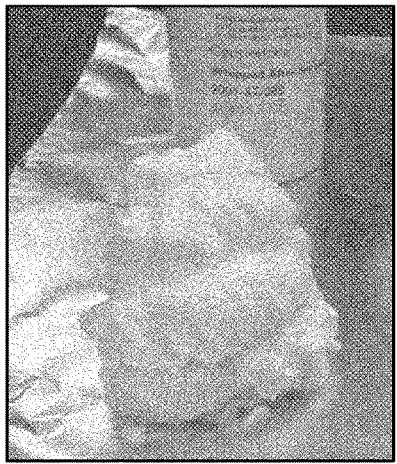
FIG. 12 shows appearance of "Whipped-foam" delivered from a whipped After Sun lotion stored at RT for 3 months.
Figure 15:
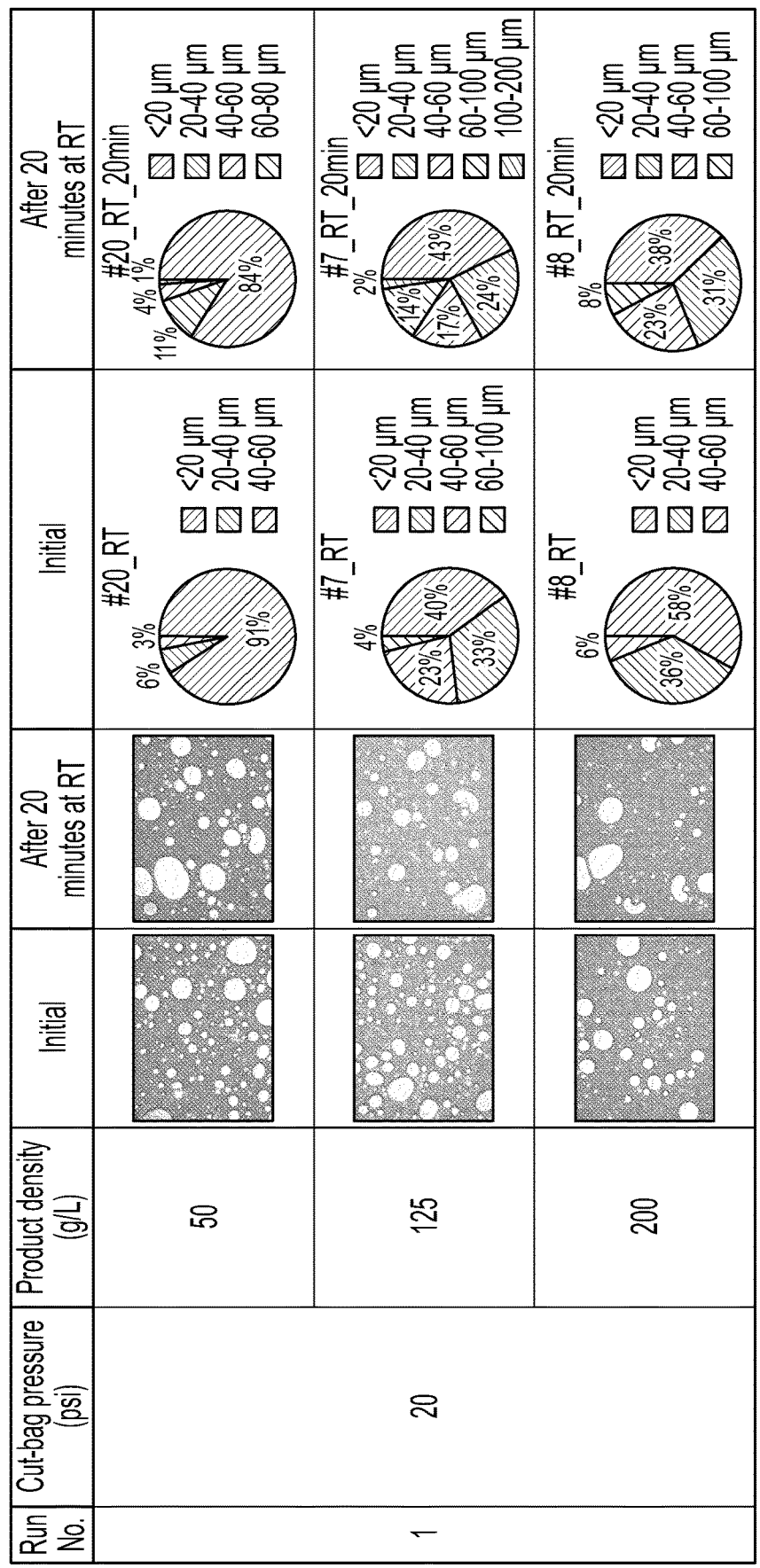
FIG. 15 shows results of bubble size and distribution at various product densities and at 20 psi cut-bag pressure.

Similar to whipped sunscreen products of this invention, whipped After Sun lotion also delivers a voluminous and creamy "whipped-foam" with outstanding spreadability, stay-put-ness, and texture (FIG. 12). However, unlike whipped sunscreen lotion of this invention, limited numbers of gas bubbles are retained. The measured diameters for about 100% of the retained gas bubbles are ≤100 μm, implying that stabilization of gas bubble structure is maintained to some extent.

Few large bubbles are observed in photomicrographs of Waterbabies foaming lotion. The reason of this might be related to the insufficient stabilization of gas bubble structure against Ostwald ripening or coalescence leading to an increase in the bubble size.

The photomicrographic method of measuring gas bubble size is not applicable to whipped cream dispensed from Reddi Wip Original Dairy Whipped Topping because it would drain appreciably during the time of the experiment. That is why no gas bubbles observed for Reddi Wip.

This study shows that whipped sunscreen lotion products offer clear superiority in preventing coalescence of gas bubbles to maintain stable foam structures.

4. CONCLUSIONS

Characteristics of whipped sunscreen products are evaluated. The resulting dispensed "whipped-foam" has rich creamy appearance with excellent features including no tendency to become runny, break down easily, spread evenly on skin, silky smooth texture, and extremely low level of product transfer.

In addition, "whipped-foam" does not drain or collapse fast (resist collapsing at least 30 minutes at RT), allowing more controlled application of the product.

Moreover, whipped sunscreen products are very stable at various storage conditions (RT, Freeze (−10° C.)/Thaw (RT) Cycles (4 cycles), 40° C./20% RH (3 months), and 50° C./75% RH (1 month)) and deliver thermally stable "whipped-foams" that exhibit adequate physical stabilities. Whipped sunscreen products are also able to retain the gas bubbles in a sufficiently compact structure that substantially prevents coalescence of the gas bubbles to maintain stability of the "whipped-foam" even when the product is subjected to multiple heat stress.

Table 4: Formulation Comparison of Whipped Sunscreen Products Used in Evaluation Studies

TABLE 4A

Formulation of Whipped Sunscreen Products (Finished Products)

| Component | Z16-004 (SPF 30) | Z16-006 (SPF 30) | Z16-010 (SPF 50) | Z16-014 (SPF 50) | Z16-071 (SPF 50) | Z16-012 (SPF 50) |
|---|---|---|---|---|---|---|
| COPPERTONE Clearly Sheer Whipped Lotion Concentrate SPF 30 (Y71-128) | 98.10 | — | — | — | — | — |
| COPPERTONE Ultraguard Kids Whipped Lotion Concentrate SPF 30 (Y71-189) | — | 98.10 | — | — | — | — |
| COPPERTONE Clearly Sheer Whipped Lotion Concentrate SPF 50 (Y71-122) | — | — | 98.10 | — | — | — |
| COPPERTONE Ultraguard Kids Whipped Lotion Concentrate SPF 50 (Y71-159) | — | — | — | 98.10 | — | — |
| COPPERTONE Waterbabies Whipped Lotion Concentrate SPF 50 (Z16-001) | — | — | — | — | 98.10 | — |
| COPPERTONE WaterBABIES Whipped Lotion Concentrate SPF 50 (Y71-150) | — | — | — | — | — | 98.10 |
| Nitrous Oxide | 1.90 | 1.90 | 1.90 | 1.90 | 1.90 | 1.90 |

TABLE 4B

Ingredient Formulation of Whipped Sunscreen Lotion Concentrates (Base Formulations)

| Ingredient | Y71-128 (SPF 30) | Y71-189 (SPF 30) | Y71-122 (SPF 50) | Y71-159 (SPF 50) | Z16-001 (SPF 50) | Y71-150 (SPF 50) |
|---|---|---|---|---|---|---|
| Avicel RC-591 | 2.00 | 2.00 | 2.00 | 2.00 | 2.00 | 2.00 |
| Disodium EDTA | 0.10 | 0.10 | 0.10 | 0.10 | 0.10 | 0.10 |
| Ganex P-904 LC | 0.80 | 0.80 | 0.80 | 0.80 | 0.80 | 0.80 |
| Glycerin | 2.50 | 2.50 | 2.50 | 2.50 | 2.50 | 2.50 |
| Sunspheres PGL | 8.00 | 8.00 | 8.00 | 8.00 | 8.00 | 8.00 |
| Octocrylene | 8.00 | 8.00 | 4.00 | 8.00 | 8.00 | 8.00 |
| Octisalate, USP | 4.50 | 4.50 | 4.50 | 4.50 | 4.50 | 4.50 |
| Homosalate | 10.00 | 10.00 | 10.00 | 10.00 | 10.00 | 10.00 |
| Dicaprylyl Ether | 2.00 | 2.00 | 2.00 | 2.00 | 2.00 | 2.00 |
| Tocopherol | 0.25 | 0.25 | 0.25 | 0.25 | 0.25 | 0.25 |
| Avobenzone | 3.00 | 3.00 | 3.00 | 3.00 | 3.00 | 3.00 |
| Oxybenzone | — | — | 6.00 | 6.00 | 6.00 | 6.00 |
| Prolipid 141 | 4.50 | 4.50 | 4.50 | 4.50 | 4.50 | 4.50 |
| Lanette 22 (CM) | 2.00 | 2.00 | 2.00 | 2.00 | 2.00 | 2.00 |
| Cetyl Alcohol | 1.00 | 1.00 | 1.00 | 1.00 | 1.00 | 1.00 |
| Chlorphenesin | 0.27 | 0.27 | 0.27 | 0.27 | 0.27 | 0.27 |
| Sodium Ascorbyl Phosphate | 0.01 | 0.01 | 0.01 | 0.01 | 0.01 | 0.01 |

TABLE 4B-continued

Ingredient Formulation of Whipped Sunscreen Lotion Concentrates (Base Formulations)

| | Concentration (% w/w) | | | | | |
|---|---|---|---|---|---|---|
| Ingredient | Y71-128 (SPF 30) | Y71-189 (SPF 30) | Y71-122 (SPF 50) | Y71-159 (SPF 50) | Z16-001 (SPF 50) | Y71-150 (SPF 50) |
| Benzyl Alcohol | 0.90 | 0.90 | 0.90 | 0.90 | 0.90 | 0.90 |
| Fragrance SZ-1405 MOD 2010 | — | 0.40 | — | 0.40 | — | — |
| Citrus Waters SZ28506 | 0.15 | — | 0.15 | — | — | — |
| Waterbabies 5235646 | — | — | — | — | 0.25 | — |
| Waterbabies #486738 | — | — | — | — | — | 0.25 |
| Dry-Flo Pure | 4.00 | 4.00 | 4.00 | 4.00 | 4.00 | 4.00 |
| Water | Q.S. | Q.S. | Q.S. | Q.S. | Q.S. | Q.S. |

TABLE 5

Information of several topical products evaluated

| Product Description | Lot number | Expiration Date |
|---|---|---|
| Bepanthen ® Baby Moisturizer for Extra Sensitive Skin | 5104G | September 2017 |
| Bepanthen ® Antiseptic Cream (New formulation) | 1032984 | December 2016 |
| Bepanthol ® body Lotion | 1404722 | April 2017 |
| Priorin ® Shampoo For Hair Loss, Dry and Normal Hair | 1507195 | July 2018 |
| Priorin ® Shampoo Revitalising Shampoo for Damaged Dry Hair with Millet | 1310666 | October 2016 |
| Priorin ® Ampules (liquid) | 003G | May 2018 |
| Canesten ® Cream Clotrimazole 1% | BXPJLFP | March 2018 |

Example 4. Technical Feasibility Assessment: A New Whipped Delivery System for Various Topical Products The feasibility of developing a new whipped delivery system for various topical products is evaluated. The scope of work includes manufacture of whipped products using nitrous oxide, feasibility experiments to evaluate whippability of these whipped products, together with spreadability and texture of resultant whipped-foams, and followed by monitoring the stability of whipped-foams. Total of seven topical products of Bepanthen®, Priorin®, and Canesten® brands are selected for these evaluations (Table 4). In general, a whipped product (Finished Product) should be prepared by 1) pre-mixing step: co-process of a Concentrate and a 1st Gas, 2) pre-pressurizing step: pressurizing of a 2nd gas between a bag and the inside wall of the product can, and 3) packaging step: packaging the pre-mixed formulation (concentrate+the 1st gas) into the pre-pressurized Bag on Valve (BOV) package. For this proof of principle study, a pre-pressurized BOV package and the pre-mixing step are not utilized. However, in order to mimic the performance of a typical whipped product, the mixture of each topical product (98.10% w/w) and nitrous oxide (1.90% w/w) in a package is shaken vigorously before dispensing to ensure a fine dispersion of nitrous oxide in the each topical product (continuous medium).

All products except Priorin® Ampules are found to be whippable without any formulation optimization or process optimization (FIG. 13). Among whippable products, three topical products (Bepanthen® Baby Moisturizer, Bepanthol® body Lotion, and Canesten® Cream) produce whipped-foams having excellent spreadability with smooth texture. The resultant whipped-foams are further evaluated for their stability at room temperature (RT). As shown in FIG. 14, whipped-foams dispensed from whipped products containing two Priorin® Shampoos are not stable at RT. Acceptable whipped-foam stability is observed for whipped products containing Bepanthen® Baby Moisturizer, Bepanthen® Cream, Bepanthol® body Lotion, and Canesten® Cream. Based on the results, it appears that three Priorin® products tested would not meet the requirements for a whipped delivery system without significant formulation modifications. In addition, the current Bepanthen® Cream would not offer clear superiority in spreadability and texture attributes of the resultant whipped-foam. However, the formulation would be able to be modified to improve whipped characteristics and spreadability.

Example 5. Other Products have been Shown to be Whippable, for Example and without Limitation Category—Class—Whipped Benefit
  Whip Cream—Food—Anti-Abuse
  Peanut Butter—Food—Ease of Application
  Dessert Topping—Food—Ease of Application
  Topical Analgesic—OTC Drug—Improved Absorption
  Burn Cream—Medical Device Rx—Reduced Spreadability Pain
  Medical Haircare—Hair loss—NDA—Reduced Consumer Complaints—Failure to empty
  Medical Haircare—Scalp treatment—OTC Drug—Improved Delivery/Application
  Petrolatum Gel—OTC Drug—Ease of Application
  Hair Styling Product—Cosmetic—Novel Delivery of Thicker Products
  Diaper Rash Prevention—OTC Drug—Novel Delivery of Thicker Products
  Tooth Whitener—Cosmetic—Better Coverage
  Oral Care—Toothpaste—Cosmetic—Improved Delivery
  Anti-Fungal treatment—OTC/Rx Drug—Reduced Spread-ability Pain/Improved Absorption
  Eye-lid Cleanser—Cosmetic—Novel Delivery
  Psoriasis treatment—Medical Device—Reduced Spreadability Pain Colon-Rectal Treatment—Rx—Improved Drug Delivery and Absorption
Acne treatment—OTC Drug—Novel Delivery
Hand Sanitizer—OTC Drug—Formulation Approach
Natural Deodorant—Cosmetic—Improved Spread-ability
Shave Prep—Cosmetic—Novel Delivery of Thicker Products
Wound Care—Medical Device—Novel Delivery of Thicker Products
Self-Tanner—Cosmetic—Improved Delivery
Body Moisturizer—Cosmetic—Novel Delivery of Thicker Products
Lice Treatment—Medical Device/OTC—Novel Delivery of Thicker Products
Hair Depilatory—OTC Drug—Novel Delivery of Thicker Products
Anti-Hemorrhagic—Rx/Device—Formulation Compatibility—Non-Flammability—Surgical Application.

Example 6 Physical Characteristics Due to Changes in Gas Loading and Pre-Gas Pressure Example 6A Two intertwined process variables may contribute to controlling the consumer experience associated with a whipped formulation: (1) gas loading (e.g., Nitrous Oxide), which impacts density, spreadability, sound profile during dispensing, and physical appearance of product; and (2) pre-gas can pressure, which influences stability of gas emulsion, sound, speed of dispense, sputtering, and "quality" characteristics. Multiple product variants, combining these two process variables, were run and were being physically evaluated. Physical measurements were made, including CT scans, to yield "in can" product profile characterization details; dispensing observations (appearance, sound, etc.) and high temperature foam stability; and post-dispensing physical measurements including density, bubble size, and bubble size distribution.

Nine formulations manufactured at various process conditions, representing the practical range of "cut bag" (pre-gas) pressure and nitrous oxide loading, shown in Tables 6, 8, 9, and 10, were tested.

TABLE 6

| | | Cut Bag Pressure (psi) | | |
|---|---|---|---|---|
| | | 20 | 32.5 | 45 |
| Product Density g/L | 50 | X | X | X |
| | 125 | X | X | X |
| | 200 | X | X | X |

Each variable combination sampled was evaluated via a CT Scanner to determine bubble size and bubble size distribution while remaining in-can and under elevated pressure. The results are shown in FIGs. The samples were then evaluated after dispensing across a wide range of factors including appearance, bubble size and distribution, and high temperature foam stability. The results are shown in FIGS. 15-38.

Figure 16:
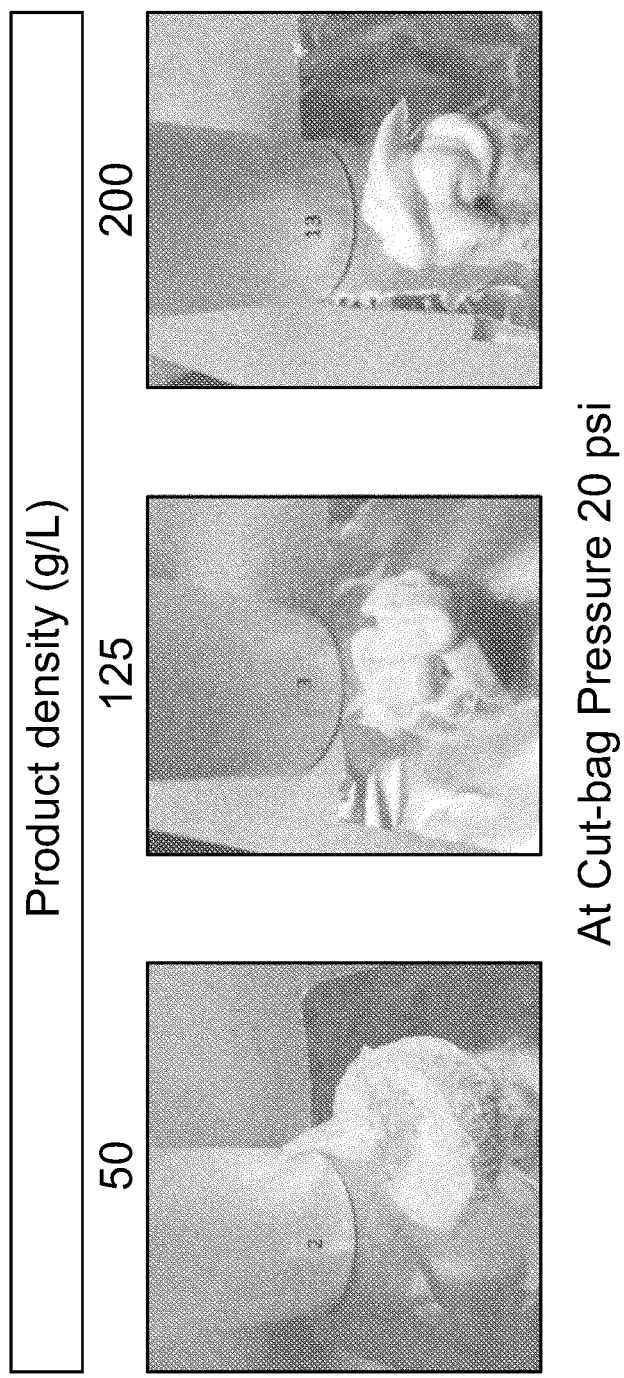
FIG. 16 shows appearance of "whipped foam" at various product densities and at 20 psi cut-bag pressure.

Some post-dispensed results are:

Appearance of "whipped foam": richer, more voluminous appearance at lower product density (FIG. 16).

Figure 17:
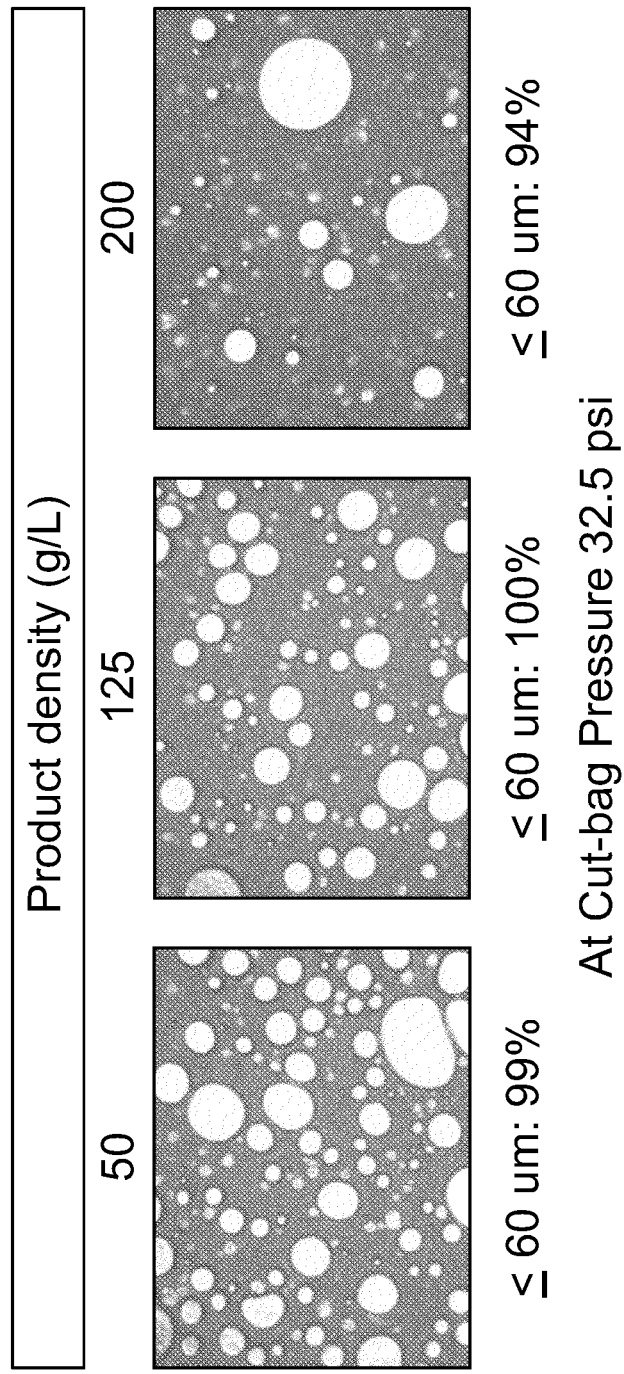
FIG. 17 shows results of bubble size and distribution at various product densities and at 32.5 psi cut-bag pressure. Lower product density leads to higher levels of small bubbles.

Gas bubble size and distribution: lower product density leads to higher levels of small bubbles (FIG. 17).

Figure 18:
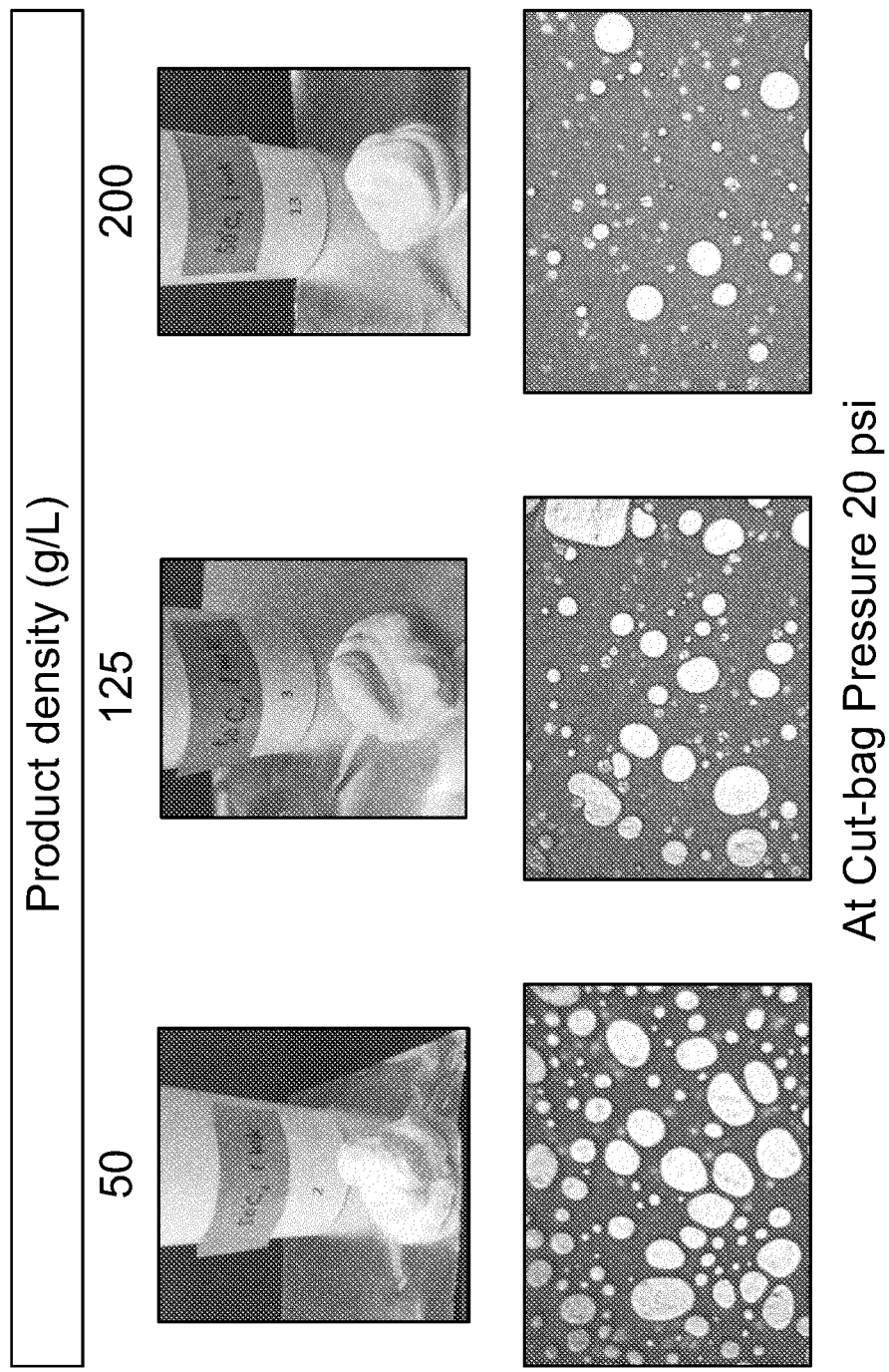
FIG. 18 shows results of high temperature stability (50° C.) at various product densities and at 20 psi cut-bag pressure.
Figure 19:
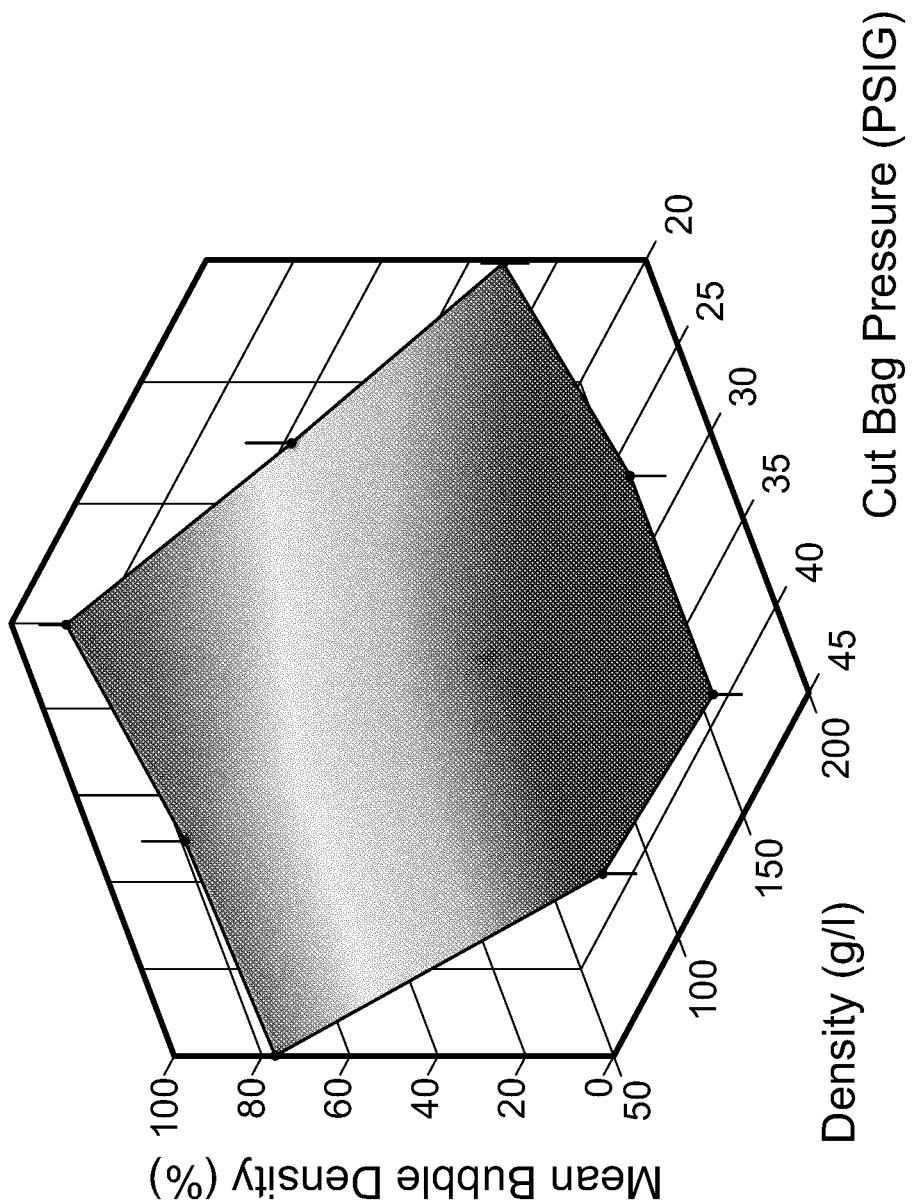
FIG. 19 shows bubble density as at various product densities and cut-bag pressures. Average distribution of bubbles sampled every 0.625 mm through the fluid normalized by total fluid volume.
Figure 20:
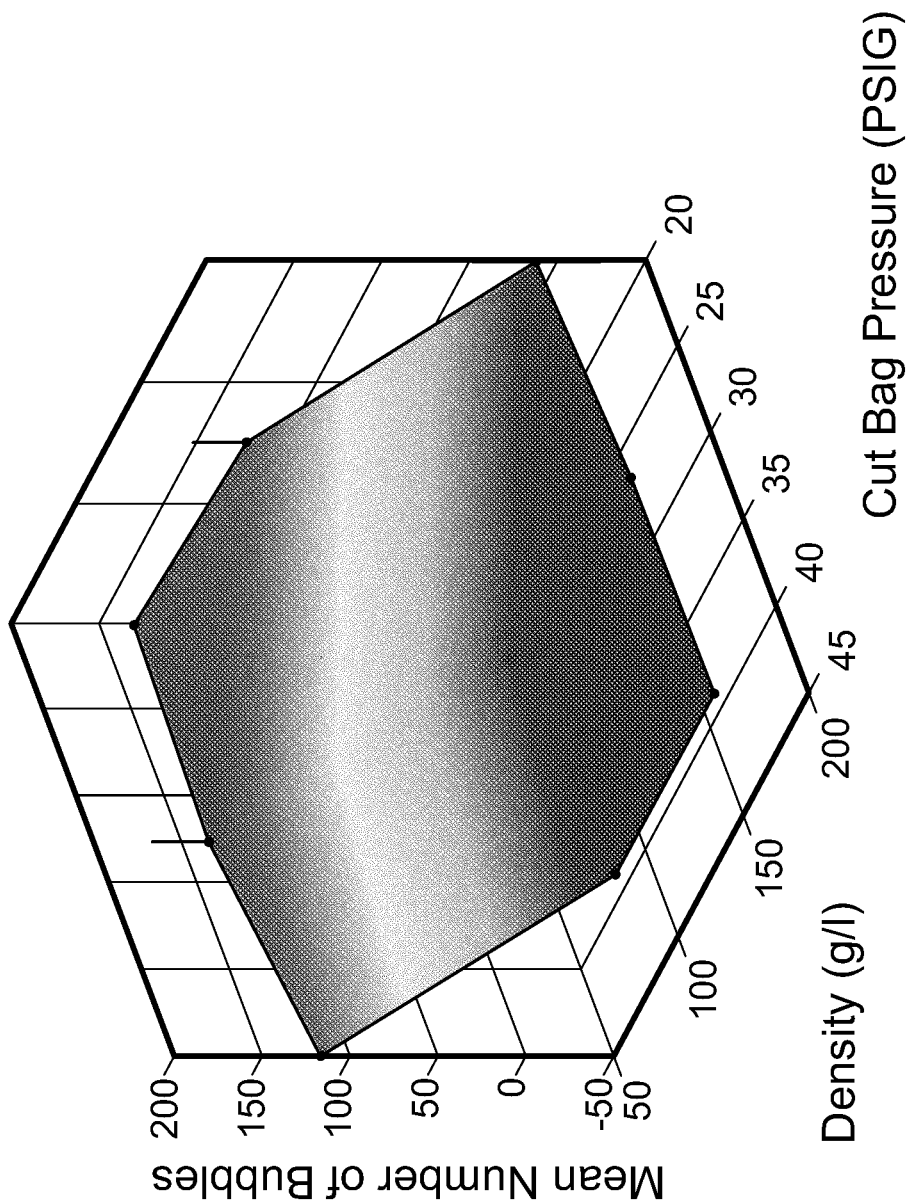
FIG. 20 shows number of bubbles at various product densities and cut-bag pressures. Average distribution of bubbles sampled every 0.625 mm through the fluid normalized by total fluid volume.
Figure 21:
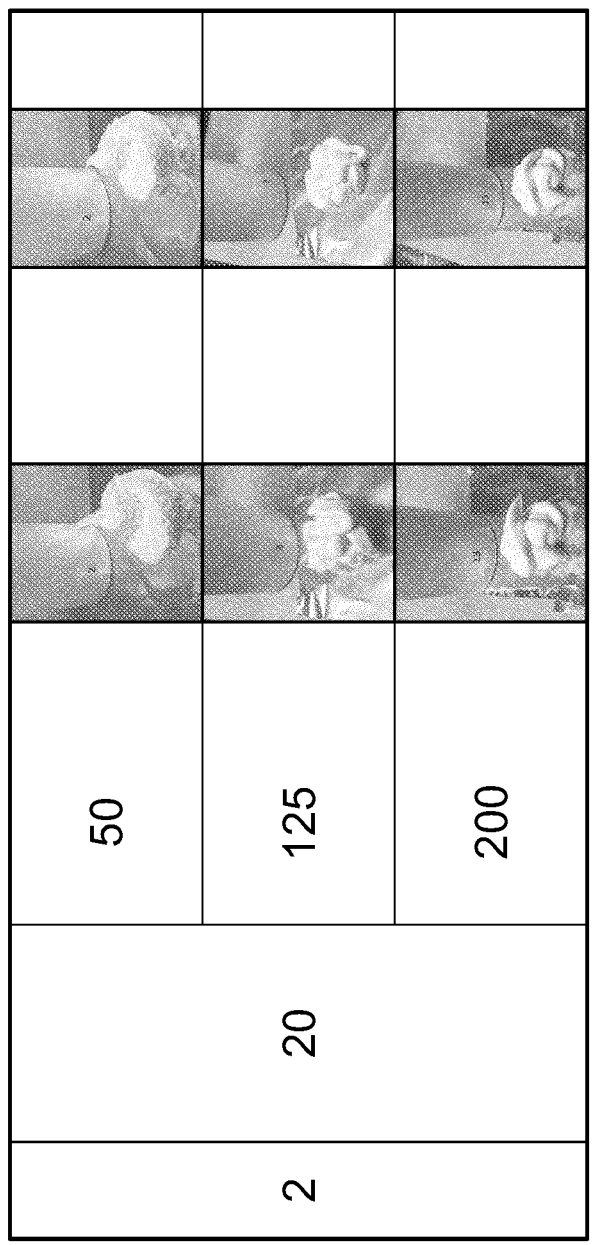
FIG. 21 shows appearances of "whipped-foam" delivered from whipped sunscreen samples manufactured at cut-bag pressure 20 psi with various product densities.
Figure 22:
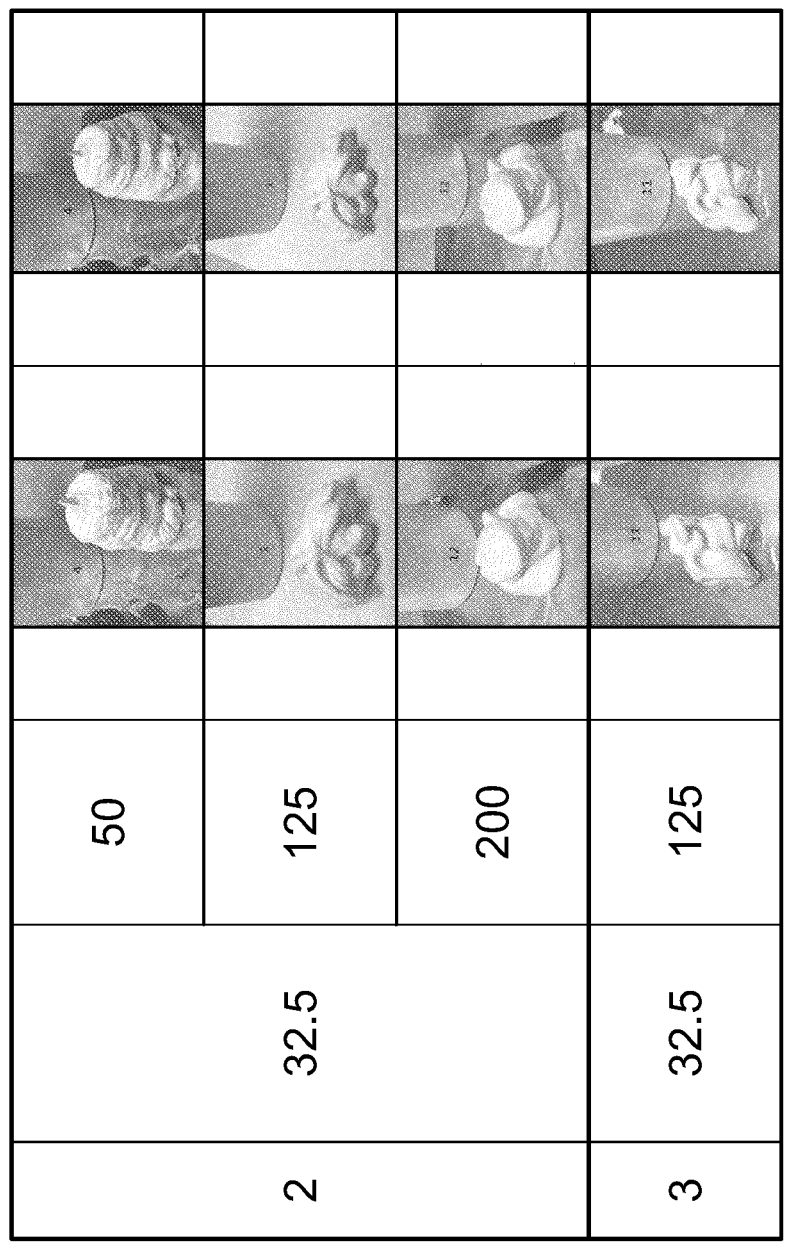
FIG. 22 shows appearances of "whipped-foam" delivered from whipped sunscreen samples manufactured at cut-bag pressure 32.5 psi with various product densities.
Figure 23:
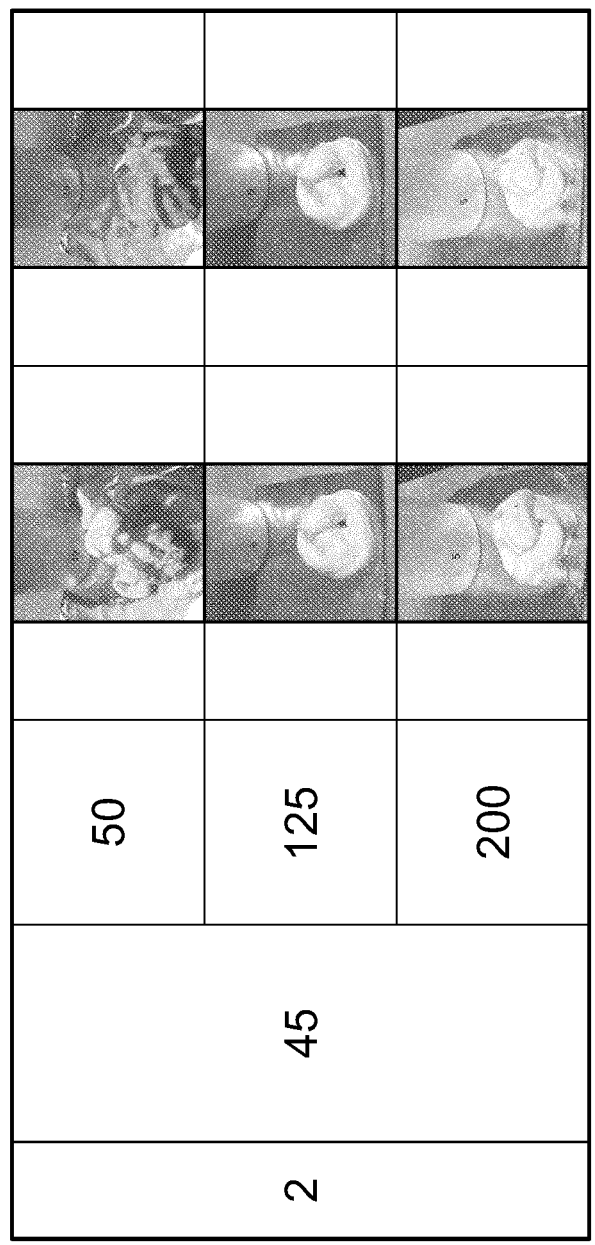
FIG. 23 shows appearances of "whipped-foam" delivered from whipped sunscreen samples manufactured at cut-bag pressure 45 psi with various product densities.
Figure 24:
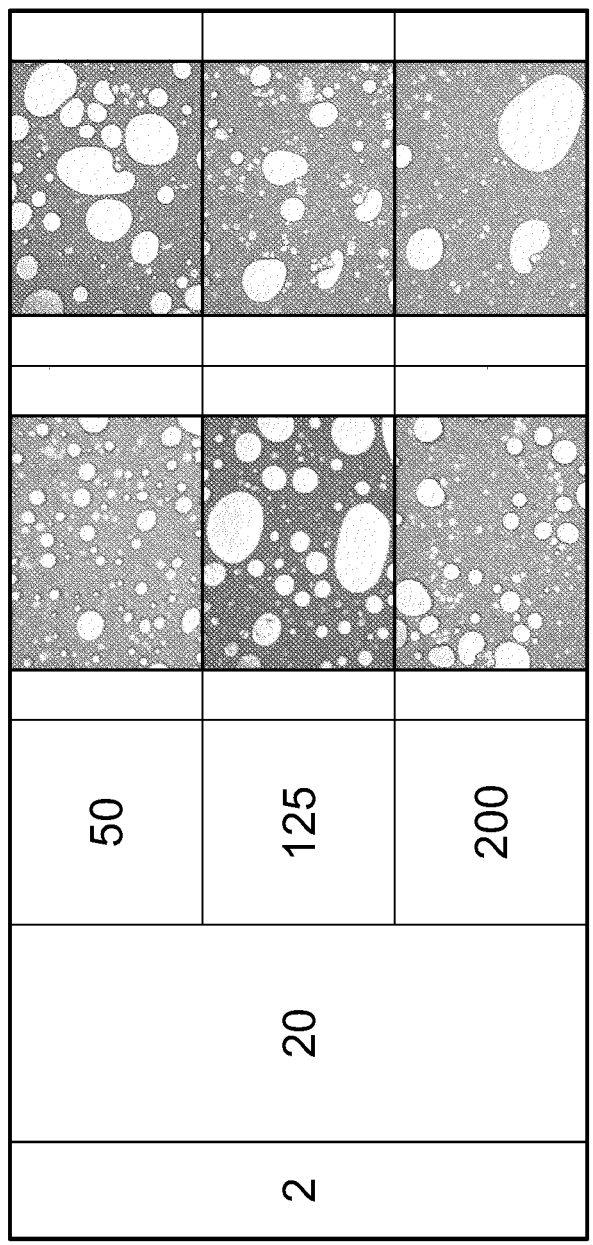
FIG. 24 Photomicrographs (at 500× magnification): Images of gas bubbles ($N_2O$) in "whipped-foam" delivered from whipped sunscreen samples manufactured at cut-bag pressure 20 psi with various product densities.
Figure 25:
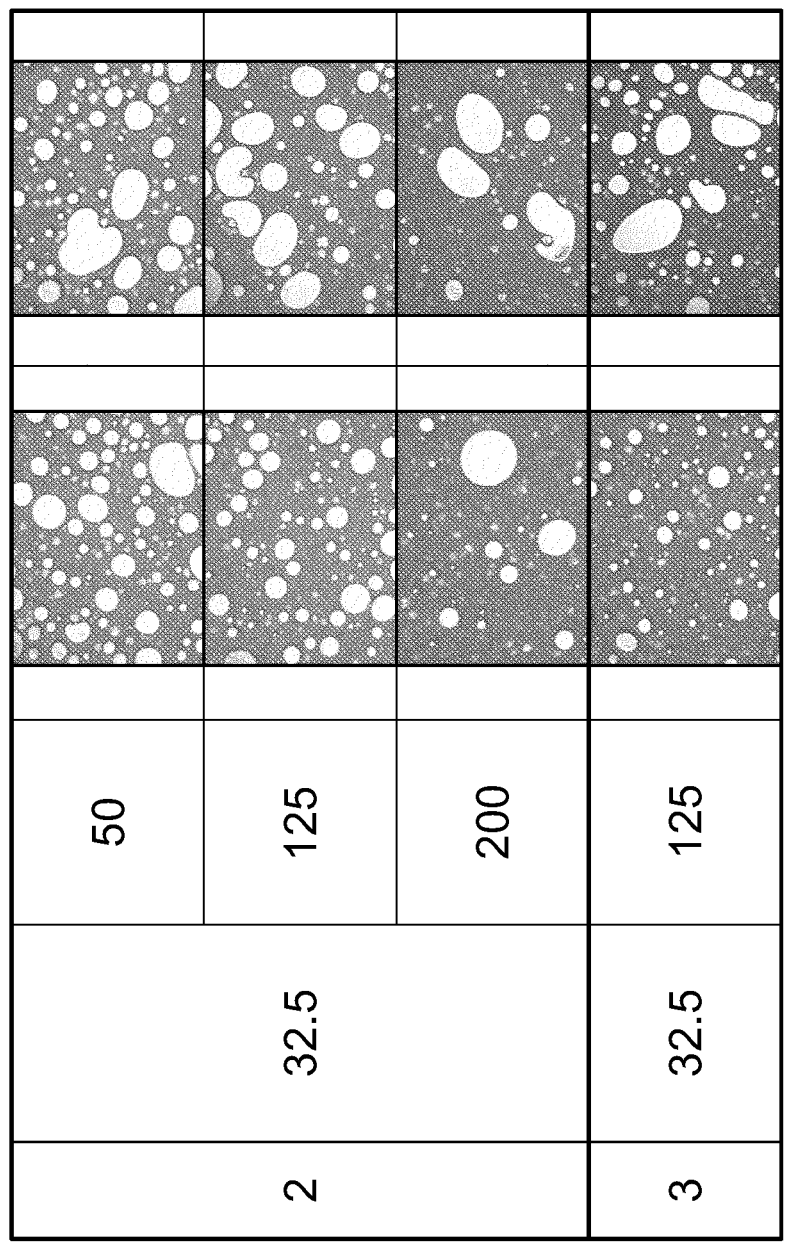
FIG. 25 Photomicrographs (at 500× magnification): Images of gas bubbles ($N_2O$) in "whipped-foam" delivered from whipped sunscreen samples manufactured at cut-bag pressure 32.5 psi with various product densities.
Figure 26:
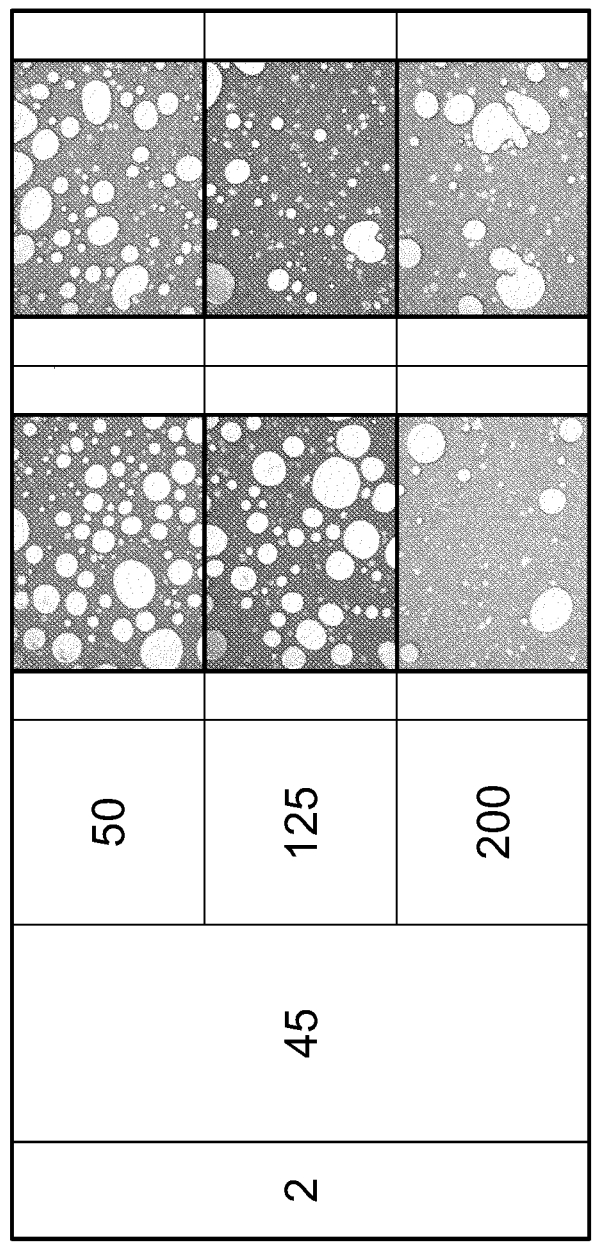
FIG. 26 Photomicrographs (at 500× magnification): Images of gas bubbles ($N_2O$) in "whipped-foam" delivered from whipped sunscreen samples manufactured at cut-bag pressure 45 psi with various product densities.
Figure 27:
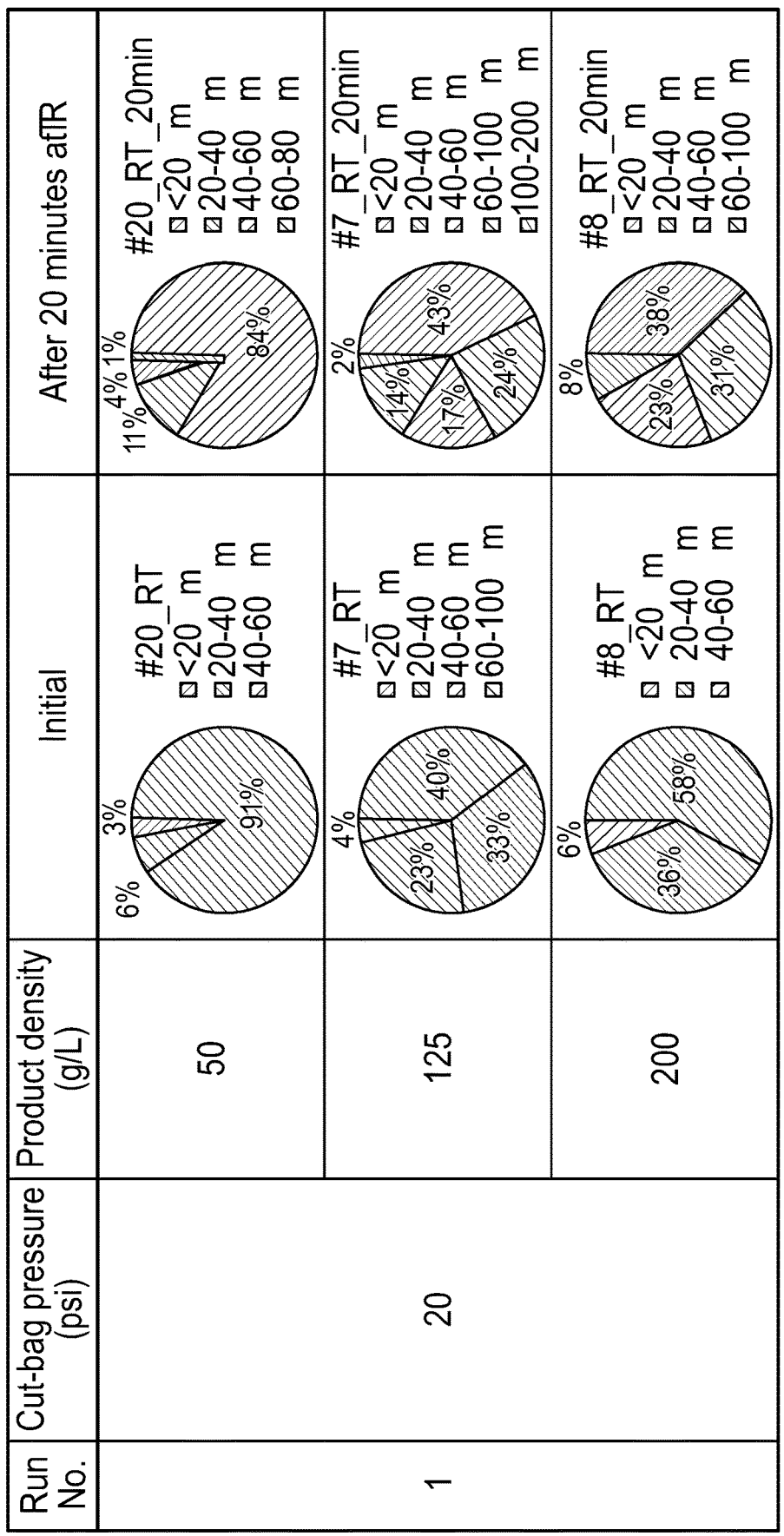
FIG. 27 Distribution of gas bubbles ($N_2O$) in photomicrographs (at 500× magnification) for "whipped-foam" delivered from whipped sunscreen samples manufactured at cut-bag pressure 20 psi with various product densities.
Figure 27:
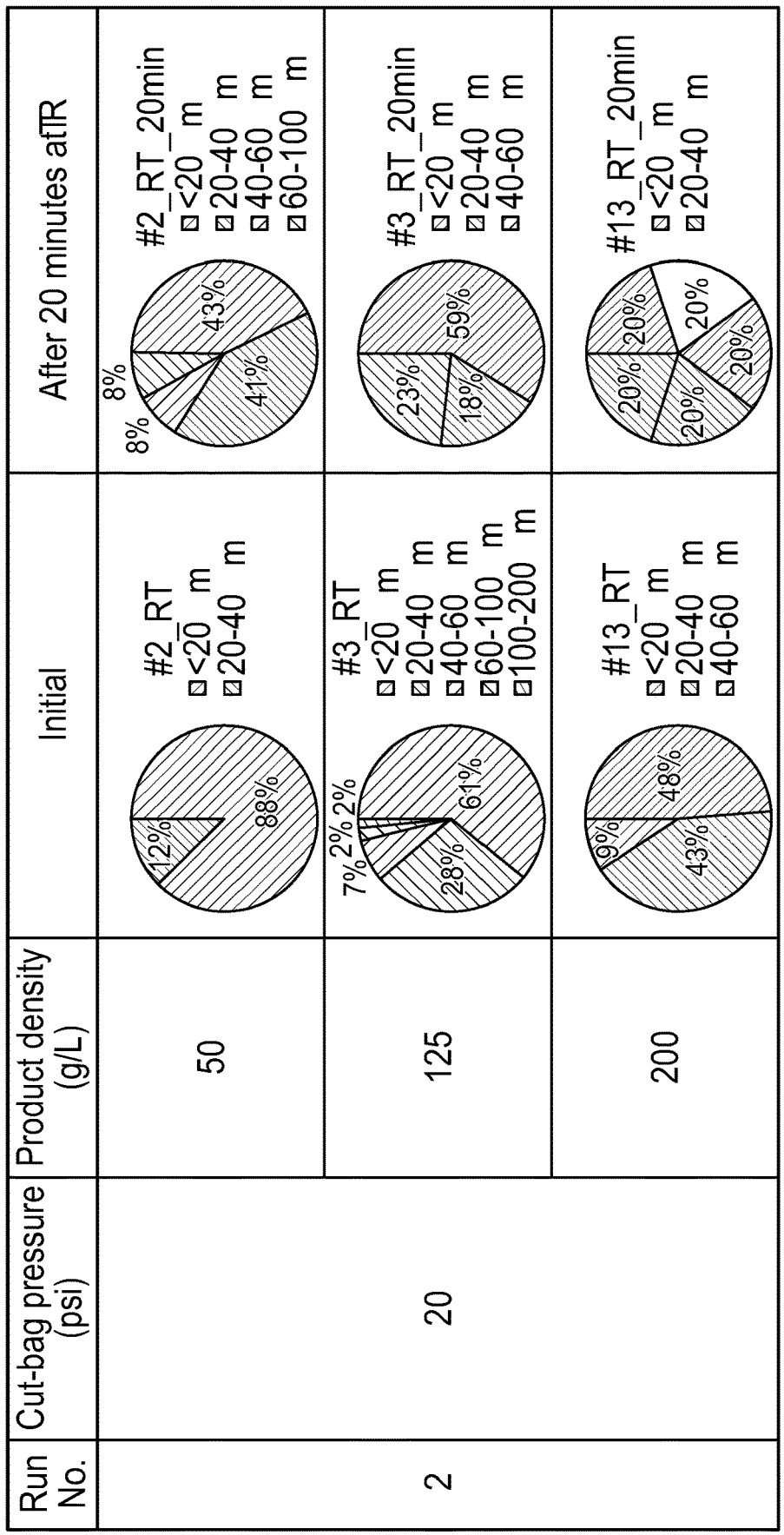
Figure 28:
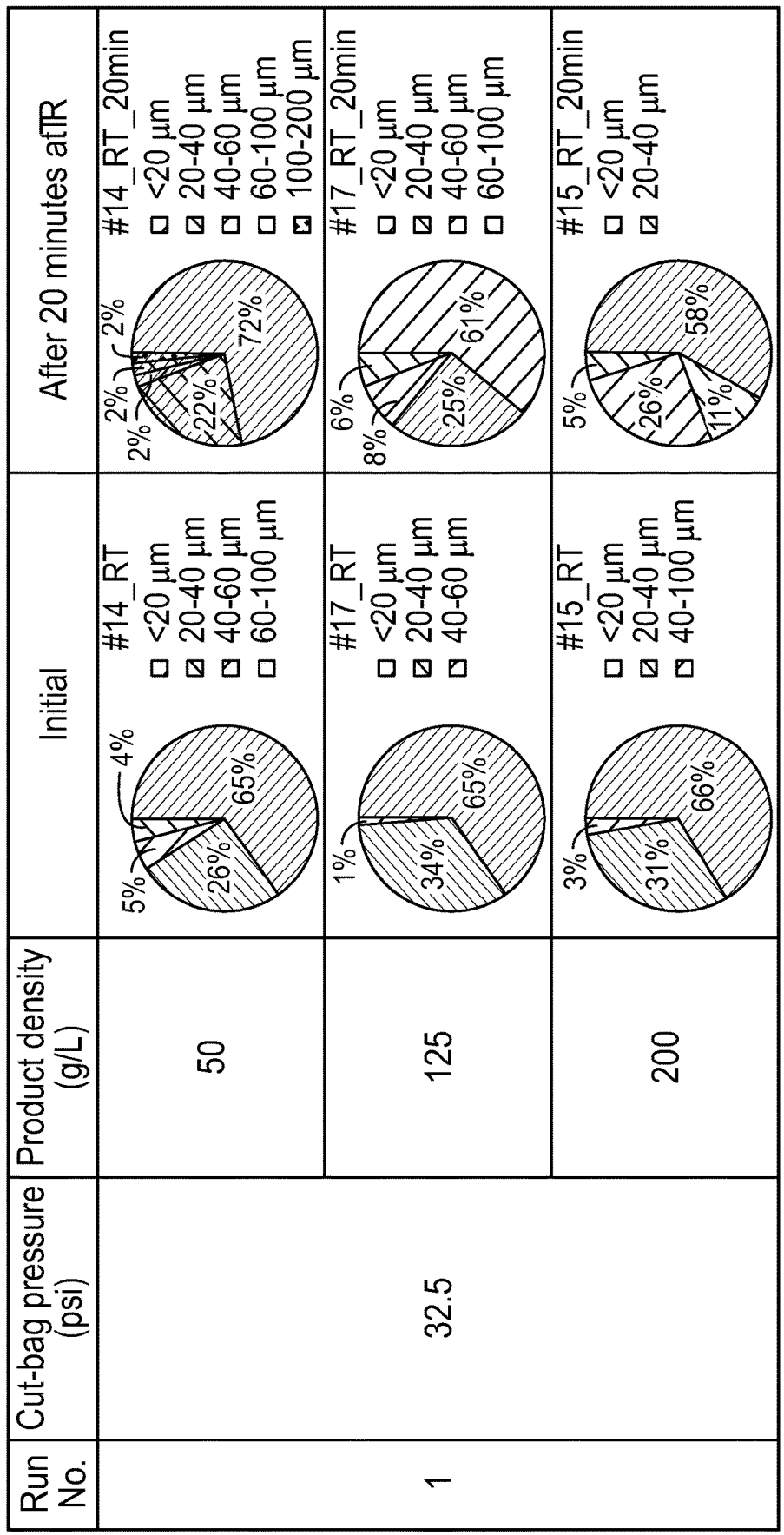
FIG. 28 Distribution of gas bubbles ($N_2O$) in photomicrographs (at 500× magnification) for "whipped-foam" delivered from whipped sunscreen samples manufactured at cut-bag pressure 32.5 psi with various product densities.
Figure 28:
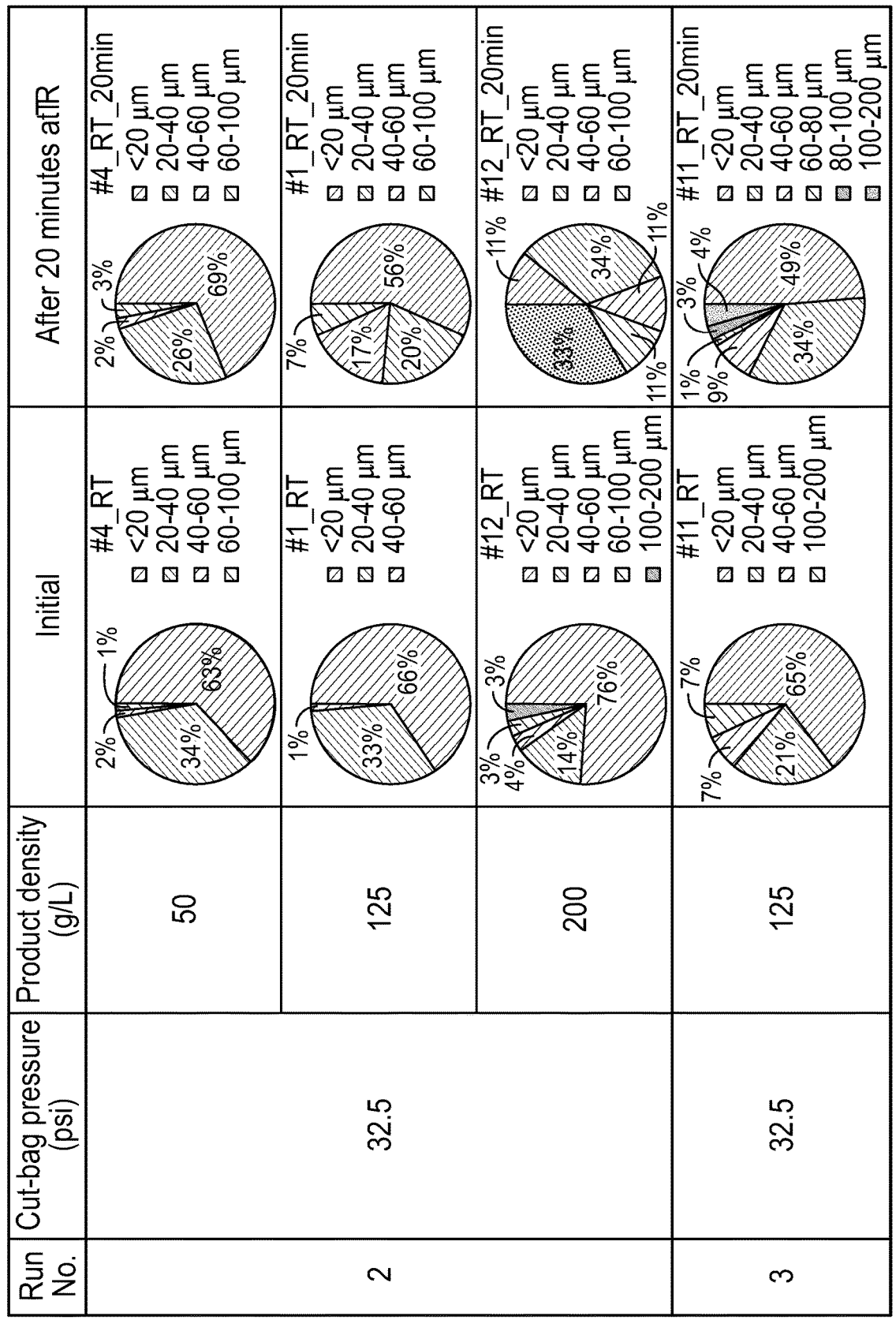
Figure 29:
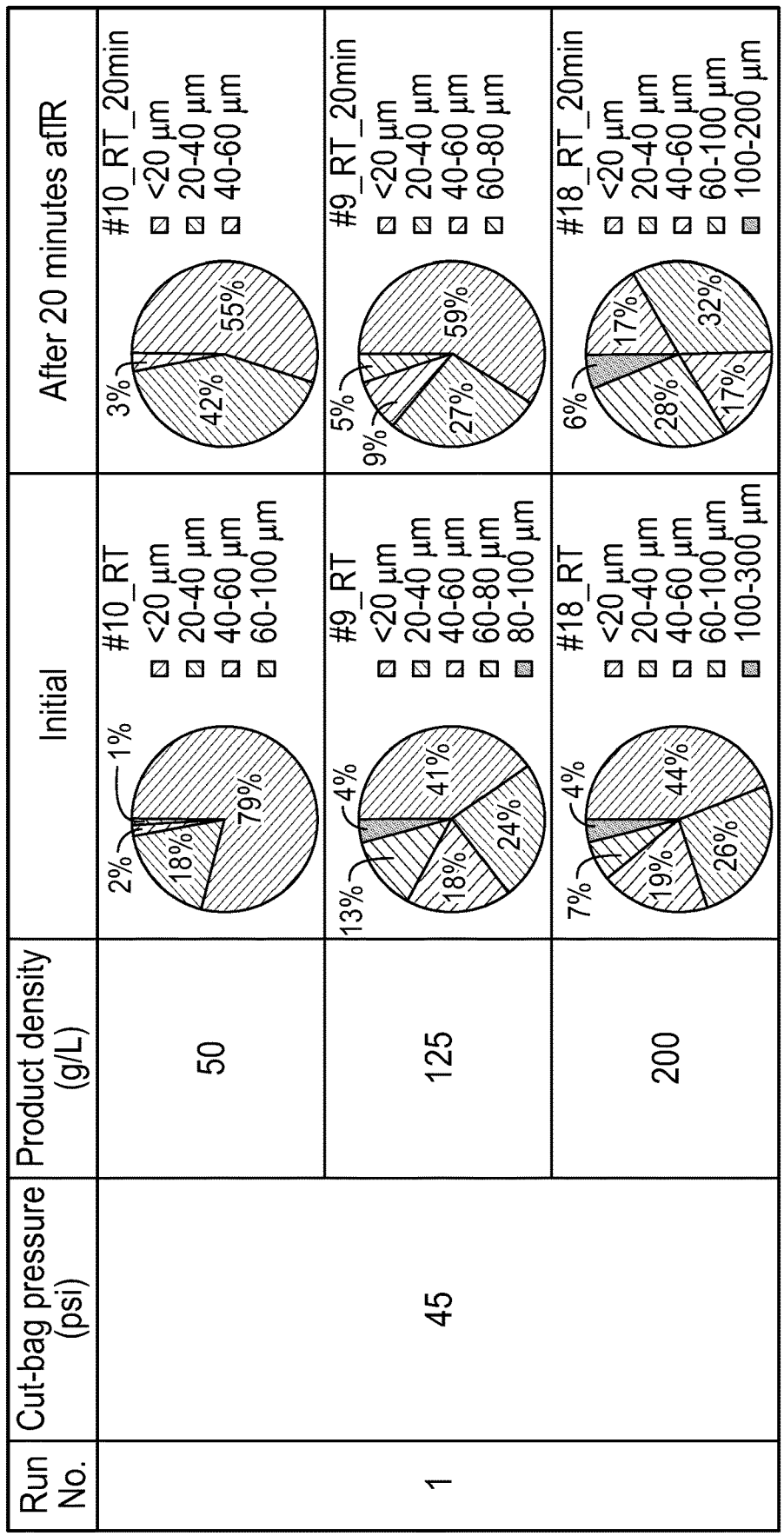
FIG. 29 Distribution of gas bubbles ($N_2O$) in photomicrographs (at 500× magnification) for "whipped-foam" delivered from whipped sunscreen samples manufactured at cut-bag pressure 45 psi with various product densities.
Figure 29:
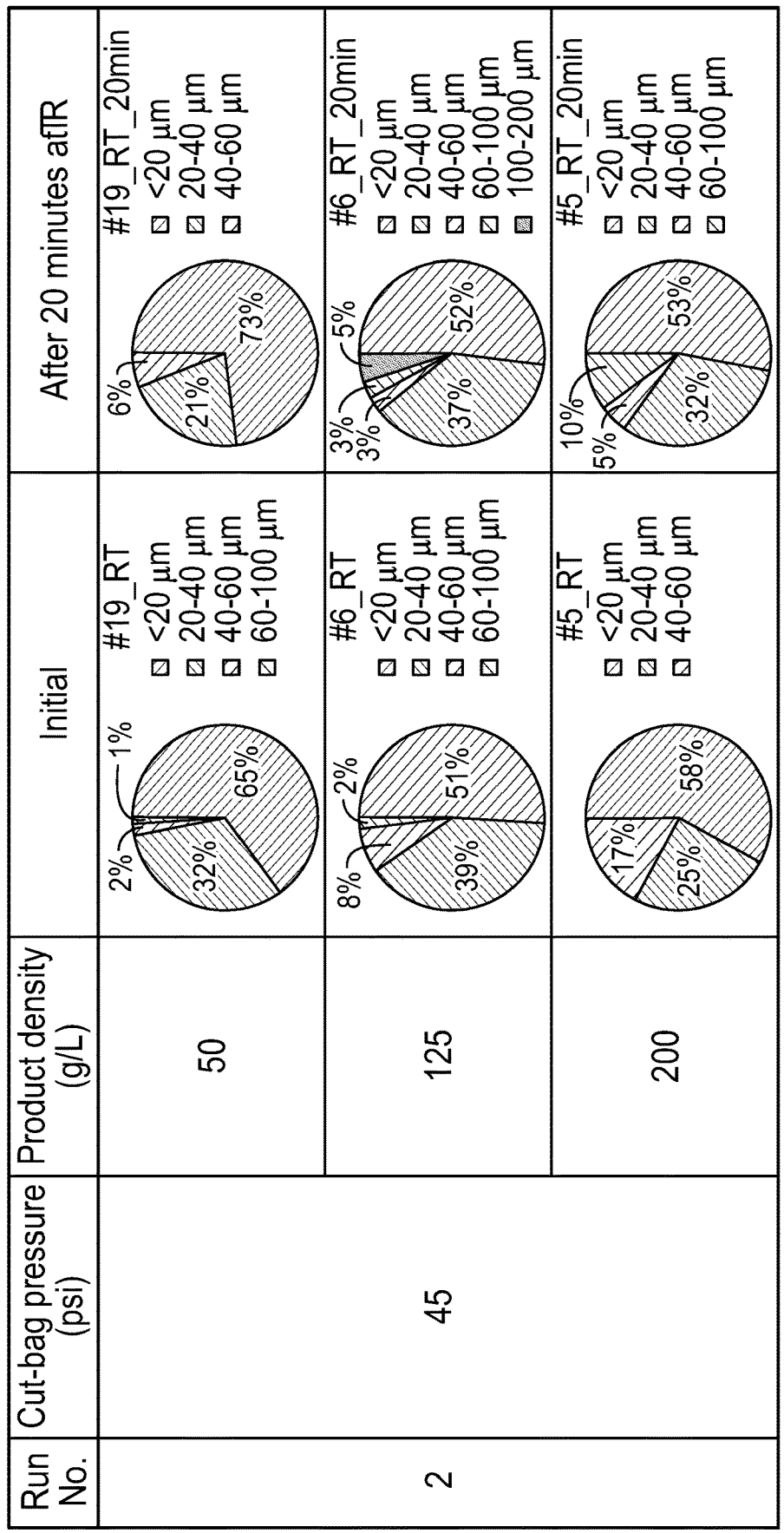
Figure 30:
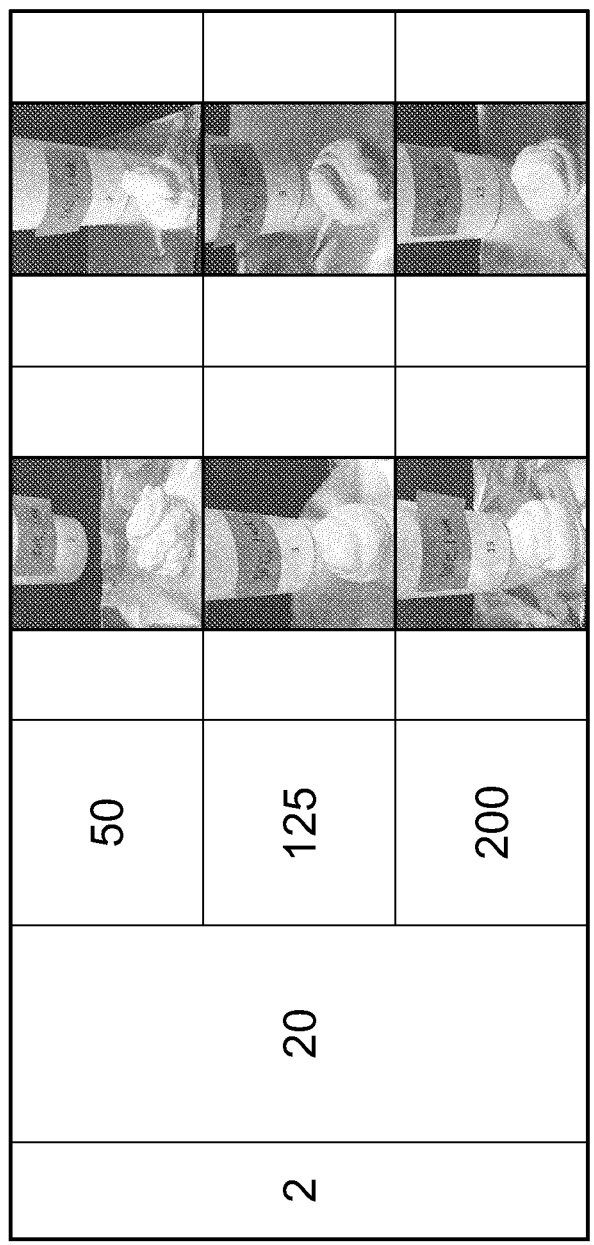
FIG. 30 Appearances and stabilities of "whipped-foam" delivered from whipped sunscreen lotion samples (manufactured at cut-bag pressure 20 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 31:
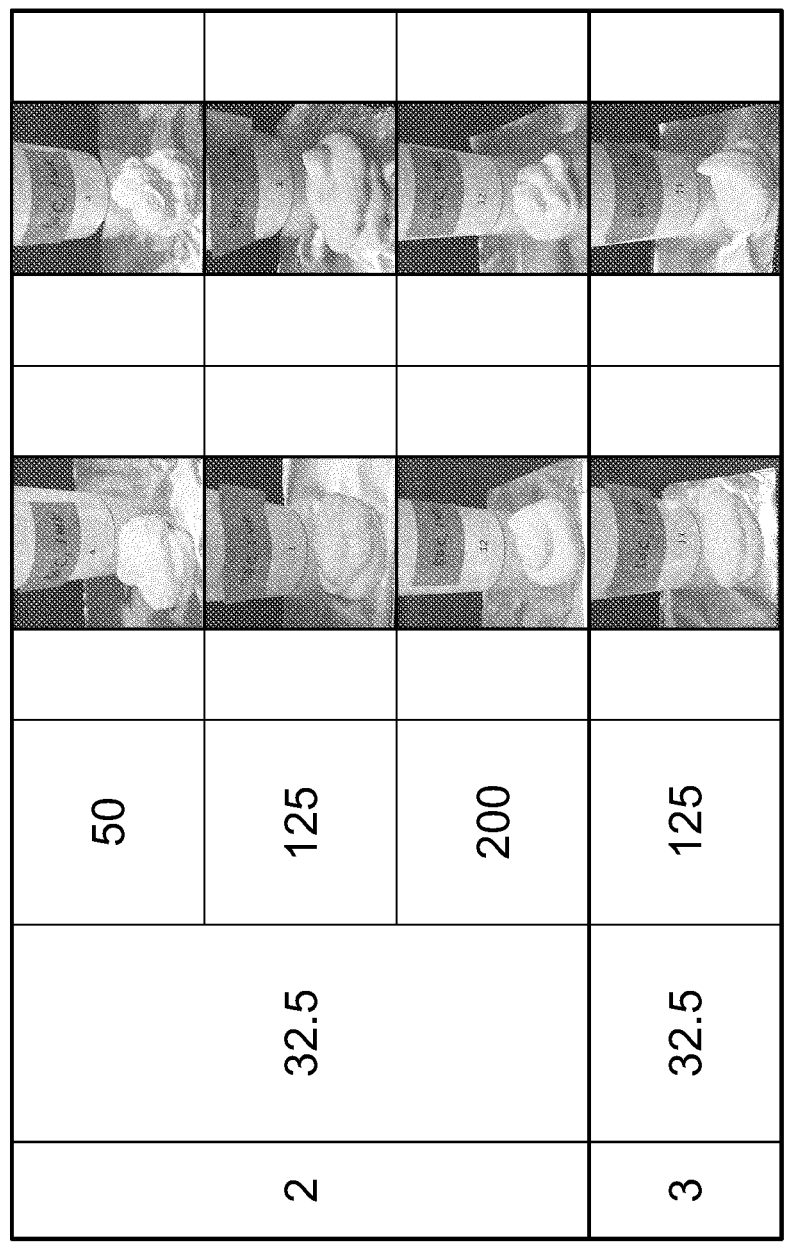
FIG. 31 Appearances and stabilities of "whipped-foam" delivered from whipped sunscreen lotion samples (manufactured at cut-bag pressure 32.5 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 32:
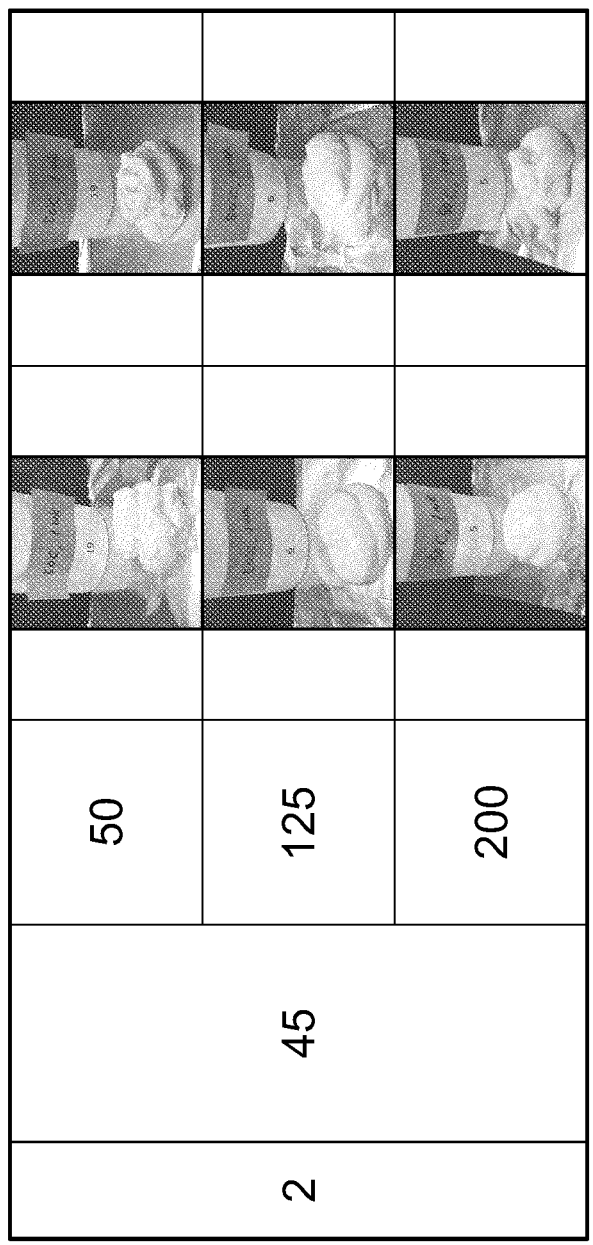
FIG. 32 Appearances and stabilities of "whipped-foam" delivered from whipped sunscreen lotion samples (manufactured at cut-bag pressure 45 psi with various product densities), which had been stored at 50° C./75% RH for 1 week. *T=0 pictures were taken right after pulling out the samples from 50° C./75% RH storage condition and the temperature of each sample was close to 50° C. when the 'whipped-foam" was dispensed; T=2 min pictures taken 2 minutes later.
Figure 33:
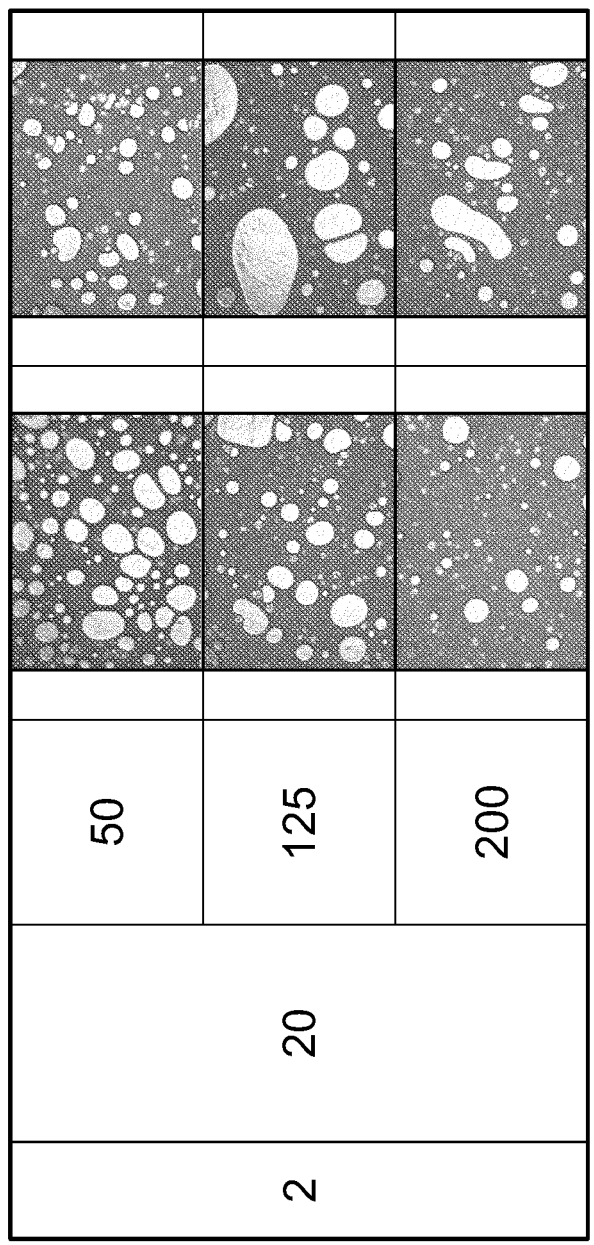
FIG. 33 Photomicrograph (at 500× magnification): Images of gas bubbles ($N_2O$) in "whipped-foam" delivered from whipped sunscreen lotion samples (manufactured at cut-bag pressure 20 psi with various product densities), which had been stored at 50° C./75% RH for 1 week.
Figure 34:
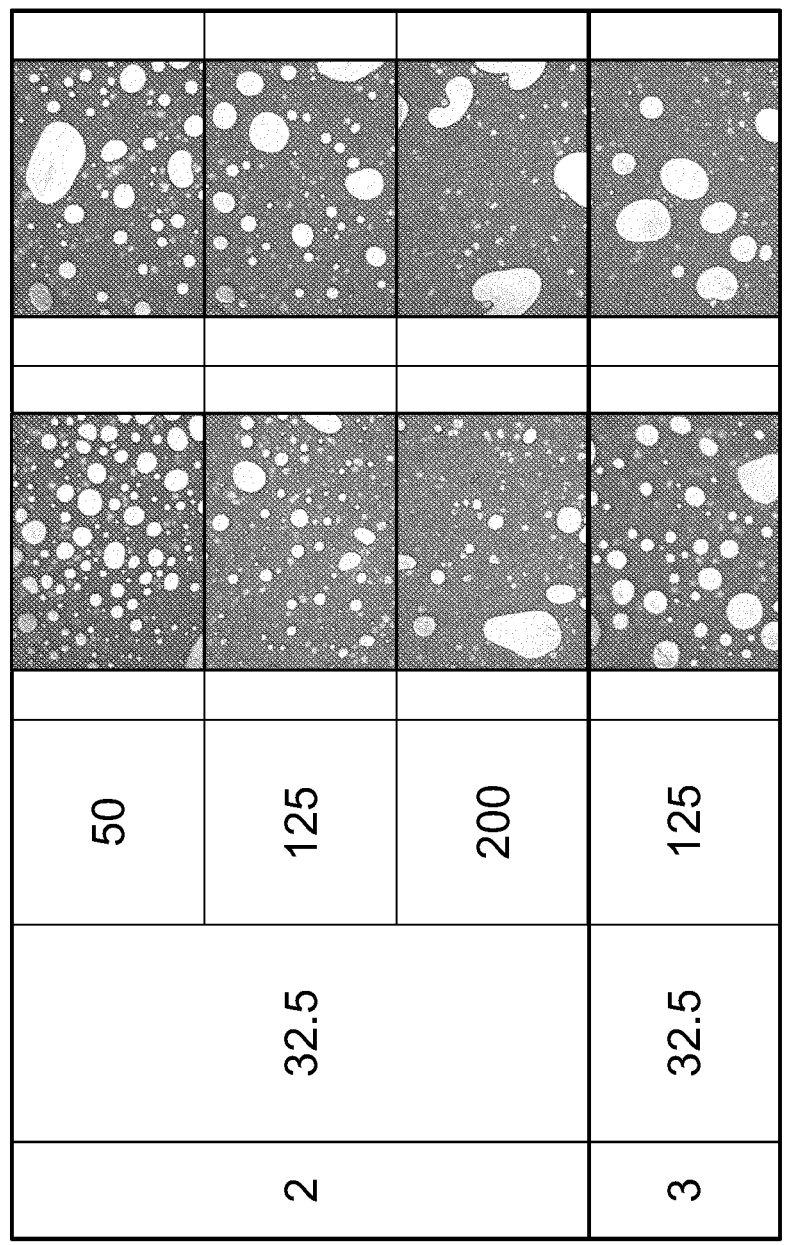
FIG. 34 Photomicrograph (at 500× magnification): Images of gas bubbles ($N_2O$) in "whipped-foam" delivered from whipped sunscreen lotion samples (manufactured at cut-bag pressure 32.5 psi with various product densities), which had been stored at 50° C./75% RH for 1 week.
Figure 35:
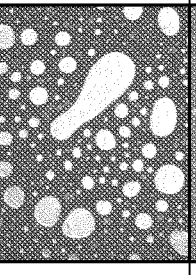
FIG. 35 Photomicrograph (at 500× magnification): Images of gas bubbles ($N_2O$) in "whipped-foam" delivered from whipped sunscreen lotion samples (manufactured at cut-bag pressure 45 psi with various product densities), which had been stored at 50° C./75% RH for 1 week.
Figure 35:
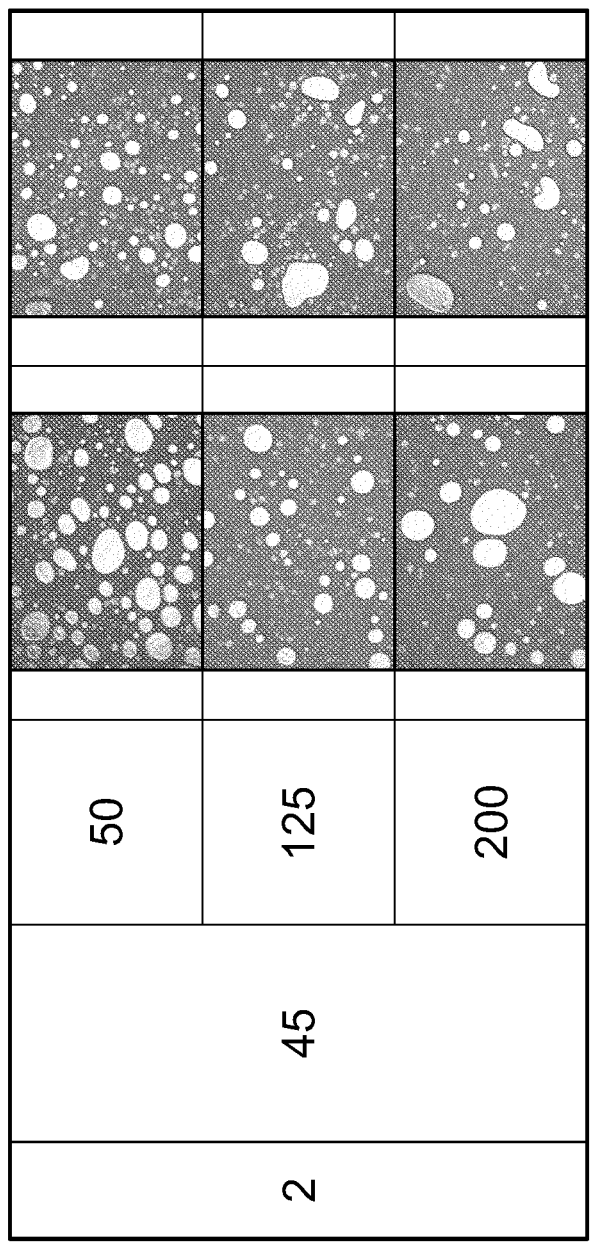
Figure 36:
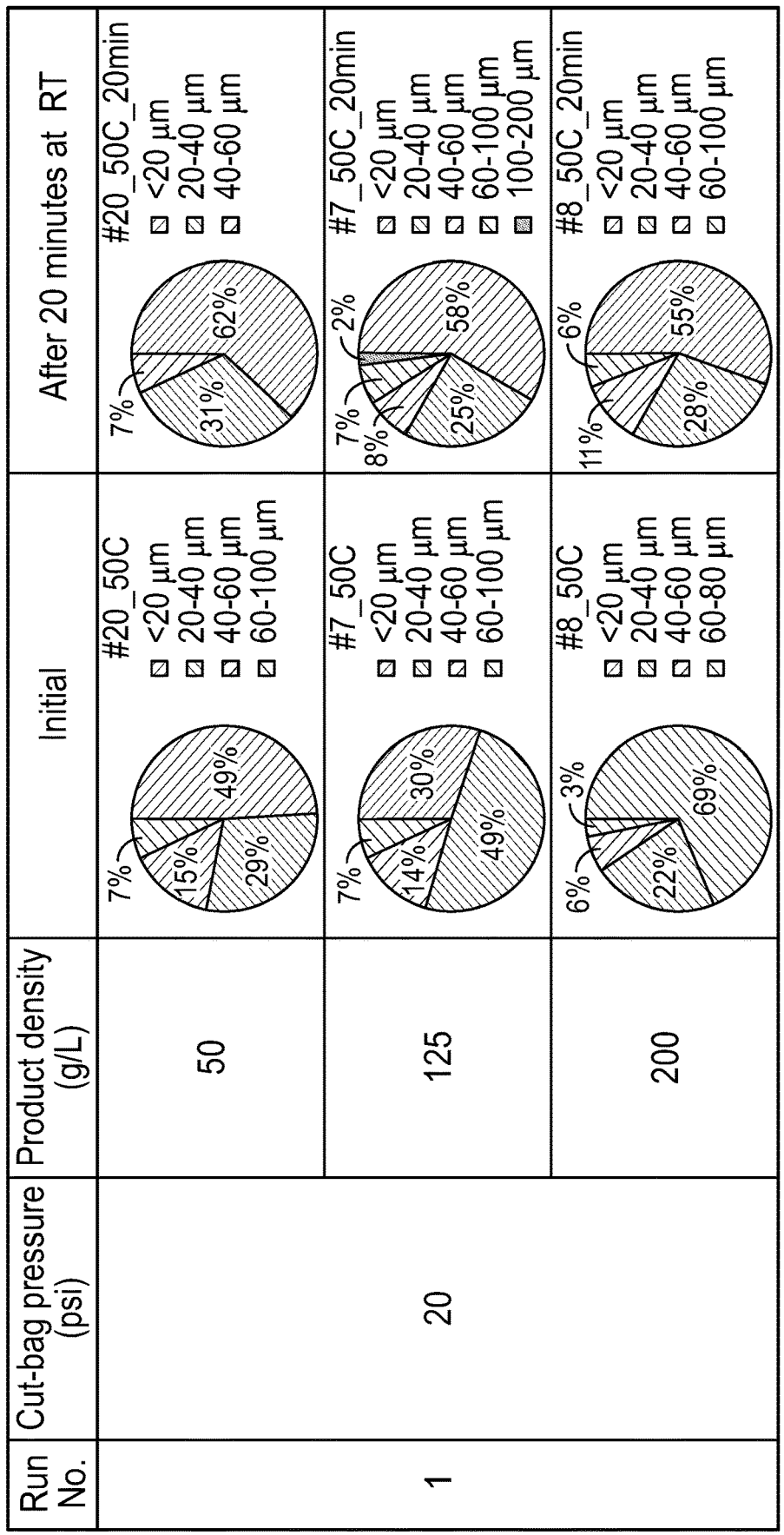
FIG. 36 Distribution of gas bubbles ($N_2O$) in photomicrographs (at 500× magnification) for "whipped-foam" delivered from whipped sunscreen samples (manufactured at cut-bag pressure 20 psi with various product densities), which had been stored at 50° C./75% rh for 1 week.
Figure 36:
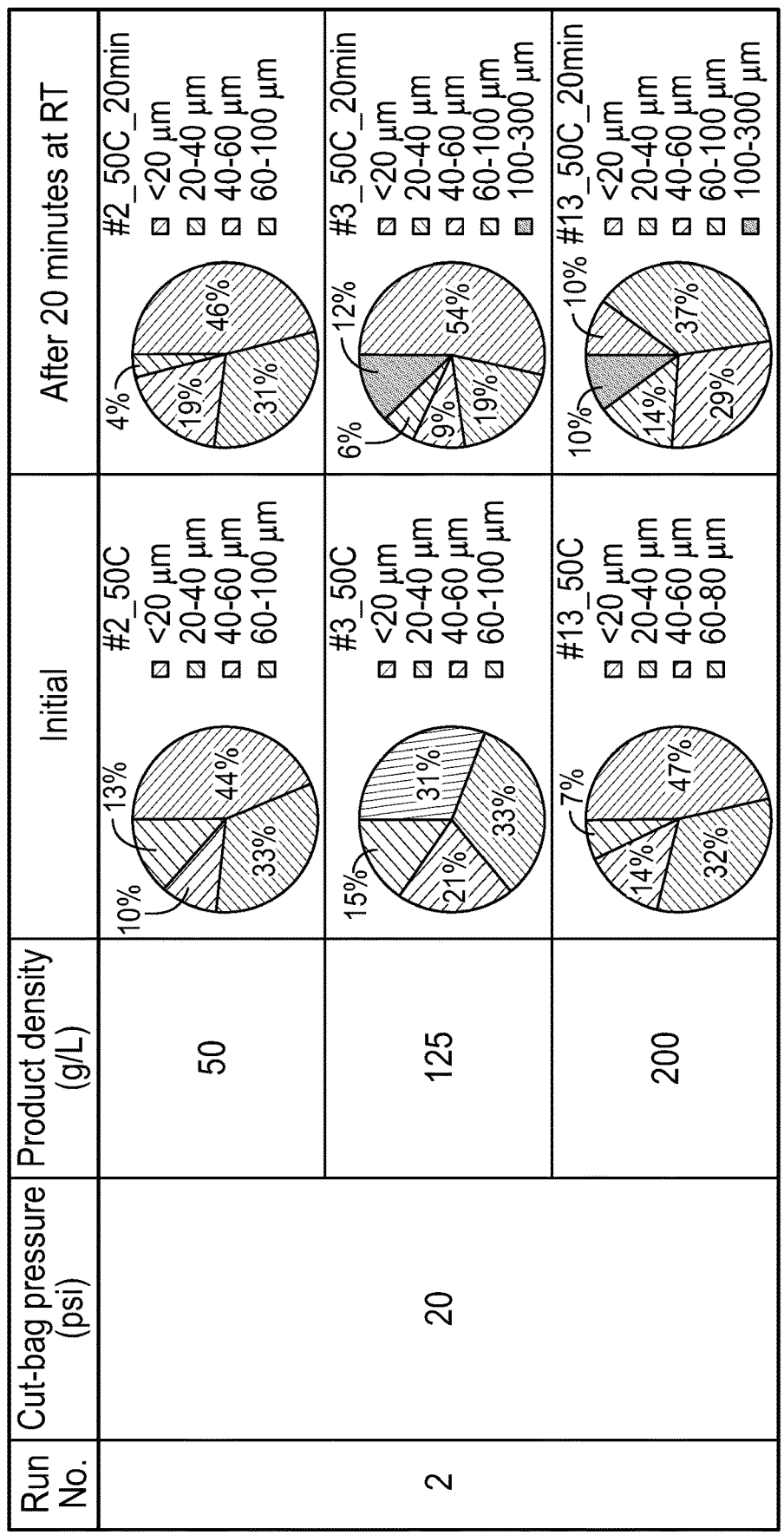
Figure 37:
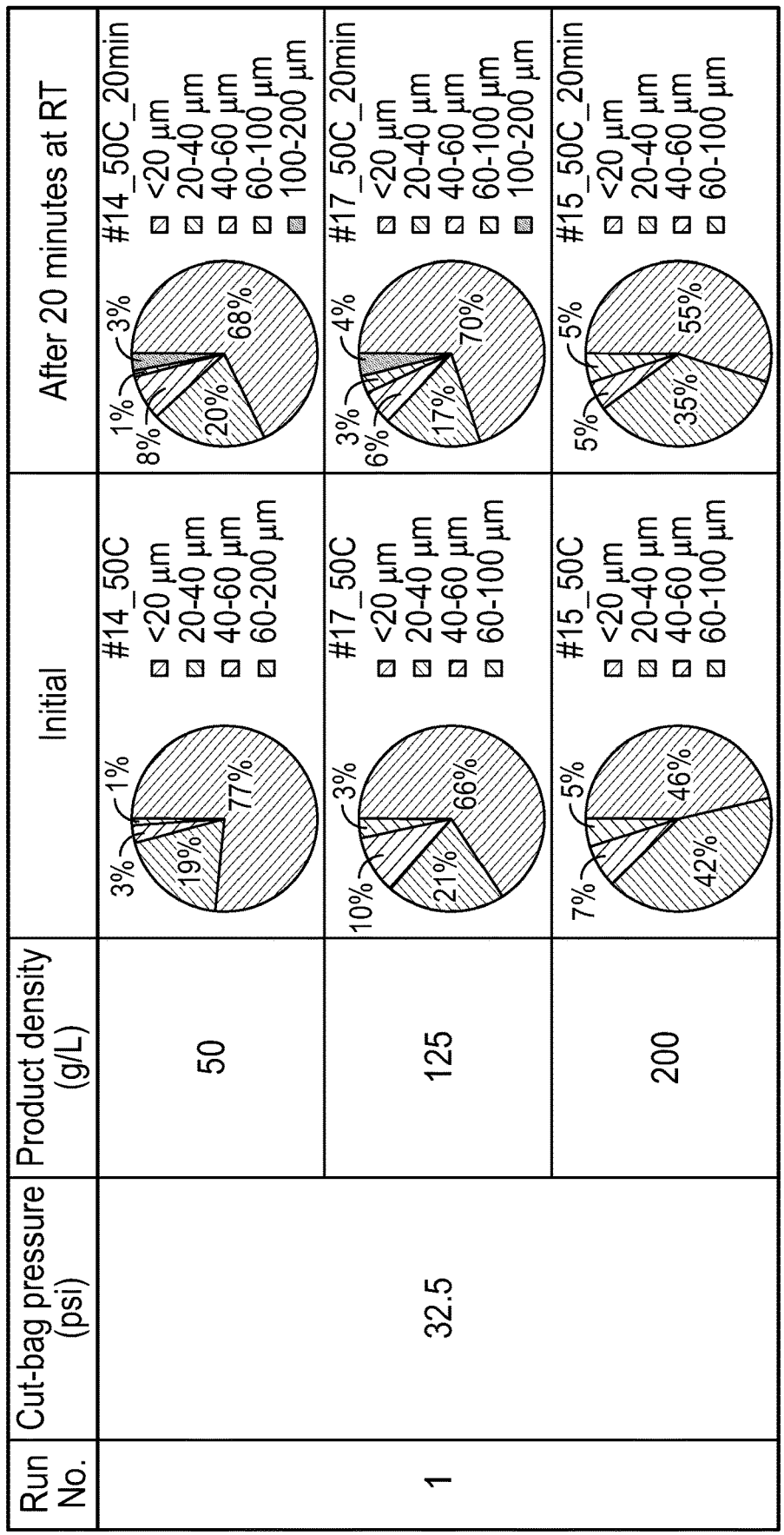
FIG. 37 Distribution of gas bubbles ($N_2O$) in photomicrographs (at 500× magnification) for "whipped-foam" delivered from whipped sunscreen samples (manufactured at cut-bag pressure 32.5 psi with various product densities), which had been stored at 50° C./75% RH for 1 week.
Figure 37:
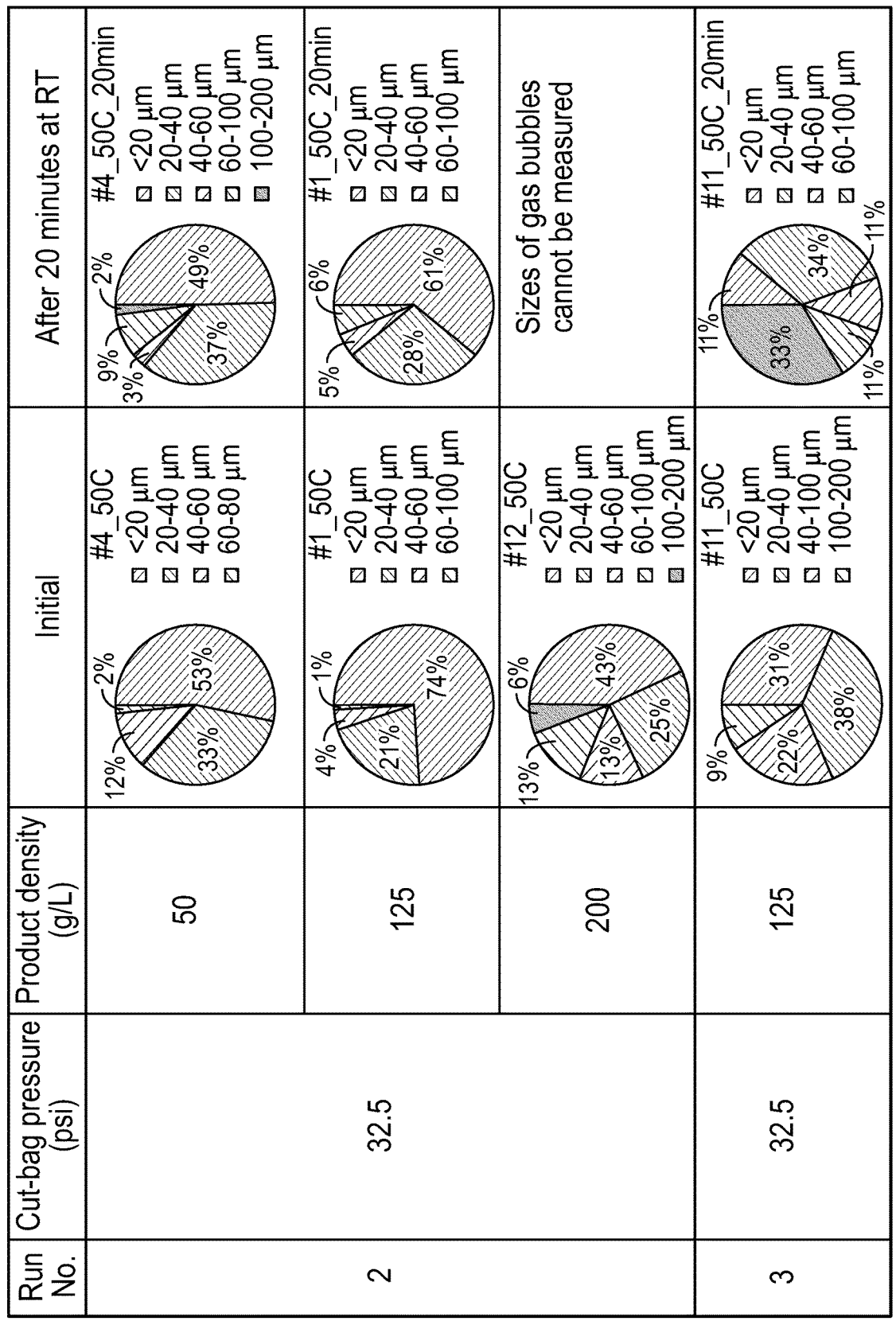
Figure 38:
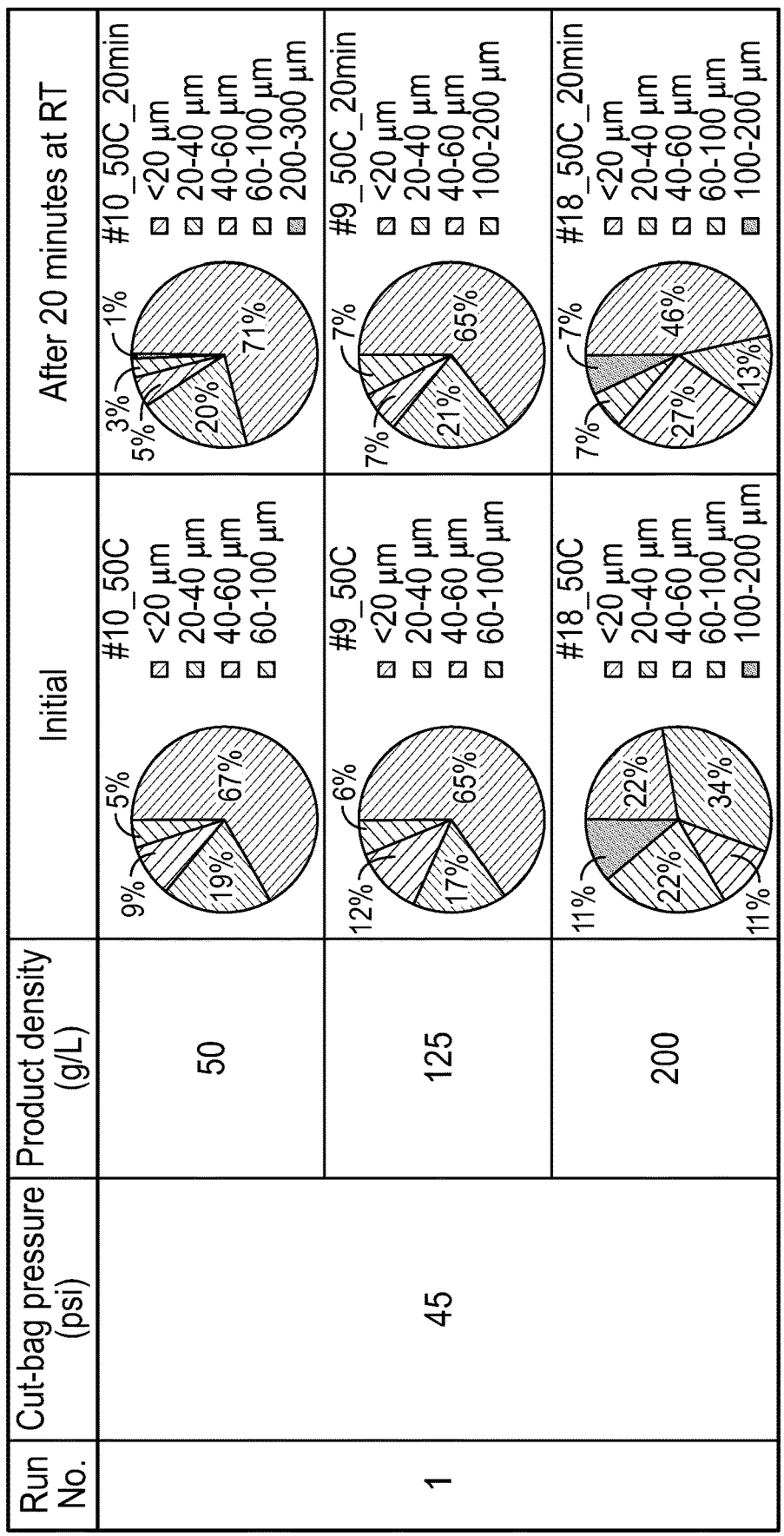
FIG. 38 Distribution of gas bubbles ($N_2O$) in photomicrographs (at 500× magnification) for "whipped-foam" delivered from whipped sunscreen samples (manufactured at cut-bag pressure 45 psi with various product densities), which had been stored at 50° C./75% RH for 1 week.
Figure 38:
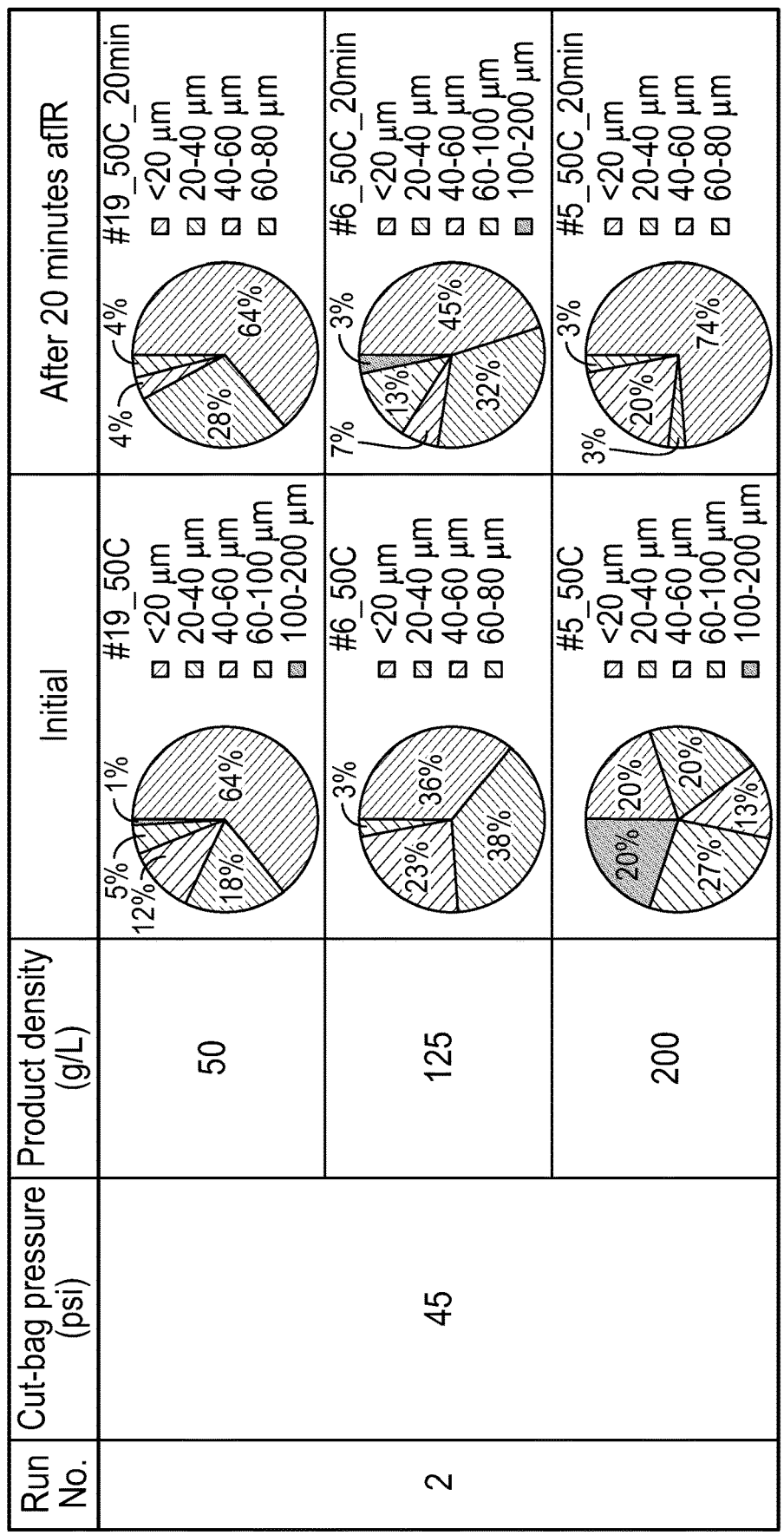

High temperature stability: no significant changes in appearance of "whipped foam", bubble size and distribution at 50° C. (FIG. 18).

Changes in cut-bag pressure have minimal effect on "whipped foam" characteristics.

Both the bubble density (FIG. 19) and number of bubbles (FIG. 20) in each density/cut bag pressure variable sampled showed: Increases in bubble density/bubble number at low product density and low cut bag pressure; Decreases in bubble density/bubble number at high density and high cut bag pressure. This appears to be the result of the lower density variables containing more entrapped gas and having less external pressure to contain expansion of the bubbles. By contrast, the higher density product contains less gas and is capable of repressing bubble size due to high exerted pressures on the formulation contained within.

In conclusion, a single finished whipped lotion formulation, processed under a variety of conditions, is capable of possessing unique physical (pre-dispensed and post dispensed) characteristics. Furthermore, these characteristics often translate directly into the consumer experience and have been demonstrated to impact perceptible changes in key consumer criteria including auditory experience, skin feel, perception of the physical characteristics of the product, and application.

Fluid Dynamic Analysis

Fluid dynamic of "in can" product (finished product) was evaluated using CT Scan, which produces cross-sectional images (virtual "slices") of specific areas of a scanned object, allowing the user to see inside the object without cutting. Density (g/l) means product density (g/L); Cut Bag Pressure (PSIG) means Cut-bag Pressure (psi). Measured precision: Precision of fluid measurement (or CT number precision) was calculated to be: 1 SD: 0.5 HU; Max range: 2 HU. Results are shown in Table 7.

TABLE 7

| Sample | Mean fluid density (%) | SD | Mean Subresolution bubble density (%) | SD | Mean visible bubble density (%) | SD | Total bubble count (%) | SD | Mean # of visible bubbles | SD | Max # of bubbles | Density (g/l) | Bag pressure (PSIG) |
|---|---|---|---|---|---|---|---|---|---|---|---|---|---|
| 1 | 69.1 | 5.7 | 28.7 | 5.4 | 2.5 | 0.8 | 31.2 | 5.5 | 19.7 | 4.7 | 30 | 125 | 32.5 |
| 2 | 6.3 | 2.6 | 37.8 | 5.1 | 56.3 | 7.4 | 94.1 | 9.0 | 137.4 | 29.2 | 187 | 50 | 20 |
| 3 | 54.3 | 5.4 | 38.9 | 4 | 7.6 | 1.6 | 46.5 | 4.3 | 103.8 | 32 | 160 | 125 | 20 |
| 4 | 0 | 0.02 | 15.1 | 7.4 | 84.9 | 7.4 | 100.0 | 10.5 | 127.6 | 29.2 | 187 | 50 | 32.5 |
| 5 | 80.9 | 4.8 | 19 | 4.2 | 1.3 | 0.9 | 20.3 | 4.3 | 2.3 | 1.6 | 7 | 200 | 45 |
| 6 | 76.2 | 7 | 24 | 6.8 | 1 | 0.6 | 25.0 | 6.8 | 3.6 | 2.9 | 5 | 125 | 45 |
| 7 | 32 | 5.6 | 52.1 | 4 | 17.5 | 3.0 | 69.6 | 5.0 | 141.6 | 36 | 193 | 125 | 20 |

TABLE 7-continued

| Sample | Mean fluid density (%) | SD | Mean Subresolution bubble density (%) | SD | Mean visible bubble density (%) | SD | Total bubble count (%) | SD | Mean # of visible bubbles | SD | Max # of bubbles | Density (g/l) | Bag pressure (PSIG) |
|---|---|---|---|---|---|---|---|---|---|---|---|---|---|
| 8 | 67 | 9.8 | 31.8 | 7.1 | 2.1 | 1.2 | 33.9 | 7.2 | 21.3 | 1 | 56 | 200 | 20 |
| 9 | 78.1 | 5.9 | 22.24 | 5.4 | 1 | 0.8 | 23.2 | 5.5 | 2.8 | 3.1 | 3 | 125 | 45 |
| 10 | 26.4 | 6.3 | 69.6 | 5.2 | 4.3 | 1.9 | 73.9 | 5.5 | 108.7 | 33.9 | 162 | 50 | 45 |
| 11 | 72.4 | 5.4 | 28 | 3.9 | 3.2 | 0.8 | 31.2 | 4.0 | 14 | 5.4 | 30 | 125 | 32.5 |
| 12 | 78.2 | 6.2 | 22.11 | 6.02 | 1.5 | 0.9 | 23.6 | 6.1 | 3.5 | 2.3 | 14 | 200 | 32.5 |
| 13 | 69.6 | 5.7 | 28 | 5.9 | 2.1 | 1.1 | 30.1 | 6.0 | 2.6 | 8.3 | 46 | 200 | 20 |
| 14 | 21.7 | 6.6 | 76.2 | 6.6 | 2.6 | 1.9 | 78.8 | 6.9 | 108.8 | 37 | 138 | 50 | 32.5 |
| 15 | 79.2 | 7.9 | 17.9 | 11.8 | 1.4 | 0.8 | 19.3 | 11.8 | 2.9 | 1.8 | 8 | 200 | 32.5 |
| 16 | 24.3 | 16.7 | 56.8 | 9.7 | 24.3 | 7.4 | 81.1 | 12.2 | 118.8 | 24.7 | 112 | | |
| 17 | 59.6 | 6.1 | 38.8 | 5.6 | 2.5 | 1 | 41.3 | 5.7 | 35.8 | 12.3 | 66 | 125 | 32.5 |
| 18 | 80 | 8.4 | 20 | 5.6 | 2.1 | 1 | 22.1 | 5.7 | 3.4 | 3.6 | 8 | 200 | 45 |
| 19 | 20.5 | 5.2 | 72.2 | 4.1 | 7.5 | 3 | 79.7 | 5.1 | 142.3 | 36.1 | 193 | 50 | 45 |
| 20 | 20.9 | 2.1 | 61.9 | 3.4 | 18.9 | 1.5 | 80.8 | 3.7 | 183.4 | 13 | 205 | 50 | 20 | remove sample 4 due to questionable fluid mixture
Table Key
Fluid density (%): non bubble _ fluid _ = 100 Vol$_{non\_bubble\_fluid}$ Density$_{fluid}$
Note:
Vol$_{all\_fluid}$ includes total volume of sample within bag Note: Vol$_{all\_fluid}$ includes total volume of sample within bag

Example 6B

Whipped sunscreen products consisting of a base emulsion formulation (concentrate) and a propellant (gas) are packaged into a pre-pressurized Bag on Valve (BOV) package. The objective of this example is to evaluate the characteristics of whipped sunscreen products manufactured at various process conditions. Formulation details for a whipped sunscreen product used in the following evaluation studies are summarized in Tables 10 and 11. Batches were prepared based on the whipped sunscreen product SPF 50 at various levels of process conditions: three different cut-bag pressures (20, 32.5, and 45 psi) and three different product densities (50, 125, and 200 g/L). See Table 10. The batches tested in the evaluation studies were manufactured and packaged at the intended manufacturing site.

TABLE 8

Composition of Whipped Sunscreen Product (Finished Products)

| Ingredient | SPF 50 Concentration (% w/w) |
|---|---|
| Avicel RC-591 | 2.00 |
| Disodium EDTA | 0.10 |
| Ganex P-904 LC | 0.80 |
| Glycerin | 2.50 |
| Sunspheres PGL | 8.00 |
| Octocrylene | 8.00 |
| Octisalate, USP | 4.50 |
| Homosalate | 10.00 |
| Dicaprylyl Ether | 2.00 |
| Tocopherol | 0.25 |
| Avobenzone | 3.00 |
| Oxybenzone | 6.00 |
| Prolipid 141 | 4.50 |
| Lanette 22 (CM) | 2.00 |
| Cetyl Alcohol | 1.00 |
| Chlorphenesin | 0.27 |
| Sodium Ascorbyl Phosphate | 0.01 |
| Benzyl Alcohol | 0.90 |
| Waterbabies 5235646 | 0.25 |
| Dry-Flo Pure | 4.00 |
| Water | Q.S. |

TABLE 9

Concentrate (Base Formulation): Whipped Sunscreen Lotion Concentrate, Batch Size: 1000 g

| | Concentration (% w/w) | Manufacturing Directions |
|---|---|---|
| Part A Ingredients | | |
| Purified water, USP | 43.77 | Step 1: In a container large enough to hold the entire batch, add the Water of Part A, with rapid mixing, add the Avicel RC-591 of Part A and mix until free from lumps. |
| Avicel RC-591 | 2.00 | |
| Part B Ingredients | | |
| Disodium EDTA | 0.10 | Step 2: Add the ingredients of Part B to the batch of Step 1 and mix until dispersed. Begin heating the aqueous phase to 158-167° F. (70-75° C.) with mixing. |
| Ganex P-904 LC | 0.80 | |
| Glycerin, USP | 2.50 | |
| Sunspheres PGL | 8.00 | |
| Part C Ingredients | | |
| Octocrylene, USP | 8.00 | Step 3: In a separate container, add the ingredients of Part C and heat to 158-167° F. (70-75° C.) with mixing until dissolved. |
| Octisalate, USP | 4.50 | |
| Homosalate, USP | 10.00 | |
| Dicaprylyl Ether | 2.00 | |
| Vitamine E, USP | 0.25 | |
| Avobenzone, USP | 3.00 | Step 4: Add the oil phase of Step 3 to the batch of Step 2 and mix until homogenous. Turn off heat and cool to at least 113° F. (45° C.). |
| Oxybenzone, USP | 6.00 | |
| Prolipid 141 | 4.50 | |
| Lanette 22 (CM) | 2.00 | |
| Cetyl Alcohol, NF | 1.00 | |
| Chlorphenesin | 0.27 | |

TABLE 9-continued

Concentrate (Base Formulation): Whipped
Sunscreen Lotion Concentrate, Batch Size: 1000 g

| | Concentration (% w/w) | Manufacturing Directions |
|---|---|---|
| Part D Ingredients | | |
| Sodium Ascorbyl Phosphate | 0.01 | Step 5: Add Part D ingredients to the batch then slowly added the Dry-Flo to the batch and mix well for at least 5 minutes. |
| Benzyl Alcohol, NF | 0.90 | |
| Fragrance | 0.40 | |
| Dry-Flo Pure | 4.00 | |
| Part E Ingredients | | |
| Purified water, USP | Q.S. | Step 6: Q.S. the batch with water of Part E and mix well. Package accordingly. |

TABLE 10

Samples

| SAMPLE | CUT BAG PRESSURE (psi) | DENSITY (g/L) |
|---|---|---|
| 170 | NEAT-NO GAS CONTROL | NEAT-NO GAS CONTROL |
| 567 | NEAT-NO GAS CONTROL | NEAT-NO GAS CONTROL |
| 852 | 20 | 50 |
| 819 | 32.5 | 50 |
| 903 | 45 | 50 |
| 33 | 20 | 125 |
| 754 | 32.5 | 125 |
| 90 | 45 | 125 |
| 707 | 20 | 200 |
| 836 | 32.5 | 200 |
| 125 | 45 | 200 |

The results are shown in FIG. 21-FIG. 38.

Example 7 Sensory Impact Studies

Two intertwined process variables may contribute to controlling the consumer experience associated with a base formulation: gas loading (e.g., Nitrous Oxide), which impacts density, spreadability, sound impact upon expelling from the package, and physical appearance of product; and pre-gas can pressure, which influences stability of gas emulsion, sound, speed of dispense, sputtering, and "quality" characteristics. Sensory impact (such as appearance, sound, and skin impact) to the user of product variants of these two variables were evaluated by trained personnel to determine how product variants are perceived differently by the user, with statistical confidence.

The sensory impact studies were conducted by Sensory Spectrum (222 Oak Ave, Kannapolis, NC 28081; 554 Central Ave, New Providence, NJ 07974). These studies involve skinfeel descriptive analysis of a whipped formulation. Whipped formulations with multiple variables are studied to understand impact of modified manufacturing processes on sensory characteristics of the formulation.

Study Design
Protocol Development

Sensory Spectrum consultants and panel leaders evaluate prototypes, method of dispensing/application and sound upon dispensing to develop a custom protocol for descriptive analysis. The Spectrum Descriptive Analysis Method grounds itself in the use of published and internal intensity reference scales to define intensity boundaries in sensory experiences. Skinfeel panelists are trained using the Spectrum Descriptive Analysis Method for personal care products. They are selected on their ability to detect and discriminate differences in visual and tactile properties. Panelists are trained on a universal scale that focuses on intensity or strength of the signal, coupled with detailed description and definitions of sensory attributes and use of calibrated training samples. All panelists receive a minimum of 100 hours of training and practice prior to commissioning of client research and are extensively trained in evaluation of sprays, creams, and related product forms.

Attribute intensity is rated on a 101-point intensity: scale with 0=none and 100=very strong/very high. The intensity scale uses 1-point increments. Panelists are trained to use the scale in a similar way across panelists and across samples. Use of a universal scale allows attributes to be compared in intensity to one another, (e.g. comparing intensity of slippery feel to intensity of sticky feel), as well as for comparison of samples within and across studies and products having shared attributes.

All evaluations are replicated. Data collection of this type is well suited to correlation with both instrumental and consumer research data. The samples are shown in Tables 6, 8, 9, and 10.

The study design involved monadic assessments of whipped sunscreen formulations in a randomized and balanced complete block design, and estimate mean values for each sensory attribute for each product. A trained panel performed all assessments using the Spectrum Descriptive Analysis Method.

The analyses provide both descriptive (qualitative) and intensity measures (quantitative) of the products. The descriptive analysis methodologies are based on those described in ASTM Manual 26, Sensory Testing Methods, 2nd Ed, E. Chambers IV, editor, and ASTM Manual on Descriptive Analysis Testing for Sensory Evaluation, R. Hootman, editor, and Sensory Evaluation Techniques by Meilgard, Civille and Carr.

Prototype Evaluations—Appearance

Sensory Spectrum consultants evaluated the color of the prototypes (hue, intensity, brightness, opacity) via consensus.

Prototype Evaluations—Sound

Sensory Spectrum's Skinfeel Descriptive analysis panel (minimum of eight panelists) was trained to evaluate the volume and pitch of the perceptible sounds of the prototypes as they were dispensed from their containers. They also assessed the presence/absence of qualitative characteristics of the sound.

Prototype Evaluations-Skinfeel Panel Composition: Eight (8) to eleven (11) trained panelists evaluated the products. All panelists passed an annual validation test.

Test Article Description

The sunscreen test articles/products contain sunscreen ingredients that comply with the types, combinations and concentrations specified by the 1999 FDA Final Sunscreen Monograph or subsequent FDA regulations. All products are over-labeled and bulk packaged and/or over-labeled in their marketed packaging. Products that are not sunscreens may also be tested as benchmarks along with the sunscreen test articles/products.

Test Article Description: Whipped Sunscreen SPF 50 Lotion; Sunscreen Lotion SPF 50 Non-Whipped.

Procedures

Two 4"×2" rectangular evaluation sites were scribed on each volar forearm. Panelists spread the product within the rectangle with index or middle finger, using a gentle oval motion, at a rate of two strokes per second.

Whipped Product Dispensing Instructions:

Pick up can and with other hand twist actuator noting that the icon moves from the locked position to the unlocked. Place index finger into saddle-shaped curve in actuator in preparation to dispense. Rotate can down at an angle, so that the actuator orifice is positioned close (¼ inch) to the petri dish, in preparation to dispense. Depress actuator and allow product to dispense by building into itself on the petri dish and then slowly pull can up and away. Release the actuator after 2 beats of a metronome set at 120 BPM. NOTE: This amount may be enough to cover a whole appendage (arm, leg, or one side of a torso).

Neat Product Dispensing Instructions: In a plastic petri dish, the panel leader or technician dispenses the product from a standard bottle in a spiral shape using a nickel size circle, filling it from the edge to the center.

No adverse events were reported.

The study sampling plan used a randomized and balanced complete block design. Nine samples (Tables 6, 8, 9, and 10) were replicated so that each sample was seen twice by each panelist, and one sample was seen three times by each panelist. The average of the replicate evaluations by each panelist was used in the summary analysis for each attribute. Mean and standard deviation for each attribute was analyzed for each sample. SAS was used to conduct this analysis.

Perceptual maps of the samples were developed to better understand the relationships among the attributes that define the sensory space of the sample category tested and where the products fall in that space. This information is used to group samples in homogeneous groups.

Some of the findings are:

Chroma/Intensity (of Color)

Density appeared to provide a directional impact regarding Chroma and Intensity but statistics were not available.

Cracking/Popping

Both Density and Cut Bag Pressure appeared to provide a directional impact regarding Cracking/Popping noise but statistics were not available.

Sputtering

Both Density and Cut Bag Pressure at lower densities appeared to provide a directional impact regarding Sputtering but statistics were not available.

Noise

Density appeared to provide a directional impact regarding Noise but statistics were not available.

Sound

Overall, many of the samples have a low sound impact when dispensed from the packaging. Three samples are moderately loud and high-pitched. One sample makes a crackling/popping sound while two samples sputter when dispensed.

Three Key Dimensions explain 90% of the variability in descriptive profiles of skinfeel. Dimension 1-Oily during rubout with a glossy thick, greasy residue (53% of variability) Dimension 2-Glossy and low in firmness when dispensed (19% of variability). Dimension 3-Visually compact when dispensed into a petri dish (18% of variability).

Prototypes that stand out in Dimension 1 are as follows. Prototype 836 is oily and slow to absorb during rubout, leaves a moderately glossy finish on the skin, and has the highest, thickest residue that is oily & greasy in character. Prototype 567 absorbs quickly, is less glossy, and leaves a thinner residue.

Prototypes that stand out in Dimension 2 are as follows. When dispensed into a petri dish, Prototype 170 is the shiniest among all prototypes for up to 30 seconds. It is also the least firm when manipulated, but it should be noted that this sample was evaluated slightly differently due to its format (neat, not whipped). Prototype 819 is least glossy when dispensed into a petri dish, and is firmest among the whipped prototypes.

Prototypes that stand out in Dimension 3 are as follows. When dispensed into a petri dish, Prototypes 170 and 903 are visually compact and hold their shape. Prototypes 033, 125 & 567 are airier when dispensed and don't hold their shape as well as other prototypes.

Tables 11-16 display some of the data. Attribute intensity is rated on a 101-point intensity: scale with 0=none and 100=very strong/very high.

TABLE 11

Sound Impact

| Sample | Attributes | |
| --- | --- | --- |
|  | Volume | Tone |
| 033 | 6.0 CD | 7.0 C |
| 090 | 4.8 D | 4.9 CD |
| 125 | 3.2 E | 3.5 D |
| 170* | n/a | n/a |
| 567 | 6.9 C | 7.2 C |
| 707 | 3.2 E | 3.5 D |
| 754** | 4.8 D | 5.6 CD |
| 819 | 41.5 A | 41.2 A |
| 836 | 3.1 E | 3.0 D |
| 852 | 38.1 B | 36.8 B |
| 903 | 40.1 A | 42.6 A |
| p-value | <.0001 | <.0001 |
| lsd | 1.50 | 2.93 |
| sig | ** | ** |

*Lotion format; dispensed via pipette

**Sample was replicated twice for a total of 3 evaluations

TABLE 12

Color Sensory Spectrum consultants evaluated via consensus the color of the prototypes when dispensed into a petri dish.

|  | Hue (qualitative) | Chroma | Intensity* (means) | Opacity |
| --- | --- | --- | --- | --- |
| 033 | yellow | 76.4 | 7.8 | 100.0 |
| 090 | yellow | 63.7 | 10.1 | 100.0 |
| 125 | yellow | 71.6 | 9.2 | 100.0 |
| 170 | yellow | 68.4 | 8.2 | 100.0 |
| 567 | white | 75.6 | 0.0 | 100.0 |
| 707 | yellow | 70.0 | 8.7 | 100.0 |
| 754 | yellow | 70.1 | 8.1 | 100.0 |
| 819 | white | 85.9 | 0.0 | 100.0 |
| 836 | yellow | 74.3 | 6.5 | 100.0 |
| 852 | white | 86.0 | 0.0 | 100.0 |
| 903 | white | 84.7 | 0.0 | 100.0 |

NOTES:

Standard 15-point scale was used for this evaluation

*White is the absence of color, therefore the intensity = 0

TABLE 13

Rubout

| Attributes | 033 | 090 | 125 | 170 | 567 | 707 | 754 | 819 | 836 | 852 | 903 | p-value | lsd |
|---|---|---|---|---|---|---|---|---|---|---|---|---|---|
| Wetness-RO | 52.2 DE | 51.9 E | 56.4 AB | 54.0 CD | 46.8 G | 52.5 DE | 54.8 BC | 48.7 FG | 58.0 A | 53.9 CD | 49.5 F | <.0001 | 1.99 |
| Spreadability-RO | 64.6 DEF | 66.8 BCD | 68.1 ABC | 64.9 DEF | 62.9 FG | 69.3 AB | 67.8 ABC | 61.1 G | 70.2 A | 65.5 CDE | 63.1 EFG | <.0001 | 2.55 |
| Coolness-RO | 6.1 FG | 8.0 CD | 8.9 BC | 7.5 DE | 6.5 EFG | 10.1 AB | 7.9 CD | 5.5 G | 10.5 A | 6.9 DEF | 5.9 FG | <.0001 | 1.32 |
| Thickness-RO | 36.0 BC | 36.4 BC | 36.0 BC | 35.6 C | 34.9 C | 37.5 AB | 35.9 BC | 35.6 BC | 39.1 A | 34.7 C | 35.5 C | 0.0003 | 1.83 |
| Slipperiness-RO | 72.0 D | 75.4 B | 79.9 A | 72.5 CD | 67.9 F | 80.4 A | 74.8 BC | 70.2 DEF | 80.7 A | 71.3 DE | 69.2 EF | <.0001 | 2.38 |
| Oil-RO | 23.3 DEF | 23.4 DE | 28.0 B | 20.8 EFG | 19.7 G | 27.0 BC | 24.6 CD | 21.3 EFG | 31.5 A | 21.8 DEFG | 20.4 FG | <.0001 | 2.95 |
| Wax-RO | 10.1 BCDE | 9.2 CDE | 8.9 DE | 12.4 A | 10.2 ABCD | 8.9 DE | 11.5 AB | 10.0 BCDE | 7.9 E | 10.6 ABCD | 11.4 ABC | 0.0040 | 2.20 |
| Grease-RO | 35.3 CD | 38.6 AB | 39.2 AB | 35.2 CD | 33.7 DE | 40.4 A | 36.9 BC | 35.0 CD | 39.8 A | 31.9 E | 35.7 CD | <.0001 | 2.80 |
| Whitening-RO | 18.5 C | 16.9 C | 53.2 B | 14.8 CD | 4.5 E | 52.8 B | 20.8 C | 7.4 DE | 75.7 A | 5.3 E | 6.6 DE | <.0001 | 8.20 |
| Rubs to Absorbency | 53.9 C | 44.5 D | 74.3 B | 35.0 EF | 35.0 EF | 71.5 B | 41.8 DE | 32.4 F | 93.1 A | 33.5 EF | 30.4 F | <.0001 | 8.54 |

Means that share a common letter within an attribute are not statistically significantly different at the indicated CL
All are Significantly different at 95% confidence level Means that share a common letter within an attribute are not statistically significantly different at the indicated CL All are Significantly different at 958 confidence level

TABLE 14

Immediate Afterfeel

| Attributes | 033 | 090 | 125 | 170 | 567 | 707 | 754 | 819 | 836 | 852 | 903 | p-value | lsd | sig |
|---|---|---|---|---|---|---|---|---|---|---|---|---|---|---|
| Gloss-Imm | 21.4 CD | 23.0 C | 34.2 B | 20.6 CDE | 16.0 E | 36.1 B | 22.5 C | 19.3 CDE | 46.9 A | 17.6 DE | 16.8 DE | <.0001 | 4.63 | ** |
| Whitening-Imm | 2.4 C | 3.0 C | 12.9 B | 2.8 C | 0.7 C | 16.8 B | 3.1 C | 1.7 C | 32.9 A | 1.6 C | 2.5 C | <.0001 | 5.22 | ** |
| Tautness-Imm | 15.4 | 15.2 | 15.4 | 15.4 | 15.2 | 15.0 | 15.4 | 15.3 | 15.4 | 15.6 | 15.2 | 0.4690 | | |
| Stickiness-Imm | 8.3 C | 8.6 C | 8.7 C | 8.4 C | 6.2 D | 10.5 B | 9.4 BC | 6.5 D | 12.7 A | 8.2 C | 6.0 D | <.0001 | 1.53 | ** |
| Roughness-Imm | 18.2 A | 18.5 A | 18.6 A | 18.7 A | 18.7 A | 18.0 A | 18.4 A | 18.8 A | 16.5 B | 19.0 A | 18.8 A | 0.0002 | 1.02 | ** |
| Slipperiness-Imm | 67.2 CD | 69.4 BC | 69.5 BC | 69.7 B | 66.3 D | 69.9 B | 70.2 B | 70.1 B | 73.2 A | 70.5 B | 71.5 AB | <.0001 | 2.36 | ** |
| Thickness of Residue-Imm | 17.5 B | 17.3 B | 18.9 B | 15.1 C | 12.3 E | 19.2 B | 17.6 B | 12.8 DE | 22.4 A | 14.5 CD | 13.5 CDE | <.0001 | 1.98 | ** |
| Amount of Residue-Imm | 25.5 D | 25.6 D | 29.0 BC | 22.0 E | 17.5 F | 30.0 B | 26.4 CD | 18.4 F | 39.0 A | 19.9 EF | 18.9 F | <.0001 | 2.86 | ** |
| Oily Intensity-Imm | 14.2 CD | 15.3 CD | 20.8 B | 14.0 CDE | 11.3 E | 20.5 B | 16.3 C | 13.4 DE | 24.8 A | 14.8 CD | 12.8 DE | <.0001 | 2.84 | ** |
| Waxy Intensity-Imm | 18.0 | 19.5 | 21.3 | 21.0 | 20.2 | 19.7 | 18.7 | 22.2 | 18.0 | 19.0 | 21.0 | 0.1774 | . | |
| Greasy Intensity-Imm | 30.5 CD | 32.3 C | 35.1 AB | 31.7 CD | 26.5 E | 36.6 A | 32.5 BC | 29.4 D | 37.5 A | 30.7 CD | 31.4 CD | <.0001 | 2.74 | ** |
| Silicone Intensitly-Imm | 1.1 BCD | 0.9 BCD | 3.0 A | 0.7 BCD | 0.0 D | 1.4 BC | 0.3 CD | 0.7 BCD | 1.8 AB | 0.5 CD | 0.5 CD | 0.0008 | 1.29 | ** |
| Plastic/Coated Intensity-Imm | 3.5 A | 2.7 AB | 0.0 D | 2.7 AB | 2.7 AB | 1.8 BC | 1.5 BC | 1.8 BC | 0.9 CD | 2.3 ABC | 1.8 BC | 0.0003 | 1.47 | ** |

Means that share a common letter within an attribute are not statistically significantly different at the indicated CL
** = Significantly different at 95% confidence level
* = Significantly different at 90% confidence level
lsd = Is reported at 95% if p-value < 0.05 and 90% if 0.05 < p-value < 0.10

TABLE 15

10-minute Afterfeel

| Attributes | 033 | 090 | 125 | 170 | 567 | 707 | 754 | 819 | 83 | 852 | 903 | p-value | lsd |
|---|---|---|---|---|---|---|---|---|---|---|---|---|---|
| Gloss-10 Min | 14.0 BC | 13.7 BC | 19.1 A | 13.2 BCD | 11.3 D | 17.5 A | 14.4 B | 12.2 BCD | 19.6 A | 12.5 BCD | 11.7 CD | <.0001 | 2.29 |
| Whitening-10 Min | 0.8 C | 1.0 C | 3.6 B | 0.5 C | 0.0 C | 5.5 AB | 0.2 C | 0.0 C | 6.8 A | 0.5 C | 0.5 C | <.0001 | 1.92 |
| Tautness-10 Min | 14.5 | 14.9 | 15.1 | 14.8 | 14.9 | 14.4 | 15.0 | 15.1 | 15.1 | 14.9 | 14.9 | 0.4953 | . |
| Stickiness-10 Min | 3.9 CD | 3.5 D | 4.9 BC | 3.0 DE | 2.0 EF | 6.0 B | 3.9 CD | 1.3 F | 7.4 A | 2.9 DE | 1.8 EF | <.0001 | 1.26 |
| Roughness-10 Min | 18.9 | 19.0 | 19.2 | 18.9 | 18.9 | 18.7 | 18.8 | 18.8 | 18.1 | 19.3 | 18.8 | 0.3659 | . |
| Slipperiness-10 Min | 74.4 AB | 73.3 BCD | 72.0 D | 74.3 ABC | 72.9 BCD | 72.3 CD | 74.4 AB | 75.7 A | 74.0 ABC | 74.5 AB | 75.5 A | 0.0049 | 2.02 |
| Thickness of Residue-10 Min | 11.1 DE | 12.0 CD | 13.4 BC | 9.7 EF | 8.2 G | 13.4 B | 11.6 D | 8.7 FG | 16.2 A | 9.7 EF | 8.4 FG | <.0001 | 1.43 |
| Amount of Residue-10 Min | 15.9 CD | 16.9 C | 19.7 B | 14.0 DE | 12.1 EF | 20.0 B | 15.9 CD | 11.7 F | 25.0 A | 13.5 EF | 11.6 F | <.0001 | 1.96 |
| Oily Intensity-10 Min | 7.8 CDE | 8.3 CD | 12.8 B | 8.1 CD | 5.7 E | 13.9 B | 9.2 C | 7.1 CDE | 16.2 A | 9.0 C | 6.1 DE | <.0001 | 2.20 |
| Waxy Intensity-10 Min | 21.4 CD | 23.5 BC | 24.0 BC | 23.7 BC | 23.1 BCD | 23.5 BC | 22.2 CD | 27.8 A | 19.9 D | 5.8 AB | 26.2 AB | 0.0007 | 3.38 |
| Greasy Intensity-10 Min | 24.2 CD | 27.0 BC | 26.9 BC | 24.5 CD | 18.6 E | 28.2 B | 26.5 BC | 23.2 D | 31.6 A | 23.6 D | 22.6 D | <.0001 | 2.85 |
| Silicone Intensity 10 Min | 0.9 | 1.6 | 1.8 | 2.3 | 2.0 | 1.7 | 1.2 | 3.3 | 1.9 | 1.6 | 2.0 | 0.1559 | . |
| Plastic/Coated Intensity-10 Min | 4.2 A | 2.7 BCD | 1.8 DE | 3.2 ABC | 2.7 BCD | 3.6 AB | 2.1 CDE | 2.3 CDE | 1.4 E | 2.7 BCD | 2.7 BCD | 0.0006 | 1.20 |

Means that share a common letter within an attribute are not statistically significantly different at the indicated CL
All except for Roughness-10 Min and Silicone Intensity-10 Min are significantly different at 95% confidence level

TABLE 16

Manipulation

| Attributes | 033 | 090 | 125 | 170 | 567 | 707 | 754 | 819 | 836 | 852 | 903 | p-value | lsd |
|---|---|---|---|---|---|---|---|---|---|---|---|---|---|
| Firmness in Hand/Firmness | 42.8 B | 41.5 BC | 39.4 D | 31.4 F | 39.1 D | 36.8 E | 36.7 E | 46.6 A | 36.3 E | 40.3 CD | 40.8 CD | <.0001 | 1.95 |
| Stickiness | 29.4 AB | 29.6 A | 28.3 ABC | 25.6 F | 26.7 DEF | 28.6 ABC | 26.4 EF | 28.1 BCD | 28.4 ABC | 27.7 CDE | 26.3 EF | <.0001 | 1.46 |
| Cohesiveness | 9.3 B | 8.8 BCD | 9.5 B | 11.3 A | 8.3 CDE | 9.2 BC | 8.6 BCDE | 7.8 E | 9.3 B | 9.1 BC | 7.9 DE | <.0001 | 0.94 |
| Peaking | 31.2 B | 27.7 BC | 31.3 B | 38.6 A | 26.0 CD | 31.3 B | 31.4 B | 16.9 F | 26.9 C | 23.1 DE | 20.6 EF | <.0001 | 3.81 |

Means that share a common letter within an attribute are not statistically significantly different at the indicated CL
All are significantly different at 95% confidence level

TABLE 17

Appearance

| Attributes | 033 | 090 | 125 | 170 | 567 | 707 | 754 | 819 | 836 | 852 | 903 | p-value | lsd |
|---|---|---|---|---|---|---|---|---|---|---|---|---|---|
| Visual Compactness- | 75.5 EF | 77.5 CDE | 73.2 F | 84.3 A | 73.9 F | 76.3 DEF | 80.4 BC | 81.1 AB | 79.1 BCD | 80.4 BC | 81.5 AB | <.0001 | 3.51 |

TABLE 17-continued

| | Appearance | | | | | | | | | | | | |
|---|---|---|---|---|---|---|---|---|---|---|---|---|
| Attributes | 033 | 090 | 125 | 170 | 567 | 707 | 754 | 819 | 836 | 852 | 903 | p-value | lsd |
| Imm | | | | | | | | | | | | | |
| Integrity of Shape-Imm | 81.0 DE | 80.5 DE | 79.1 E | 87.1 A | 78.8 E | 79.2 E | 83.1 CD | 83.3 BCD | 73.3 F | 85.7 ABC | 86.5 AB | <.0001 | 3.34 |
| Gloss-Imm | 80.6 AB | 80.4 AB | 80.1 AB | 81.5 A | 79.7 B | 80.7 AB | 80.6 AB | 76.0 D | 80.0 AB | 79.7 B | 78.1 C | <.0001 | 1.48 |
| Visual Compactness-10 Sec | 75.4 EF | 77.1 CDE | 73.2 F | 83.9 A | 73.5 F | 76.1 DEF | 80.1 BC | 80.5 AB | 78.9 BCD | 80.1 BC | 81.4 AB | <.0001 | 3.38 |
| Integrity of Shape-10 Sec | 79.5 CD | 78.3 CD | 78.3 CD | 85.5 A | 77.1 D | 78.4 CD | 81.8 BC | 79.0 CD | 72.3 E | 84.1 AB | 85.8 A | <.0001 | 3.51 |
| Gloss-10 Sec | 80.6 AB | 80.4 AB | 80.1 AB | 81.5 A | 79.7 B | 80.7 AB | 80.6 AB | 76.0 D | 80.0 AB | 79.7 B | 78.1 C | <.0001 | 1.48 |
| Visual Compactness-30 Sec | 75.3 DE | 77.1 CD | 73.4 E | 83.6 A | 73.6 E | 76.0 DE | 80.1 BC | 80.3 ABC | 78.6 BCD | 80.0 BC | 81.3 AB | <.0001 | 3.39 |
| Integrity of Shape-30 Sec | 78.4 CD | 77.1 DE | 76.9 DE | 84.5 A | 75.0 EF | 77.4 DE | 80.9 BC | 77.2 DE | 71.6 F | 83.5 AB | 85.3 A | <.0001 | 3.40 |
| Gloss-30 Sec | 80.6 AB | 80.4 AB | 80.1 AB | 81.5 A | 79.7 B | 80.7 AB | 80.6 AB | 76.0 D | 80.0 AB | 79.7 B | 78.1 C | <.0001 | 1.48 |
| Visual Compactness-60 Sec | 74.8 EF | 77.0 CDE | 72.7 F | 83.3 A | 73.1 F | 75.6 DEF | 80.0 ABC | 80.2 ABC | 78.7 BCD | 79.9 BC | 81.4 AB | <.0001 | 3.40 |
| Integrity of Shape-60 Sec | 76.7 C | 76.1 C | 75.3 C | 83.8 AB | 73.8 CD | 76.4 C | 80.5 B | 76.2 C | 70.8 D | 83.1 AB | 84.8 A | <.0001 | 3.43 |
| Gloss-60 Sec | 80.1 AB | 81.5 A | 80.6 AB | 79.5 BC | 80.7 AB | 80.6 AB | 76.0 D | 80.0 AB | 79.7 B | 80.4 AB | 78.1 C | <.0001 | 1.48 |

Means that share a common letter within an attribute are not statistically significantly different at the indicated CL
All are significantly different at 95% confidence level Means that share a common letter within an attribute are not statistically significantly different at the indicated CL
All are significantly different at 95% confidence level
A summary of the study parameters is below.

As it is Dispensed
  a. Firmness
  b. Stickiness
  c. Integrity of Shape
  d. Peaking
  e. Gloss vs Dull (matte to Shinniness)
  f. Sound
    i. During Dispensing
      1. Loudness
      2. Harshness
      3. Whoosh?
      4. Fart sound?
    ii. During Pinching for Firmness
      1. Crackling/Popping
  g. Porosity (Dense whip-cream vs Foam, which has large porosity)
  h. Coloration (scale ranging from yellow to white), where white is not a bad thing but indicates amount of gas in product
Rub-Out
  a. Wetness
  b. Spreadability
  c. Thickness
  d. Oil
  e. Wax
  f. Grease
  g. Whitening
  h. Rubs to Absorb
  i. Crackling/Popping as rubbing out
  j. Cooling
  k. Cushioning/Softness
  l. Density of Dollup (volume vs weight)
Afterfeel
  a. Immediate
    i. Gloss
    ii. Whitening
    iii. Stickiness
    iv. Thickness of Residue
    v. Amount of Residue
    vi. Oil
    vii. Wax
    viii. Grease
    ix. Silicone
    x. Plastic coated
  b. After 10 minutes
    i. Gloss
    ii. Whitening
    iii. Stickiness
    iv. Thickness of Residue
    v. Amount of Residue
    vi. Oil
    vii. Wax
    viii. Grease
    ix. Silicone
    x. Plastic coated

OTHER EMBODIMENTS

The foregoing description discloses only exemplary embodiments of the invention.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the appended claims. Thus, while only certain features of the invention have been illustrated and described, many modifications and changes will occur to those skilled in the art. It is therefore to be understood that the appended claims are intended to cover all such modifications and changes as fall within the true spirit of the invention.

What is claimed is:

1. A whipped formulation expelled from a pressurized package, the formulation comprising one or more active agents, which one or more active agent in the formulation is co-mingled with a whipping agent prior to being filled under pressure into said package and prior to being expelled from said package; wherein said whipping agent is added in sufficient amounts to be dispersed in the formulation; the whipping agent being dispersed in the formulation by rapidly mixing the formulation, with all ingredients blended, in a high shear, continuous-flow, high-pressure whipping head, pressurized under controlled temperature, rate of flow, and pressure, which rapidly mixes the formulation with a series of infusion gas injector ports controlling the gas propellant pressure and rates;
   wherein said pressurized package is under sufficient pressure suitable to maintain the whipping agent dispersed in the formulation prior to the whipped formulation being expelled from said package; and
   wherein said pressurized package, prior to the whipped formulation being expelled from said package, is under sufficient pressure to expel said formulation as a whipped formulation upon application of external force on said formulation in said package; wherein said whipping agent is methane, ethane, butane, pentanes, propane, isobutene, N-butane, 1,1-Difluoroethane, hydrocarbons, dimethyl ether, 1,3,3,3-tetrafluoropropene, or 1,1,1,2-tetrafluoroethane.

2. The formulation of claim 1, wherein said package comprises a pressure generating and maintaining component, wherein said component comprises one or more gas and/or liquid propellants which are not co-mingled with the formulation.

3. The formulation of claim 1, wherein said formulation is for topical application.

4. The formulation of claim 1, wherein said package is a bag on valve (BOV) pressurized assembly, comprising a fill and dispensing valve, an attached internal high barrier bag affixed to said valve, and rigid container adapted to holding positive pressure affixed to the valve.

5. The formulation of claim 1, wherein said formulation is a sunscreen and said active ingredient is a sunscreen active ingredient.

6. A method of preparing a whipped formulation, comprising:
   Rapidly mixing a formulation, with all ingredients blended, with a gas propellant in a high shear, continuous-flow, high-pressure whipping head, pressurized under controlled temperature, rate of flow, and pressure, which rapidly mixes the formulation with a series of infusion gas injector ports controlling the gas propellant pressure and rates, wherein said gas propellant is methane, ethane, butane, pentanes, propane, isobutene, N-butane, 1,1-Difluoroethane, hydrocarbons, dimethyl ether, 1,3,3,3-tetrafluoropropene, 1,1,1,2-tetrafluoroethane, or combination thereof.

7. The method of claim 6, further comprising:
   Filling said formulation into a package; wherein said propellant is added in sufficient amounts to be dispersed in the formulation;
   wherein said pressurized package is under sufficient pressure suitable to maintain the first gas propellant dispersed in the formulation; and
   wherein said pressurized package is under sufficient pressure to expel said formulation as a whipped formulation upon application of external force on said formulation in said package.

8. A pressurized package comprising a whippable formulation, the formulation comprising one or more active agents, which one or more active agents in the formulation is co-mingled with a whipping agent prior to being filled under pressure into said package;
   wherein said whipping agent is added in sufficient amounts to be dispersed in the formulation;
   wherein the whipping agent is dispersed in the formulation by rapidly mixing the formulation, with all ingredients blended, in a high shear, continuous-flow, high-pressure whipping head, pressurized under controlled temperature, rate of flow, and pressure, which rapidly mixes the formulation with a series of infusion gas injector ports controlling the gas propellant pressure and rates;
   wherein said pressurized package is under sufficient pressure suitable to maintain the whipping agent dispersed in the formulation; and
   wherein said pressurized package is under sufficient pressure to expel said formulation as a whipped formulation upon application of external force on said formulation in said package; wherein said whipping agent is methane, ethane, butane, pentanes, propane, isobutene, N-butane, 1,1-Difluoroethane, hydrocarbons, dimethyl ether, 1,3,3,3-tetrafluoropropene, or 1,1,1,2-tetrafluoroethane.

9. The package of claim 8, wherein said package maintains at least a minimal amount of pressure until substantially all the formulation in the package is expelled as a whipped formulation.

10. The package of claim 8, wherein said package comprises a pressure generating and maintaining component, wherein said component comprises one or more second gas and/or liquid propellants which are not co-mingled with the formulation.

11. The package of claim 8, wherein said package is a bag on valve (BOV) pressurized assembly, comprising a two-way fill and dispensing, an attached internal high barrier bag affixed to said valve, and rigid container adapted to holding positive pressure affixed to the valve.

12. The package of claim 8, wherein said formulation is a sunscreen and said active ingredient is a sunscreen active ingredient.

13. The package of claim 8, wherein said formulation has at least about 60% of the gas bubbles at ≤100 μm, after being expelled from the package.

14. A whipped formulation produced by the method of claim 6.

15. The method of claim 7, wherein said package maintains at least a minimal amount of pressure until substantially all the formulation in the package is expelled as a whipped formulation.

16. The method of claim 7, wherein said package comprises a pressure generating and maintaining component, wherein said component comprises one or more second gas and/or liquid propellants which are not co-mingled with the formulation.

17. The method of claim 7, wherein said package is a bag on valve (BOV) pressurized assembly, comprising a two-way fill and dispensing valve, an attached internal high barrier bag affixed to said valve, and rigid container adapted to holding positive pressure, affixed to the valve.

\* \* \* \* \*